United States Patent
Hatakeyama et al.

(10) Patent No.: US 11,703,760 B2
(45) Date of Patent: Jul. 18, 2023

(54) FLUOROCARBOXYLIC ACID-CONTAINING MONOMER, FLUOROCARBOXYLIC ACID-CONTAINING POLYMER, RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masahiro Fukushima, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 147 days.

(21) Appl. No.: 17/223,256

(22) Filed: Apr. 6, 2021

(65) Prior Publication Data
US 2021/0341839 A1 Nov. 4, 2021

(30) Foreign Application Priority Data

Apr. 28, 2020 (JP) ................................. 2020-079676

(51) Int. Cl.
| | | |
|---|---|---|
| G03F 7/004 | (2006.01) | |
| G03F 7/11 | (2006.01) | |
| G03F 7/039 | (2006.01) | |
| G03F 7/038 | (2006.01) | |
| C07C 69/653 | (2006.01) | |
| C08F 220/24 | (2006.01) | |
| C08F 220/28 | (2006.01) | |
| C08F 212/14 | (2006.01) | |
| C08F 220/30 | (2006.01) | |
| C08F 220/22 | (2006.01) | |

(52) U.S. Cl.
CPC .......... *G03F 7/0392* (2013.01); *C07C 69/653* (2013.01); *C08F 212/24* (2020.02); *C08F 220/22* (2013.01); *C08F 220/24* (2013.01); *C08F 220/281* (2020.02); *C08F 220/282* (2020.02); *C08F 220/283* (2020.02); *C08F 220/301* (2020.02); *C08F 220/303* (2020.02); *G03F 7/0046* (2013.01); *G03F 7/0382* (2013.01); *G03F 7/0397* (2013.01); *G03F 7/11* (2013.01); *C07C 2601/08* (2017.05)

(58) Field of Classification Search
CPC ........ G03F 7/11; G03F 7/0045; G03F 7/0046; G03F 7/0392; G03F 7/0397; G03F 7/0382
See application file for complete search history.

(56) References Cited

U.S. PATENT DOCUMENTS

| | | | |
|---|---|---|---|
| 7,906,269 B2 | 3/2011 | Isono et al. | |
| 8,097,401 B2* | 1/2012 | Huang | C08F 212/34 430/323 |
| 8,187,787 B2* | 5/2012 | Isono | C08F 220/24 430/326 |
| 8,647,812 B2* | 2/2014 | Fujii | G03F 7/0046 430/913 |
| 8,871,421 B2* | 10/2014 | Kanda | G03F 7/0397 430/913 |
| 9,152,050 B2 | 10/2015 | Hatakeyama | |
| 9,250,523 B2 | 2/2016 | Hatakeyama et al. | |
| 9,459,533 B2* | 10/2016 | Christianson | G03F 7/0046 |
| 9,543,147 B2* | 1/2017 | Liu | C08F 220/18 |
| 9,760,010 B2* | 9/2017 | Hatakeyama | G03F 7/2041 |
| 11,181,823 B2 | 11/2021 | Hatakeyama et al. | |
| 2009/0061353 A1* | 3/2009 | Isono | C08F 214/18 526/248 |
| 2009/0130591 A1* | 5/2009 | Yao | G03F 7/091 430/311 |
| 2009/0181322 A1* | 7/2009 | Ito | G03F 7/2041 430/281.1 |
| 2011/0104612 A1 | 5/2011 | Anno et al. | |
| 2012/0083580 A1* | 4/2012 | Kinsho | C07C 69/73 526/242 |

(Continued)

FOREIGN PATENT DOCUMENTS

| | | |
|---|---|---|
| CN | 102099749 A | 6/2011 |
| CN | 102603586 A | 7/2012 |

(Continued)

OTHER PUBLICATIONS

Office Action dated Dec. 13, 2021, issued in counterpart to TW Application No. 110114865. (8 pages).

(Continued)

*Primary Examiner* — Amanda C. Walke
(74) *Attorney, Agent, or Firm* — WHDA, LLP

(57) ABSTRACT

A fluorocarboxylic acid-containing polymer comprising recurring units having formula (A1), but not acid labile group-containing recurring units is provided. A resist composition comprising the same offers a high sensitivity and is unsusceptible to nano-bridging or pattern collapse independent of whether it is of positive or negative tone.

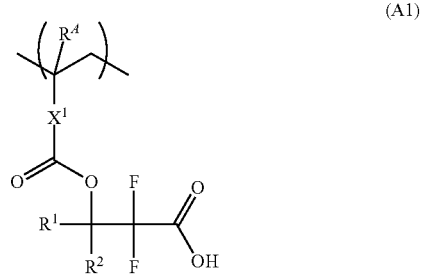

(A1)

13 Claims, No Drawings

(56) References Cited

U.S. PATENT DOCUMENTS

| | | | |
|---|---|---|---|
| 2012/0129108 A1 | 5/2012 | Aqad et al. | |
| 2014/0051024 A1* | 2/2014 | Kinsho | C08F 220/22 |
| | | | 526/245 |
| 2016/0035564 A1* | 2/2016 | Aibara | H01L 21/6715 |
| | | | 134/4 |
| 2019/0064664 A1* | 2/2019 | Fukushima | G03F 7/0397 |
| 2019/0170906 A1* | 6/2019 | Hatakeyama | G02B 1/111 |
| 2020/0089112 A1 | 3/2020 | Hatakeyama et al. | |

FOREIGN PATENT DOCUMENTS

| | | | |
|---|---|---|---|
| JP | 2007-297590 A | | 11/2007 |
| JP | 2008158149 A | * | 7/2008 |
| JP | 5446144 B2 | | 3/2014 |
| JP | 2014-67012 A | | 4/2014 |
| JP | 2014-67014 A | | 4/2014 |
| JP | 5577572 B2 | | 8/2014 |
| KR | 10-2012-0000496 A | | 1/2012 |
| KR | 10-2020-0032659 A | | 3/2020 |

OTHER PUBLICATIONS

Office Action dated Feb. 20, 2023, issued in counterpart KR application No. 10-2021-0054091, with English translation. (15 pages).

* cited by examiner

FLUOROCARBOXYLIC ACID-CONTAINING MONOMER, FLUOROCARBOXYLIC ACID-CONTAINING POLYMER, RESIST COMPOSITION AND PATTERNING PROCESS

CROSS-REFERENCE TO RELATED APPLICATION

This non-provisional application claims priority under 35 U.S.C. § 119(a) on Patent Application No. 2020-079676 filed in Japan on Apr. 28, 2020, the entire contents of which are hereby incorporated by reference.

TECHNICAL FIELD

This invention relates to a fluorocarboxylic acid-containing monomer, fluorocarboxylic acid-containing polymer, resist composition, and pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

The EUV lithography has the problem that defects in a mask blank consisting of total 80 layers of Mo and Si are transferred, and the problem that a high transmittance, high strength pellicle which causes only a little lowering of fight intensity and is devoid of the risk of failure during exposure is not available, allowing particles to deposit from the exposure tool onto a mask. It is urgently required to reduce defects. Since the EUV lithography enables to form patterns to a feature size of less than half of the size achieved by the standard ArF immersion lithography, the probability of defect occurrence is increased. A higher level of defect control is thus necessary.

In conjunction with resist materials for the ArF immersion lithography, Patent Document 1 proposes a fluorinated polymer additive which segregates on the surface of a resist film to improve water repellency. This additive containing a 1,1,1,3,3,3-hexafluoro-2-propanol (HFA) group is effective for improving the solubility in alkaline developer at the resist film surface and reducing bridge defects on the resist surface.

There is known a resist composition for ArF immersion lithography comprising a fluorinated polymer comprising recurring units of fluorocarboxylic acid structure substituted with a fluoroalkyl group or acid labile group. After the resist composition is applied, the fluorinated polymer segregates on the resist film surface. In the case of fluoroalkyl group-substituted fluorocarboxylic acid, partial elimination reaction takes place in alkaline developer so that carboxyl groups are resumed, resulting in improved solubility in alkaline developer. In the case of acid labile group-substituted fluorocarboxylic acid, acid-catalyzed deprotection reaction takes place so that carboxyl groups are resumed, resulting in improved solubility in alkaline developer.

Patent Documents 2 and 3 disclose that a polymer comprising recurring units having a HFA group and robust recurring units having an aromatic group is added for reducing outgassing from the resist film during EUV exposure. The modification of resist film surface can lead to a possibility of reducing pattern defects or suppressing outgassing.

Patent Documents 4 and 5 disclose negative and positive resist compositions comprising base polymers comprising recurring units of specific fluorocarboxylic acid structure. Since the dissolution rate of fluorocarboxylic acid in alkaline developer is very high, a negative or positive resist composition comprising a base polymer having added thereto fluorocarboxylic acid-containing recurring units is difficult to control its solubility in alkaline developer.

CITATION LIST

Patent Document 1: JP-A 2007-297590
Patent Document 2: JP-A 2014-067014 (U.S. Pat. No. 9,152,050)
Patent Document 3: JP-A 2014-067012 (U.S. Pat. No. 9,250,523)
Patent Document 4: JP 5446144 (U.S. Pat. No. 8,187,787)
Patent Document 5: JP 5577572 (U.S. Pat. No. 7,906,269)

DISCLOSURE OF INVENTION

For the acid-catalyzed chemically amplified resist, it is desired to develop a resist composition capable of minimizing nano-bridging and collapse of line patterns and improving a sensitivity.

An object of the invention is to provide a resist composition which exhibits a high sensitivity and is unsusceptible to nano-bridging or pattern collapse, independent of whether it is of positive tone or negative tone; and a pattern forming process using the same.

The inventors have found that when a polymer comprising recurring units derived from a monomer having a specific fluorocarboxylic acid structure is added, there is obtained a resist composition which is effective for preventing nano-bridging and pattern collapse, providing a wide process margin, and forming a line pattern with improved LWR or a hole pattern with improved CDU. It is noted that the monomer is referred to as "fluorocarboxylic acid-containing monomer" and the polymer is referred to as "fluorocarboxylic acid-containing polymer," hereinafter.

In one aspect, the invention provides a fluorocarboxylic acid-containing monomer having the formula (A).

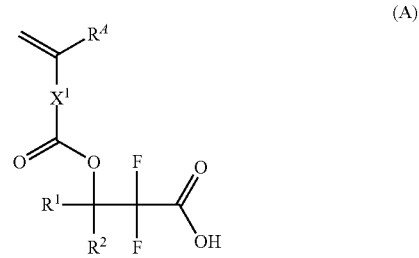

(A)

Herein $R^A$ is hydrogen or methyl. $R^1$ and $R^2$ are each independently hydrogen, or a $C_1$-$C_{10}$ saturated hydrocarbyl group, $C_2$-$C_8$ unsaturated aliphatic hydrocarbyl group, optionally substituted $C_6$-$C_{10}$ aryl group, or $C_4$-$C_{10}$ monovalent group obtained by combining the foregoing, with the proviso that $R^2$ is other than hydrogen when $R^1$ is a $C_1$-$C_4$ alkyl group, $R^1$ and $R^2$ may bond together to form a ring with the carbon atom to which they are attached. $X^1$ is a single bond, phenylene, naphthalenediyl or —C(=O)—O—$X^{11}$—, $X^{11}$ is a $C_1$-$C_{10}$ saturated hydrocarbylene group or phenylene group.

In another aspect, the invention provides a fluorocarboxylic acid-containing polymer comprising recurring units having the formula (A1), the polymer being free of recurring units containing an acid labile group.

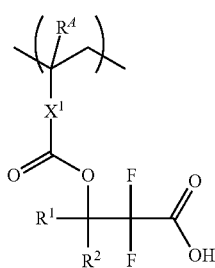

(A1)

Herein $R^A$ is hydrogen or methyl. $R^1$ and $R^2$ are each independently hydrogen, or a $C_1$-$C_{10}$ saturated hydrocarbyl group, $C_2$-$C_8$ unsaturated aliphatic hydrocarbyl group, optionally substituted $C_6$-$C_{10}$ aryl group, or $C_4$-$C_{10}$ monovalent group obtained by combining the foregoing, with the proviso that $R^2$ is other than hydrogen when $R^1$ is a $C_4$-$C_4$ alkyl group, $R^1$ and $R^2$ may bond together to form a ring with the carbon atom to which they are attached. $X^1$ is a single bond, phenylene, naphthalenediyl or —C(=O)—O—$X^{11}$—, $X^{11}$ is a $C_1$-$C_{10}$ saturated hydrocarbylene group or phenylene group.

Preferably the fluorocarboxylic acid-containing polymer further comprises recurring units of at least one type selected from recurring units having the formula (B) and recurring units having the formula (C).

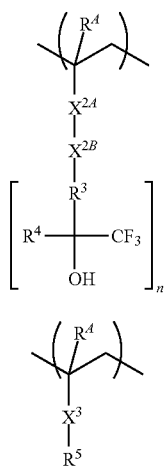

(B)

(C)

Herein $R^A$ is hydrogen or methyl, n is 1 or 2, $X^{2A}$ is a single bond, —O—, —C(=O)—O—, or —C(=O)—NH—, $X^{2B}$ is a $C_1$-$C_{12}$ (n+1)-valent saturated hydrocarbon group or (n+1)-valent aromatic hydrocarbon group, wherein some or all of the hydrogen atoms may be substituted by fluorine or hydroxyl, and some carbon may be replaced by an ester bond or ether bond. $X^3$ is a single bond, —O—, —C(=O)—O—$X^{31}$—$X^{32}$— or —C(=O)—NH—$X^{31}$—$X^{32}$—, wherein $X^{31}$ is a single bond or a $C_1$-$C_4$ alkanediyl group, $X^{32}$ is a single bond, ester bond, ether bond, or sulfonamide bond. $R^3$ is a single bond, ester bond, or $C_1$-$C_{12}$ saturated hydrocarbylene group wherein some or all of the hydrogen atoms may be substituted by fluorine, and some carbon may be replaced by an ester bond or ether bond. $R^4$ is hydrogen, fluorine, methyl, trifluoromethyl, or difluoromethyl. $R^3$ and $R^4$ may bond together to form a ring with the carbon atom to which they are attached, the ring may contain an ether bond, fluorine or trifluoromethyl. $R^5$ is a $C_1$-$C_{20}$ hydrocarbyl group substituted with at least one fluorine, wherein some carbon may be replaced by an ester bond or ether bond.

In a further aspect, the invention provides a resist composition comprising the fluorocarboxylic acid-containing polymer defined above and a base polymer.

Typically, 0.001 to 20 parts by weight of the fluorocarboxylic acid-containing polymer is present per 100 parts by weight of the base polymer.

The resist composition may further comprise an acid generator capable of generating a sulfonic acid, imide acid or methide acid.

The resist composition may further comprise an organic solvent.

Preferably, the base polymer comprises recurring units having the formula (a1) or recurring units having the formula (a2).

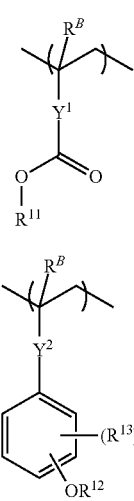

(a1)

(a2)

Herein $R^B$ is each independently hydrogen or methyl, $R^{11}$ and $R^{12}$ each are an acid labile group, $R^{13}$ is fluorine, trifluoromethyl, a $C_1$-$C_5$ saturated hydrocarbyl group or $C_1$-$C_5$ saturated hydrocarbyloxy group, $Y^1$ is a single bond, phenylene group, naphthylene group, or $C_1$-$C_{12}$ linking group containing at least one moiety selected from ester bond and lactone ring, $Y^2$ is a single bond or ester bond, and a is an integer of 0 to 4.

In one embodiment, the resist composition is a chemically amplified positive resist composition.

In another embodiment, the base polymer is free of an acid labile group. Typically, the resist composition is a chemically amplified negative resist composition.

In a preferred embodiment, the base polymer comprises recurring units of at least one type selected from recurring units having the formulae (f1) to (f3).

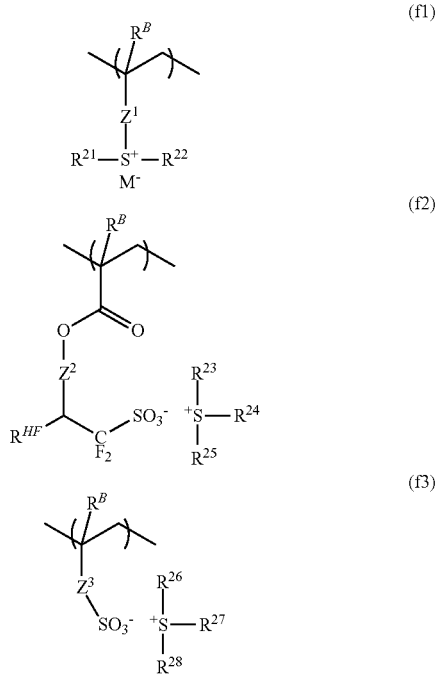

Herein $R^B$ is each independently hydrogen or methyl; $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxyl moiety; $Z^2$ is a single bond, —$Z^{21}$—C(=O)—O—, —$Z^{21}$—O— or —$Z^{21}$—O—C(=O)—, $Z^{21}$ is a $C_1$-$C_{12}$ saturated hydrocarbylene group which may contain a carbonyl moiety, ester bond or ether bond; $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety; $R^{21}$ to $R^{28}$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached; $R^{HF}$ is hydrogen or trifluoromethyl; and $M^-$ is a non-nucleophilic counter ion.

The resist composition may further comprise a surfactant.

In a further aspect, the invention provides a process for forming a pattern comprising the steps of applying the resist composition defined above onto a substrate to form a resist film thereon, exposing the resist film to high-energy radiation, and developing the exposed resist film in a developer.

Typically, the high-energy radiation is ArF excimer laser radiation of wavelength 193 nm, KrF excimer laser radiation of wavelength 248 nm, EB or EUV of wavelength 3 to nm.

Advantageous Effects of Invention

The monomer having formula (A) is a compound having fluorocarboxylic acid and a polymerizable double bond. The fluorocarboxylic acid-containing polymer obtained from polymerization of the monomer has a remarkably higher solubility in an alkaline developer than the polymers in which the carboxyl group is substituted with a base labile group or acid labile group. When a resist composition comprising the fluorocarboxylic acid-containing polymer and a base polymer is applied to form a resist film, the fluorocarboxylic acid-containing polymer segregates on the film surface. Thus the solubility of the resist film surface in alkaline developer is increased whereby bridge defects or pattern collapse after pattern formation is minimized and LWR or CDU is improved. By virtue of the improved solubility in alkaline developer and the increased absorption of EUV due to fluorine atoms, a high sensitivity is achievable.

DESCRIPTION OF EMBODIMENTS

As used herein, the singular forms "a," "an" and "the" include plural referents unless the context clearly dictates otherwise. The notation (Cn-Cm) means a group containing from n to m carbon atoms per group. As used herein, the term "fluorinated" and "iodized" compounds mean fluorine and iodine-containing compounds respectively. Also, the terms "group" and "moiety" are interchangeable.

The abbreviations and acronyms have tire following meaning.
  EB: electron beam
  EUV: extreme ultraviolet
  Mw: weight average molecular weight
  Mn: number average molecular weight
  Mw/Mn: molecular weight distribution or dispersity
  GPC: gel permeation chromatography
  PEB: post-exposure bake
  PAG: photoacid generator
  LWR: line width roughness
  CDU: critical dimension uniformity Fluorocarboxylic Acid-Containing Monomer One embodiment of the invention is a fluorocarboxylic acid-containing monomer having the formula (A).

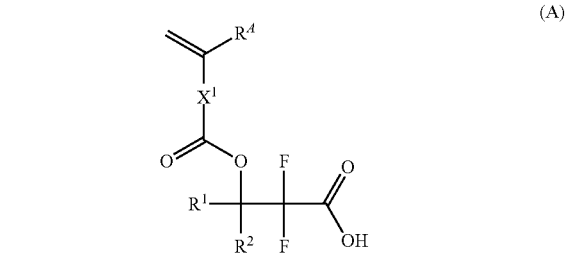

In formula (A), $R^A$ is hydrogen or methyl.

In formula (A), $R^1$ and $R^2$ are each independently hydrogen, or a $C_1$-$C_{10}$ saturated hydrocarbyl group, $C_2$-$C_8$ unsaturated aliphatic hydrocarbyl group, optionally substituted $C_6$-$C_{10}$ aryl group, or $C_4$-$C_{10}$ monovalent group obtained by combining the foregoing, with the proviso that $R^2$ is other than hydrogen when $R^1$ is a $C_1$-$C_4$ alkyl group. Also, $R^1$ and $R^2$ may bond together to form a ring with the carbon atom to which they are attached.

The $C_1$-$C_{10}$ saturated hydrocarbyl group represented by $R^1$ and $R^2$ may be straight, branched or cyclic and examples thereof include $C_1$-$C_{10}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, and $C_3$-$C_{10}$ cyclic saturated hydrocarbyl groins such as cyclopropyl, cyclopentyl, cyclohexyl, cyclopropylmethyl, 4-methylcyclohexyl, cyclohexylmethyl, norbornyl, and adamantyl.

The $C_2$-$C_8$ unsaturated aliphatic hydrocarbyl group represented by $R^1$ and $R^2$ may be straight, branched or cyclic and examples thereof include alkenyl groups such as vinyl, propenyl, butenyl, hexenyl; $C_2$-$C_8$ alkynyl groups such as ethynyl, propynyl and butynyl; $C_3$-$C_8$ unsaturated cycloaliphatic hydrocarbyl groups such as cyclohexenyl and norbornenyl.

Examples of the $C_6$-$C_{10}$ aryl group represented by $R^1$ and $R^2$ include phenyl, methylphenyl, ethylphenyl, n-propylphenyl, isopropylphenyl n-butylphenyl, isobutylphenyl, sec-butylphenyl, tert-butylphenyl, 1-naphthyl, and 2-naphthyl. In the aryl groups, some or all of the hydrogen atoms may be substituted by substituents such as $C_1$-$C_5$ saturated hydrocarbyloxy moieties, cyano, nitro, or halogen atoms.

In formula (A), $X^1$ is a single bond, phenylene, naphthalenediyl or —C(=O)—O—$X^{11}$—. $X^{11}$ is a $C_1$-$C_{10}$ saturated hydrocarbylene group or phenylene group. The $C_1$-$C_{10}$ saturated hydrocarbylene group represented by $X^{11}$ may be straight, branched or cyclic and examples thereof include alkanediyl groups such as methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-2,3-diyl, butane-1,4-diyl, 1,1-dimethylethane-1,2-diyl, pentane-1,5-diyl, 2-methylbutane-1,2-diyl, hexane-1,6-diyl, heptane-1,7-diyl, octane-1,8-diyl, nonane-1,9-diyl, and decane-1,10-diyl; cycloalkanediyl groups such as cyclopropane-1,1-diyl, cyclopropane-1,2-diyl, cyclobutane-1,1-diyl, cyclobutane-1,2-diyl, cyclobutane-1,3-diyl, cyclopentane-1,1-diyl, cyclopentane-1,2-diyl, cyclopentane-1,3-diyl, cyclohexane-1,1-diyl, cyclohexane-1,2-diyl, cyclohexane-1,3-diyl, cyclohexane-1,4-diyl; polycyclic saturated hydrocarbylene groups such as norbornanediyl and adamantanediyl; and hydrocarbylene groups obtained by combining the foregoing.

Examples of the fluorocarboxylic acid-containing monomer having formula (A) are shown below, but not limited thereto. Herein $R^4$ is as defined above.

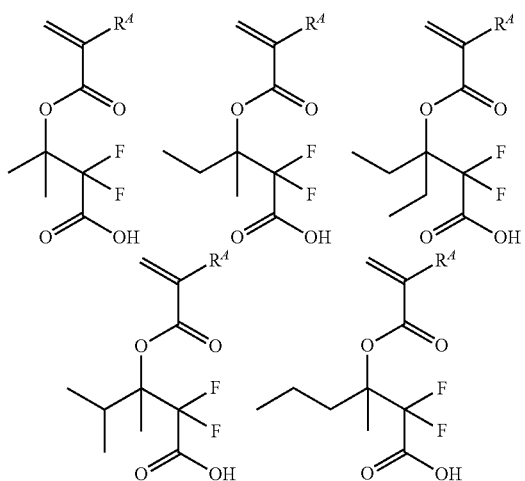
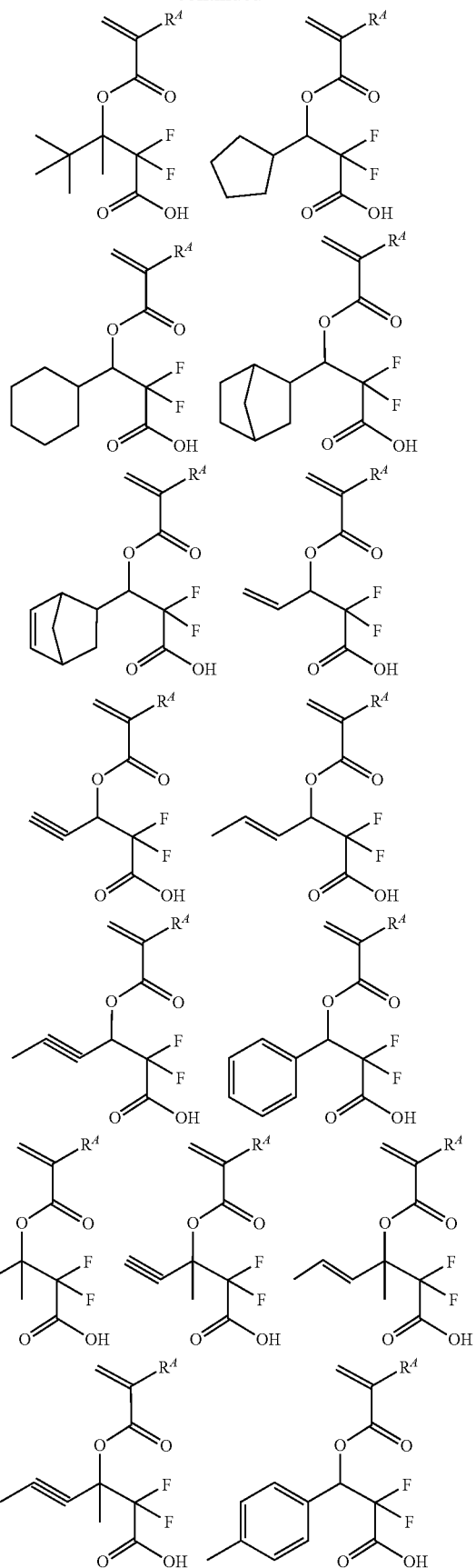

-continued
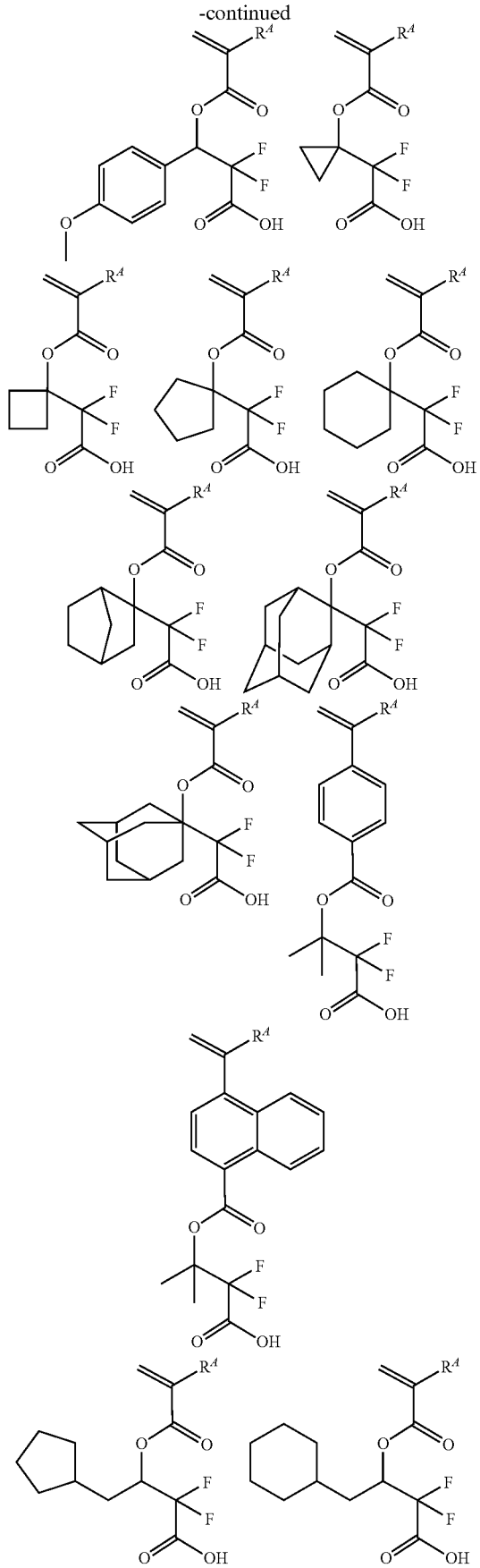
-continued
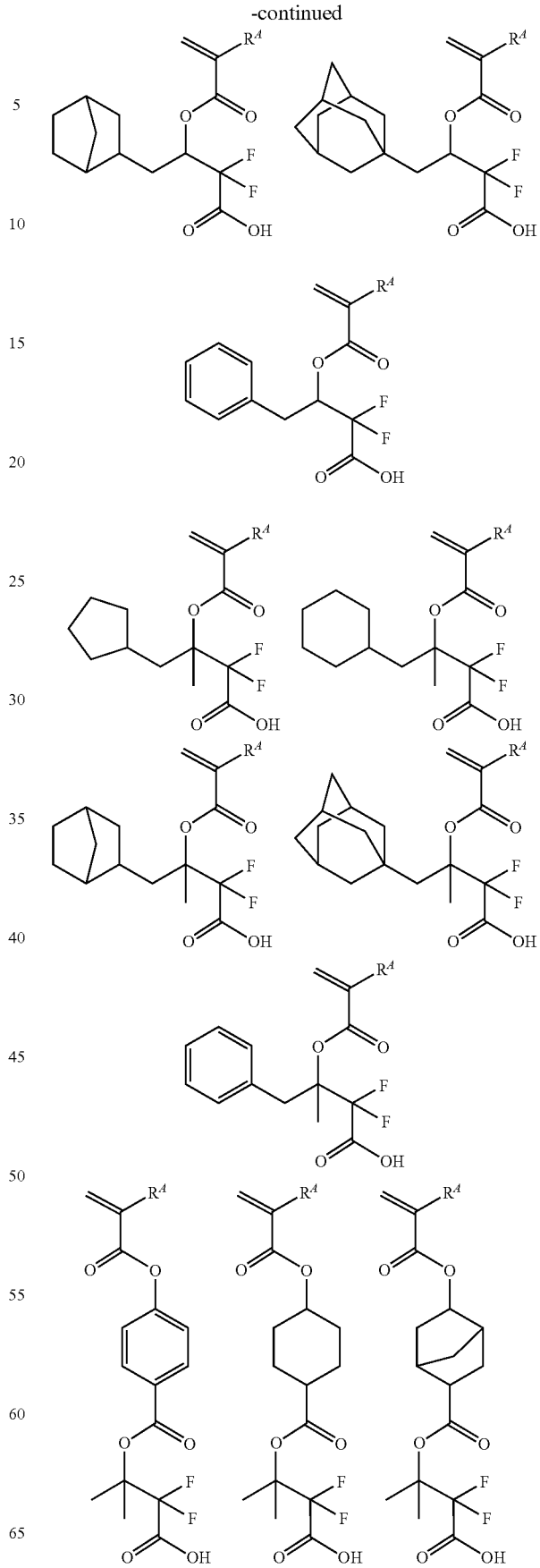

-continued

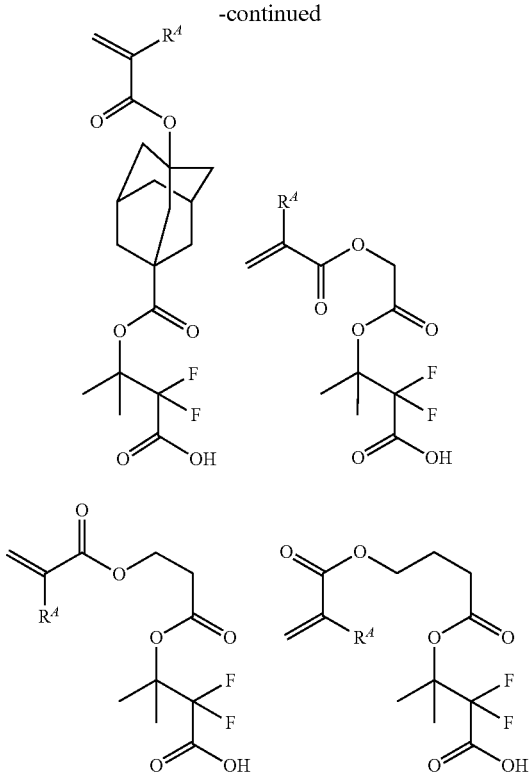

Fluorocarboxylic Acid-Containing Polymer

A second embodiment of the invention is a fluorocarboxylic acid-containing polymer obtained from polymerization of the monomer having formula (A). The polymer comprise recurring units having the formula (A1), also referred to as recurring units (A1). The polymer should be free of recurring units containing an acid labile group.

(A1)

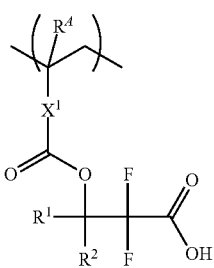

Herein $R^A$, $X^1$, $R^1$ and $R^2$ are as defined above.

The fluorocarboxylic acid-containing polymer may further comprise recurring units of at least one type selected from recurring units having an α-trifluoromethyl alcohol group, represented by the formula (B) and recurring units having a fluoroalkyl group, represented by the formula (C). The recurring units having formula (B) or (C) are also referred to as recurring units (B) or (C), hereinafter. The recurring units of at least one type selected from recurring units (B) and (C) serve, after resist film formation, to increase the efficiency of segregation of the fluorocarboxylic acid-containing polymer on the resist film surface.

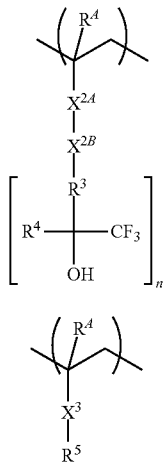

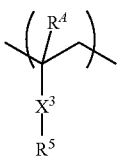

In formulae (B) and (C), $R^A$ is each independently hydrogen or methyl. In formula (B), n is 1 or 2.

In formula (B), $X^{2A}$ is a single bond, —O—, —C(=O)—O—, or —C(=O)—NH—. $X^{2B}$ is a $C_1$-$C_{12}$ (n+1)-valent saturated hydrocarbon group or (n+1)-valent aromatic hydrocarbon group, wherein some or all of the hydrogen atoms may be substituted by fluorine or hydroxyl, and some carbon may be replaced by an ester bond or ether bond.

The (n+1)-valent saturated hydrocarbon group represented by $X^{2B}$ may be straight, branched or cyclic and examples thereof include groups obtained by removing (n+1) number of hydrogen atoms from saturated hydrocarbons such as methane, ethane, propane, butane, pentane, hexane, heptane, octane, nonane, decane, undecane, dodecane, cyclopropane, cyclobutane, cyclopentane, cyclohexane, methylcyclopentane, ethylcyclopentane, methylcyclohexane, ethylcyclohexane, 1-propylcyclohexane, isopropylcyclohexane, norbornane, adamantane, methylnorbornane, ethylnorbornane, methyladamantane, ethyladamantane, and tetrahydrodicyclopentadiene. Examples of the (n+1)-valent aromatic hydrocarbon group represented by $X^{2B}$ include groups obtained by removing (n+1) number of hydrogen atoms from aromatic hydrocarbons such as benzene, toluene, xylene, ethylbenzene, 1-propylbenzene, isopropylbenzene, and naphthalene.

In formula (B), $R^3$ is a single bond, ester bond, or $C_1$-$C_{12}$ saturated hydrocarbylene group wherein some or all of the hydrogen atoms may be substituted by fluorine, and some carbon may be replaced by an ester bond or ether bond.

In formula (B), $R^4$ is hydrogen, fluorine, methyl, trifluoromethyl, or difluoromethyl. $R^3$ and $R^4$ may bond together to form a ring with the carbon atom to which they are attached, the ring may contain an ether bond, fluorine or trifluoromethyl.

In formula (C), $X^3$ is a single bond, —O—, —C(=O)—O—$X^{31}$—$X^{32}$— or —C(=O)—NH—$X^{31}$—$X^{32}$—, wherein $X^{31}$ is a single bond or a $C_1$-$C_4$ alkanediyl group, and $X^{32}$ is a single bond, ester bond, ether bond, or sulfonamide bond. Examples of the alkanediyl group represented by $X^{31}$ include those exemplified above for the alkanediyl group represented by $X^{11}$, but of 1 to 4 carbon atoms.

In formula (C), $R^5$ is a $C_1$-$C_{20}$ hydrocarbyl group substituted with at least one fluorine, wherein some carbon may be replaced by an ester bond or ether bond.

Examples of the monomer from which recurring units (B) are derived are shown below, but not limited thereto. Herein $R^A$ is as defined above.

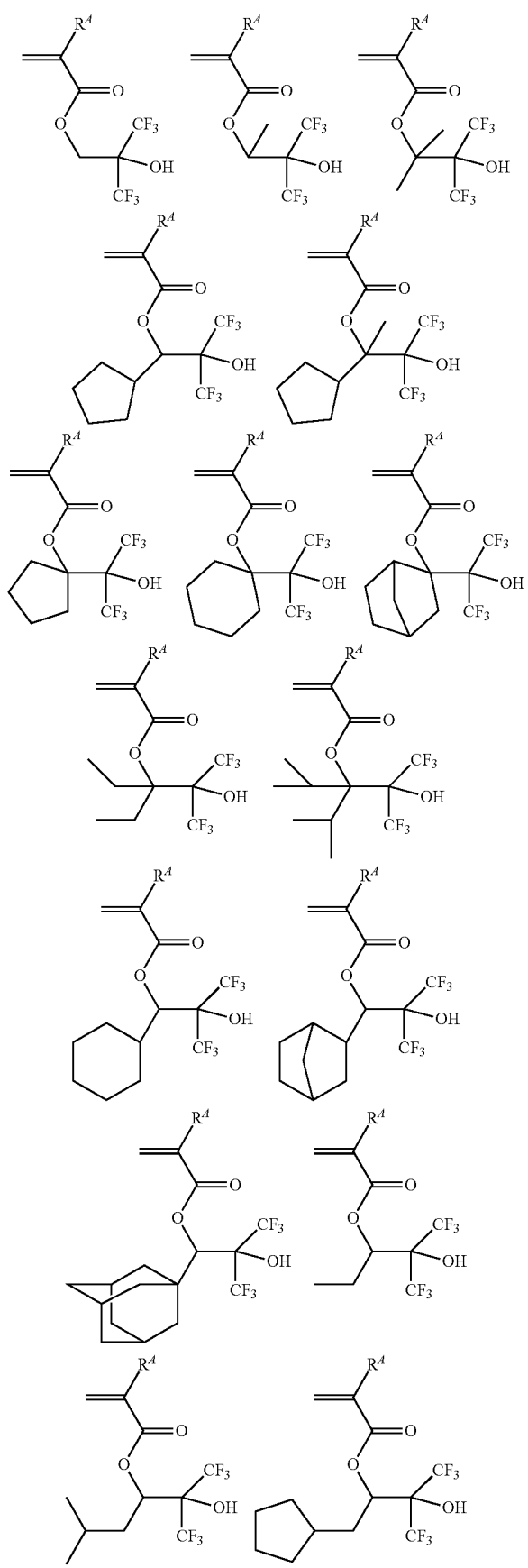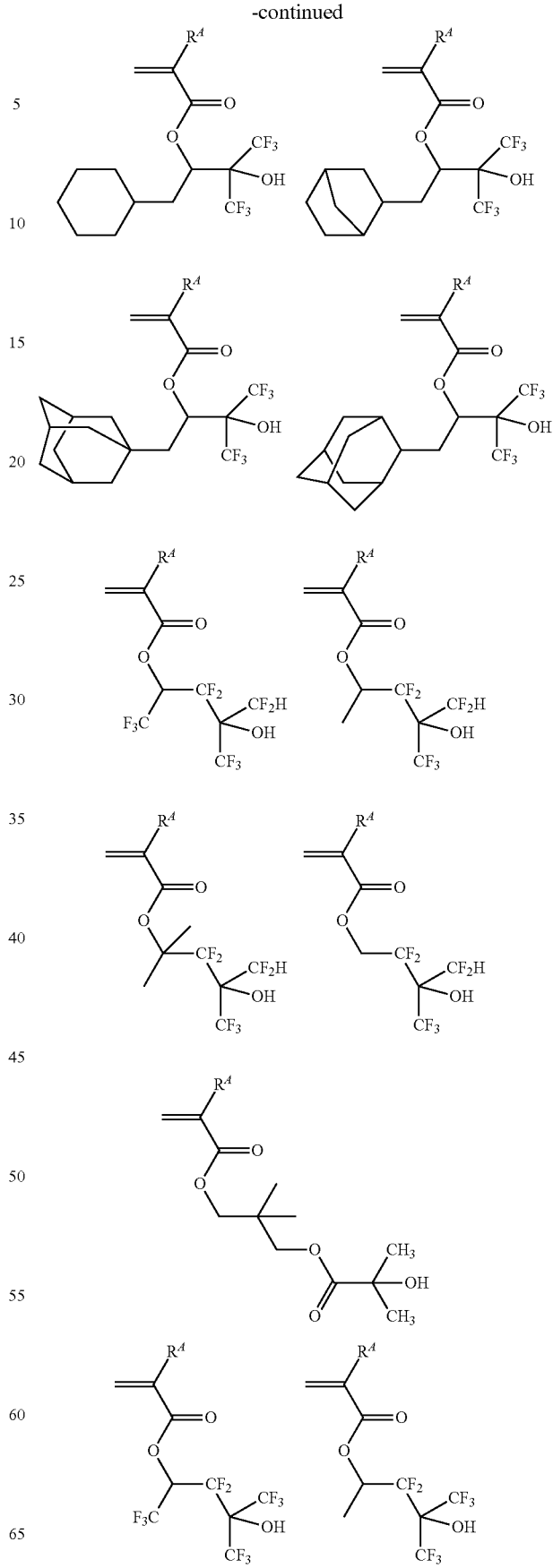

-continued
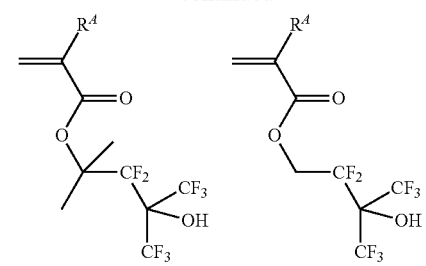
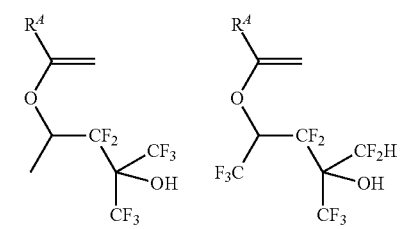
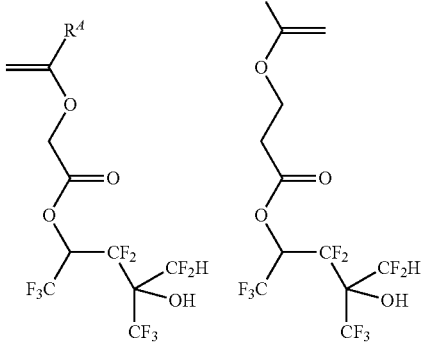
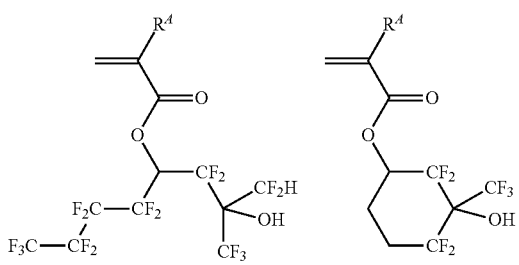
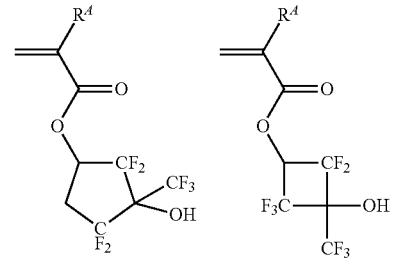
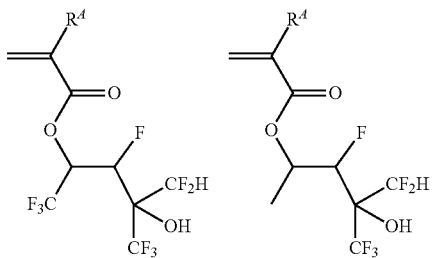
-continued
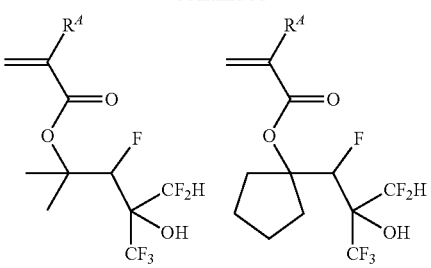
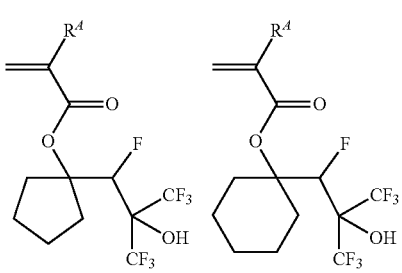
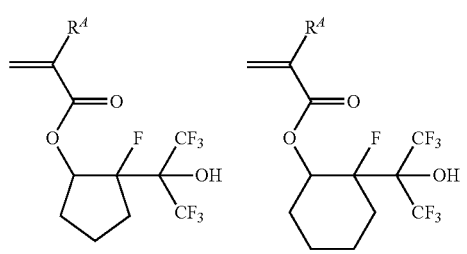
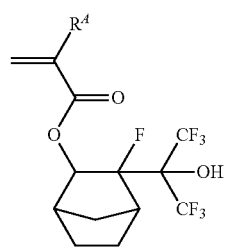
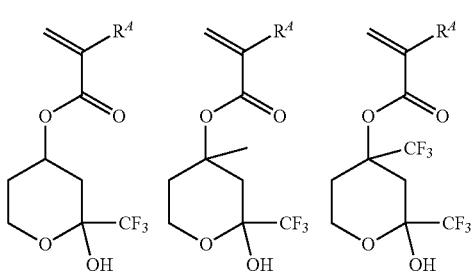
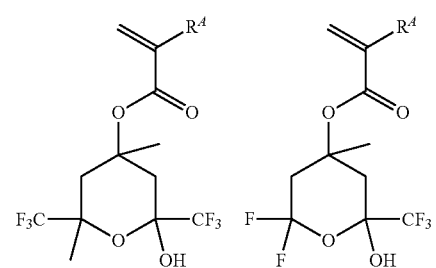

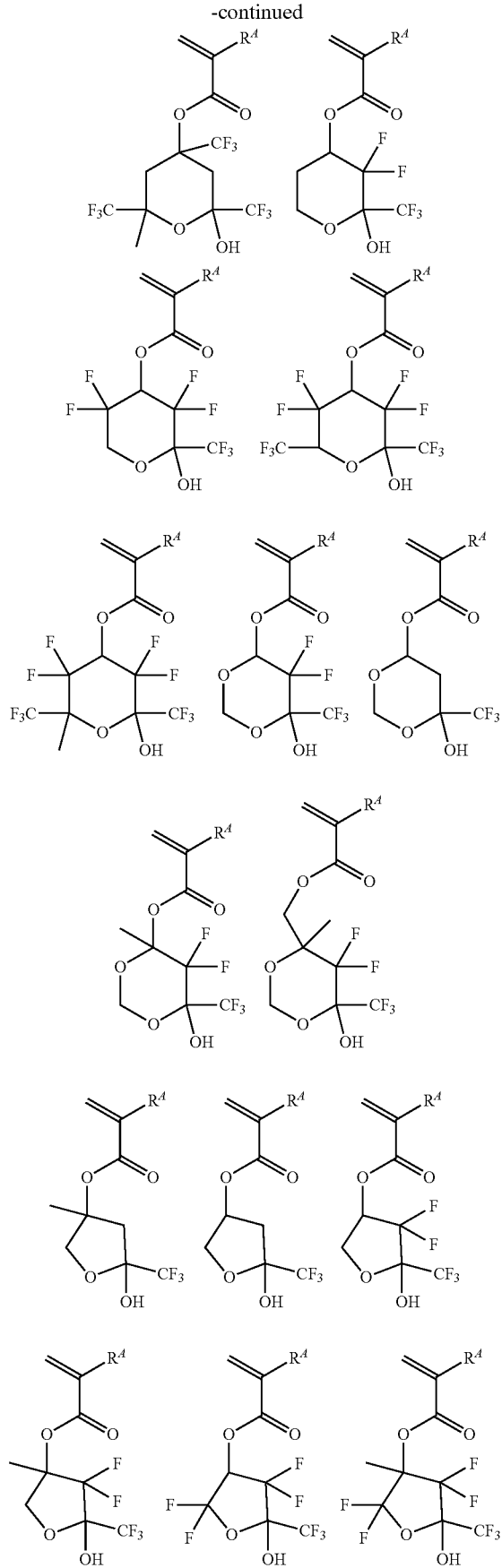
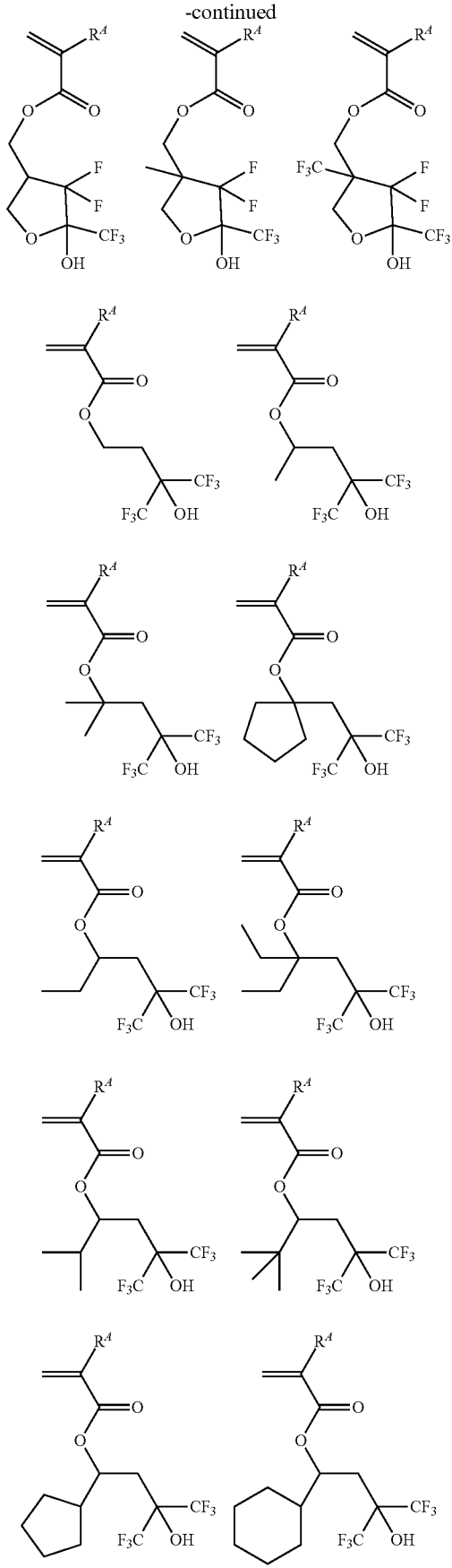

-continued
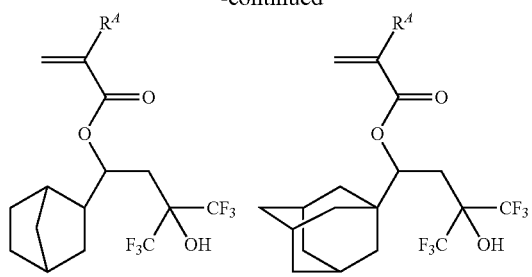
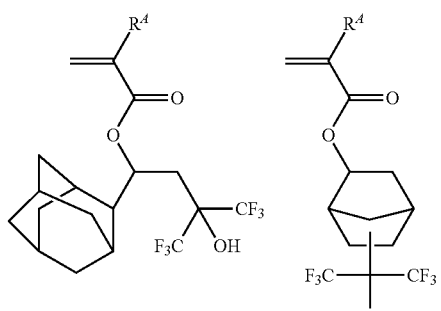
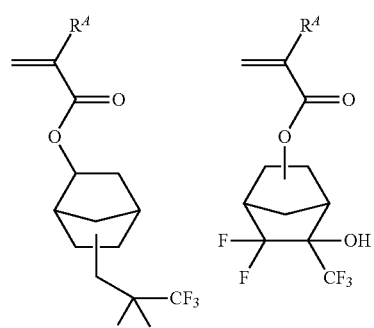
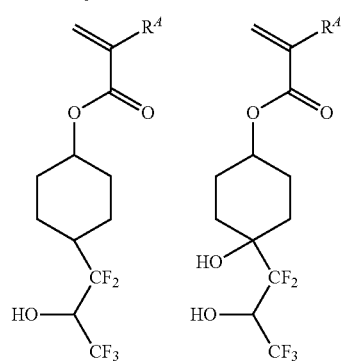
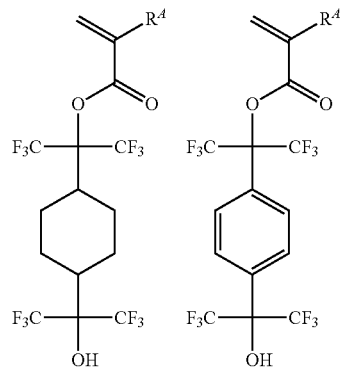
-continued
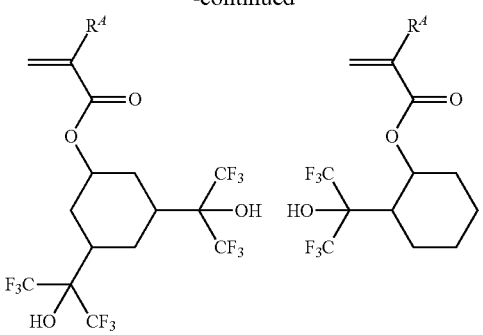
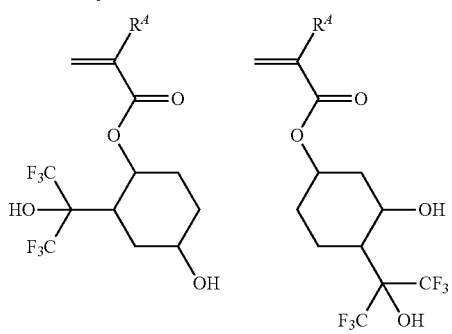
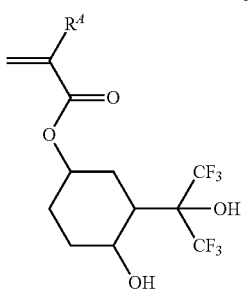
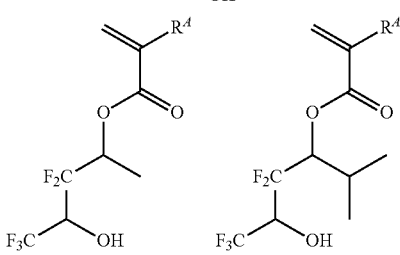
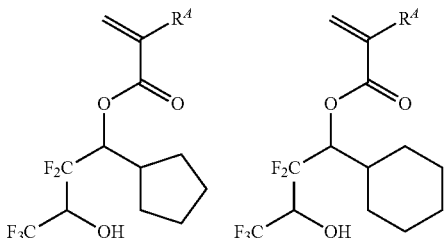
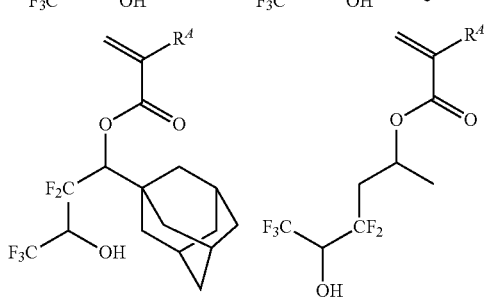

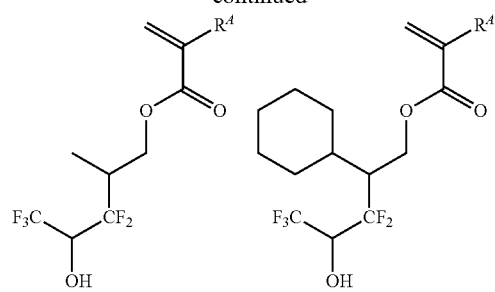
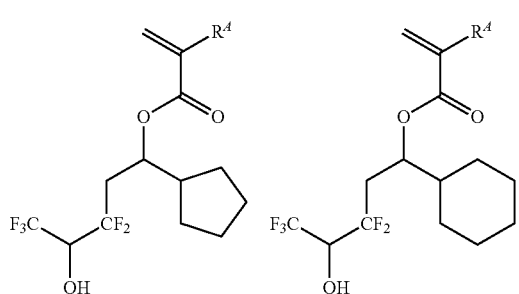
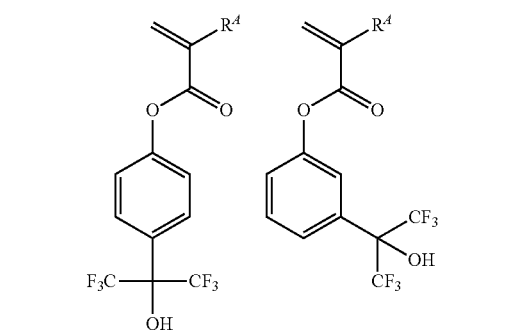
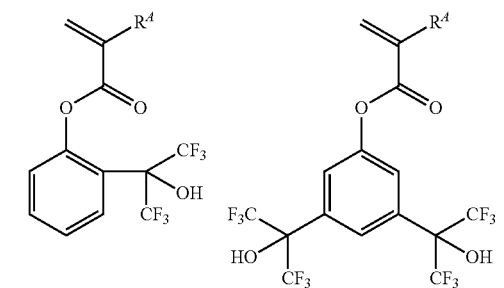
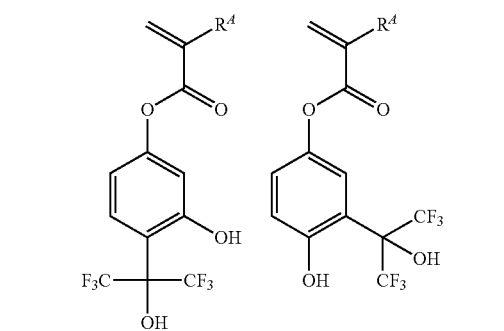
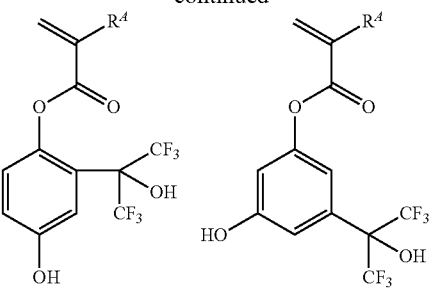
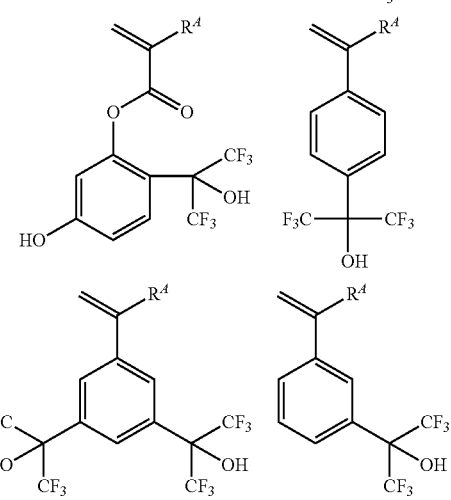
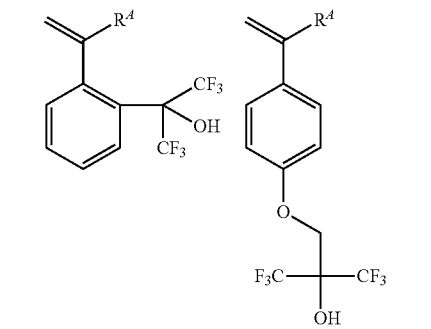
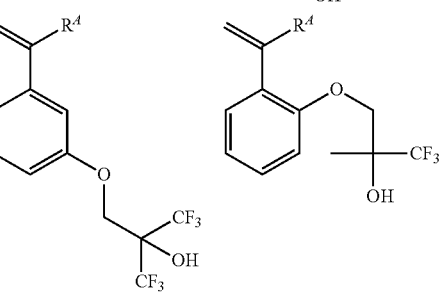
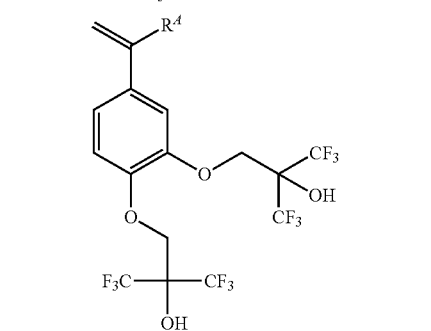

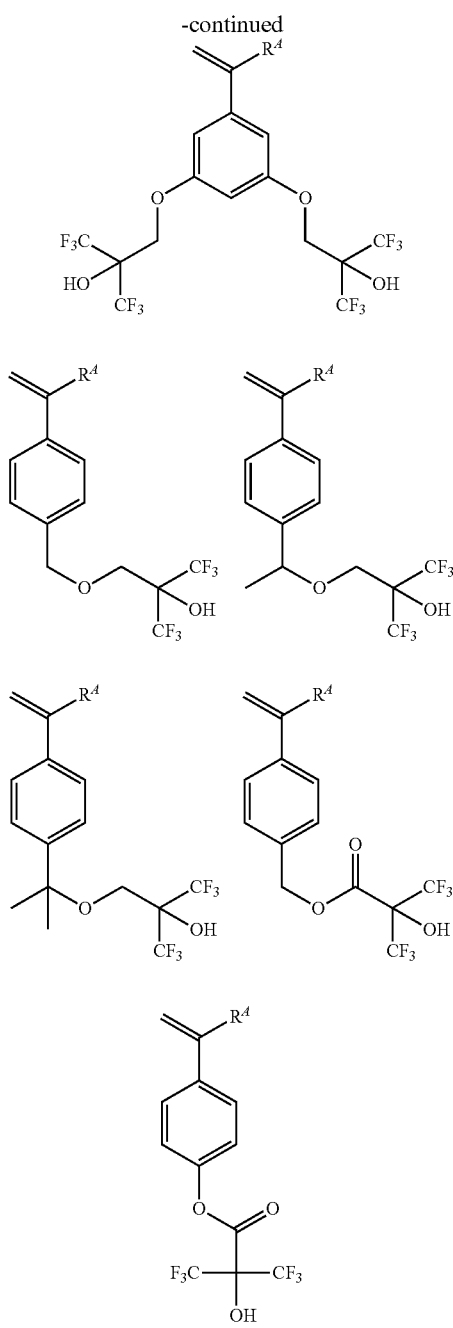
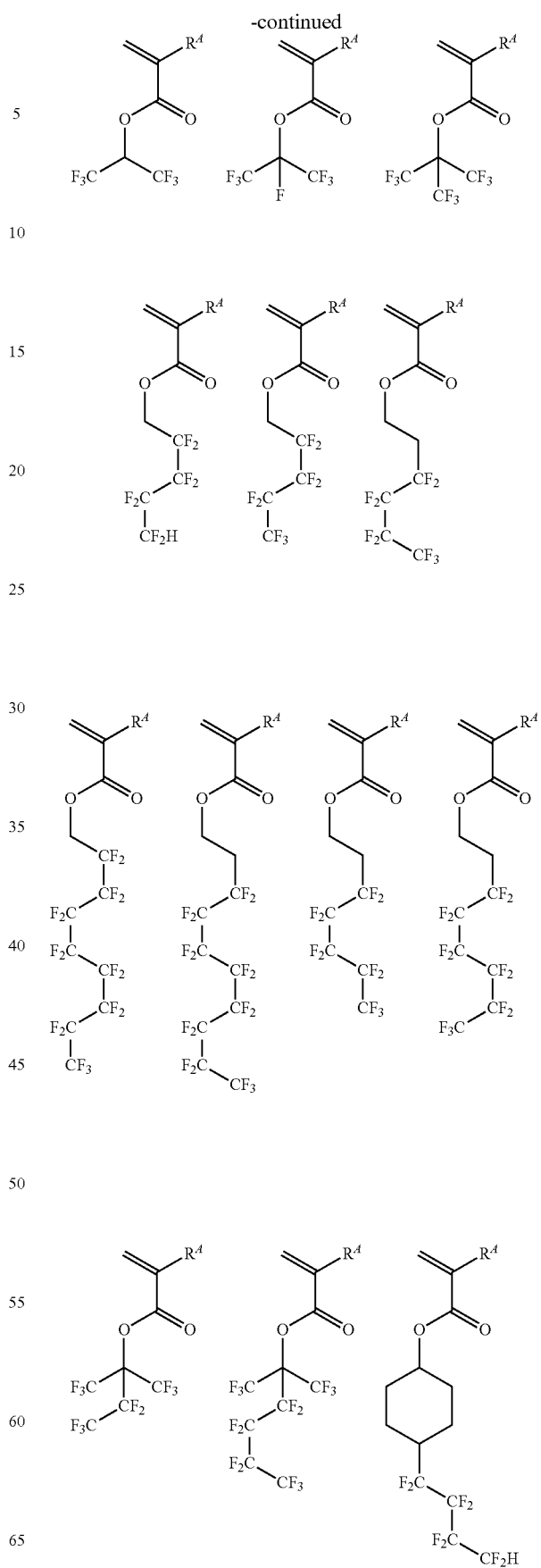
Examples of the monomer from which recurring units (C) are derived are shown below, but not limited thereto. Herein $R^A$ is as defined above.
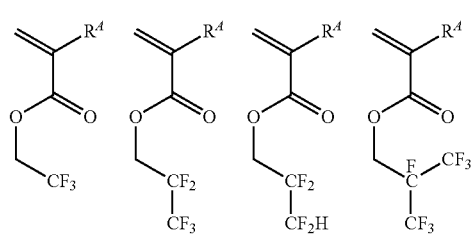
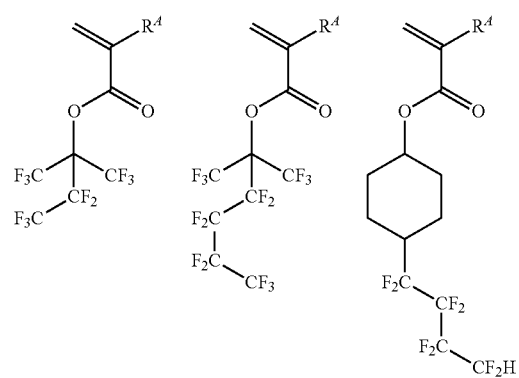

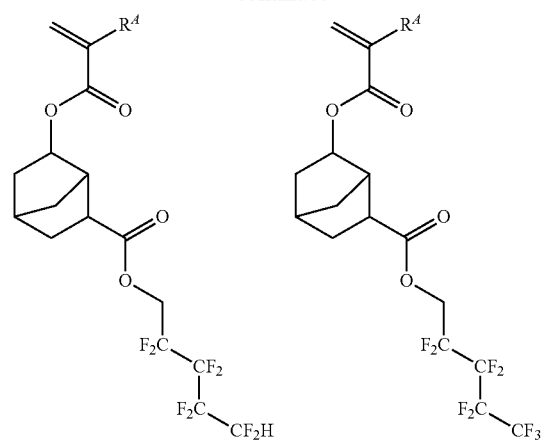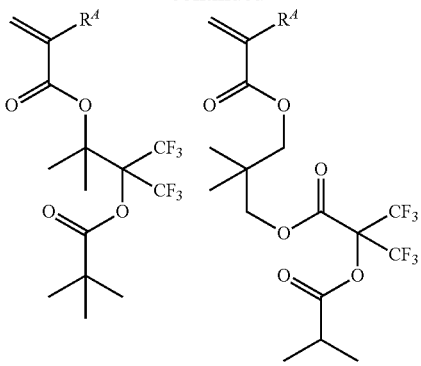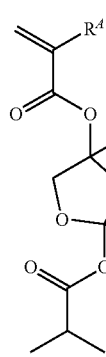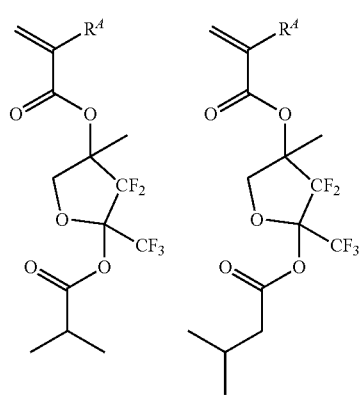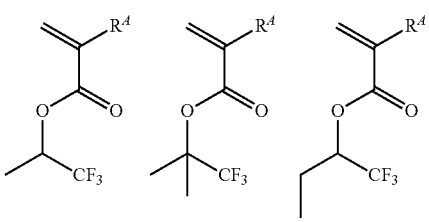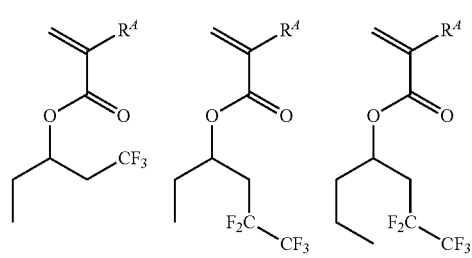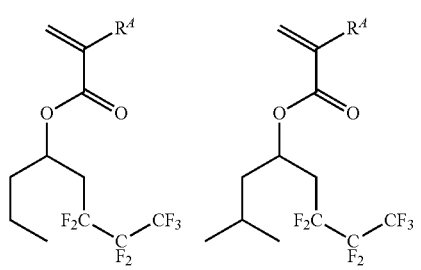

27
-continued
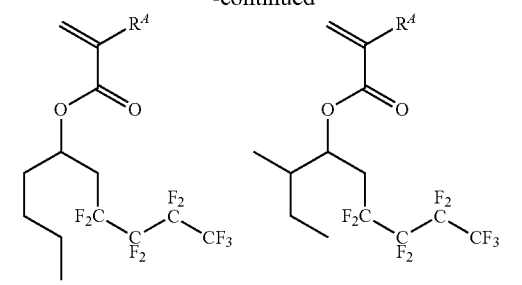
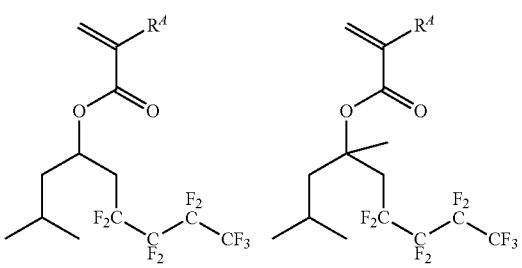
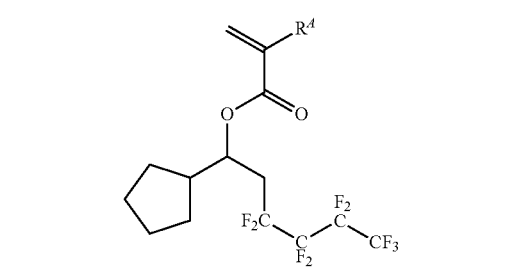
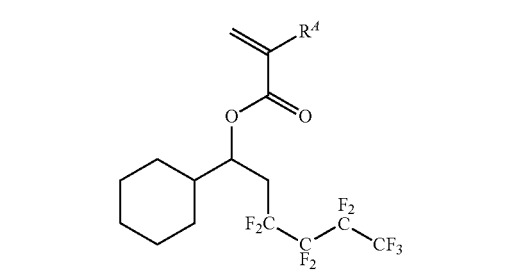
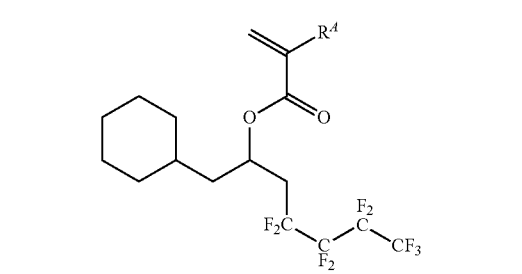
28
-continued
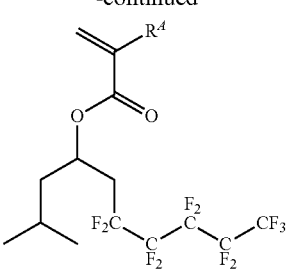
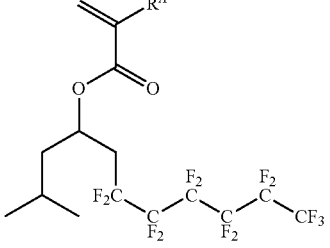
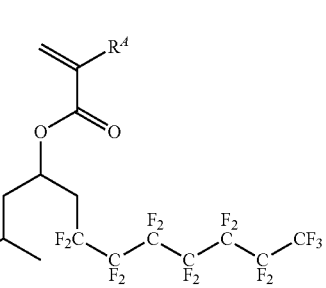
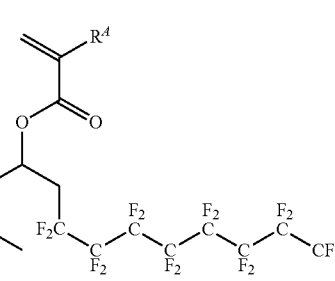
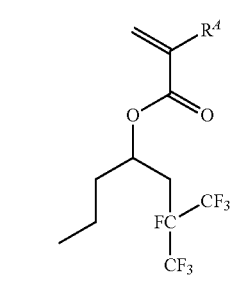
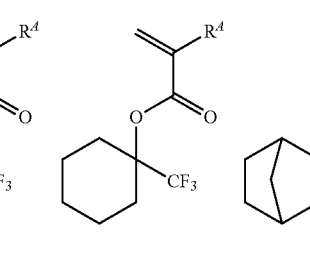

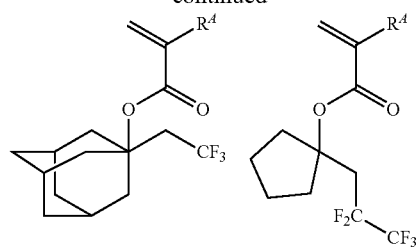
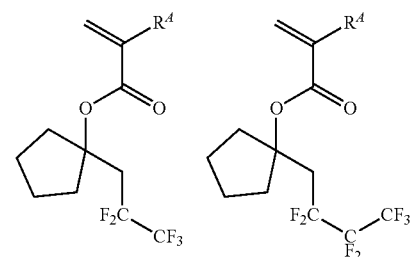
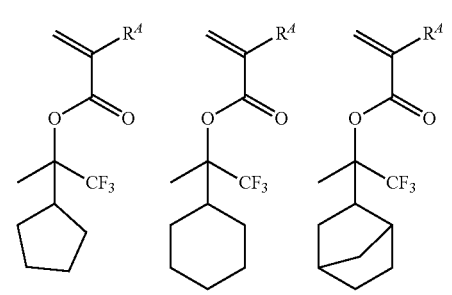
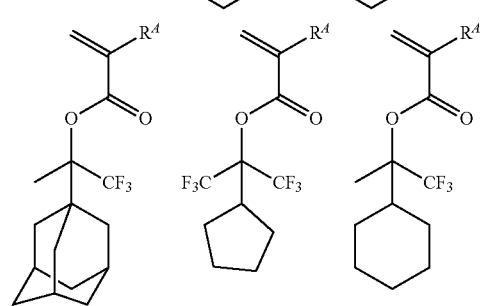
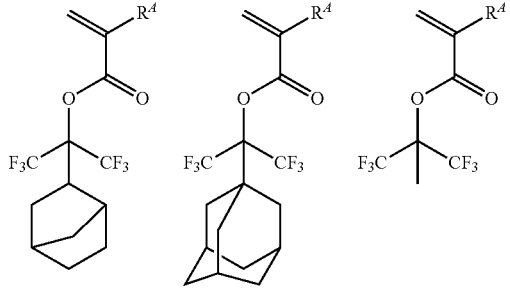
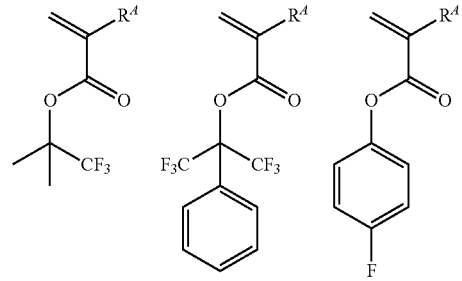
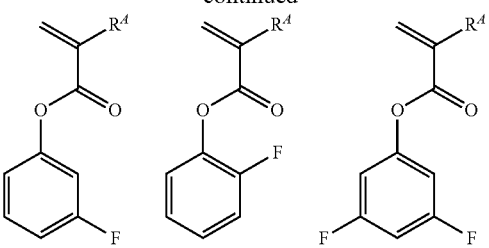
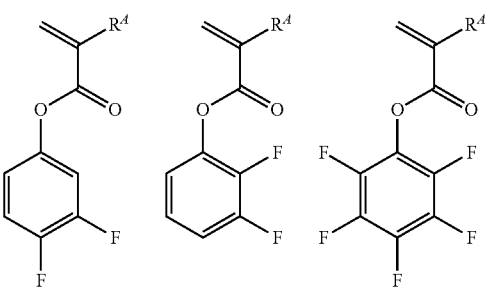
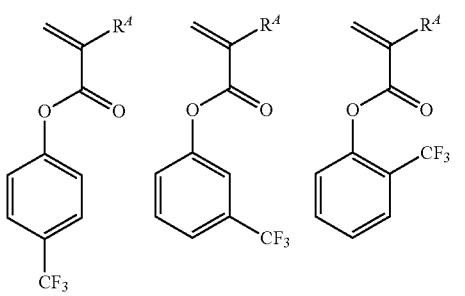
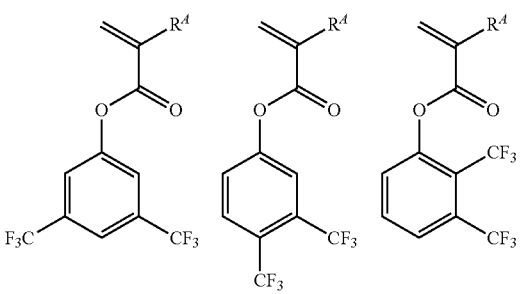
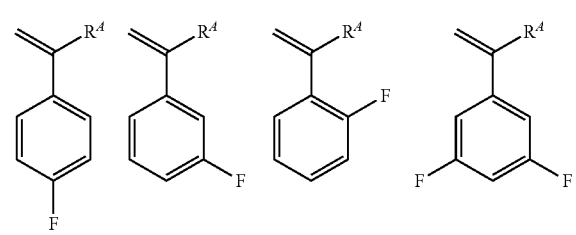
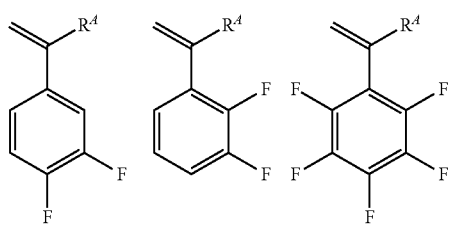

-continued

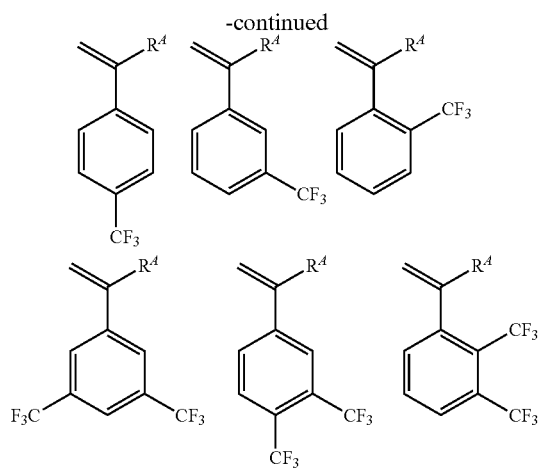

The fraction of recurring units (A), (B) and (C) is preferably 0<A≤1.0, 0≤B<1.0, 0≤C<1.0, and 0≤B+C<1.0; more preferably 0.05≤A≤0.9, 0≤B≤0.95, 0≤C≤0.95, and 0.1≤B+C≤0.95; even more preferably 0.1≤A≤0.8, 0≤B≤0.8, 0≤C≤0.8, and 0.2≤B+C≤0.9. Although the fluorocarboxylic acid-containing polymer may further comprise other recurring units exclusive of acid labile group-containing recurring units as long as the benefits of the invention are not compromised, it is preferred that the polymer do not include other units (i.e., A+B+C=1).

The fluorocarboxylic acid-containing polymer preferably has a weight average molecular weight (Mw) of 1,000 to 1,000,000, more preferably 2,000 to 100,000. Also, the polymer preferably has a molecular weight distribution (Mw/Mn) of 1.0 to 3.0. Notably, Mw and Mn are as measured by gel permeation chromatography (GPC) using tetrahydrofuran (THF) solvent versus polystyrene standards.

Resist Composition

A further embodiment of the invention is a resist composition comprising the fluorocarboxylic acid-containing polymer and a base polymer. After a resist film is formed from the composition, the fluorocarboxylic acid-containing polymer segregates on the resist film surface to improve the solubility thereof in alkaline developer for thereby preventing bridge defects between pattern features and pattern collapse.

In the resist composition, it is preferred in view of sensitivity and acid diffusion suppressing effect that the amount of the fluorocarboxylic acid-containing polymer be 0.001 to 20 parts by weight, more preferably 0.01 to 10 parts by weight per 100 parts by weight of the base polymer.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

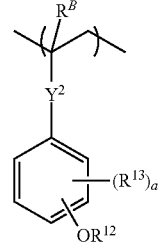
(a1)

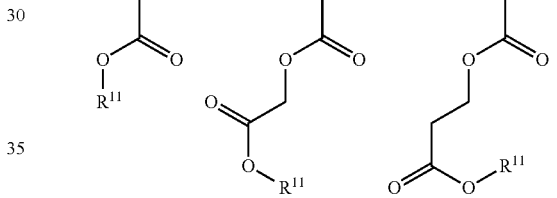
(a2)

In formulae (a1) and (a2), $R^B$ is each independently hydrogen or methyl. $R^{11}$ and $R^{12}$ each are an acid labile group. $R^{13}$ is fluorine, trifluoromethyl, a $C_1$-$C_5$ saturated hydrocarbyl group or $C_1$-$C_5$ saturated hydrocarbyloxy group. $Y^1$ is a single bond, phenylene or naphthylene group, or $C_1$-$C_{12}$ linking group containing an ester bond and/or lactone ring. $Y^2$ is a single bond or ester bond. The subscript "a" is an integer of 0 to 4.

Examples of the monomer from which the recurring units (a1) are derived are shown below, but not limited thereto. $R^B$ and $R^{11}$ are as defined above.

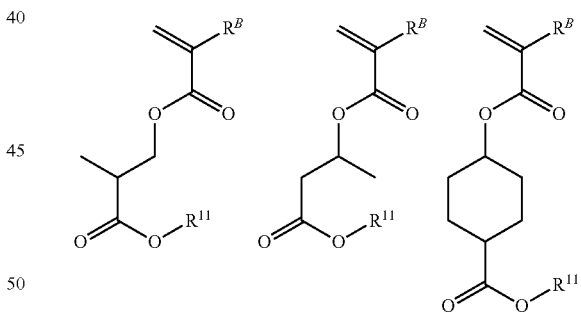

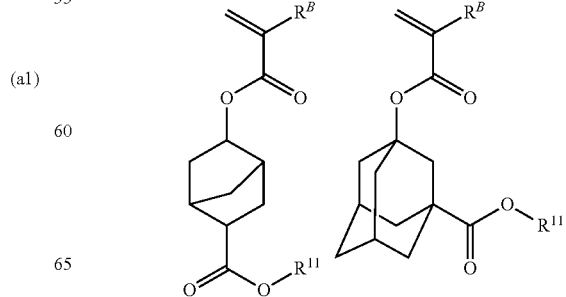

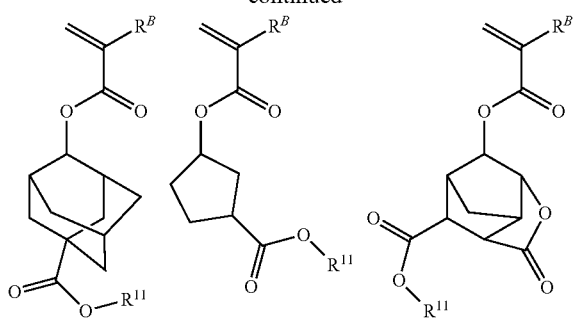

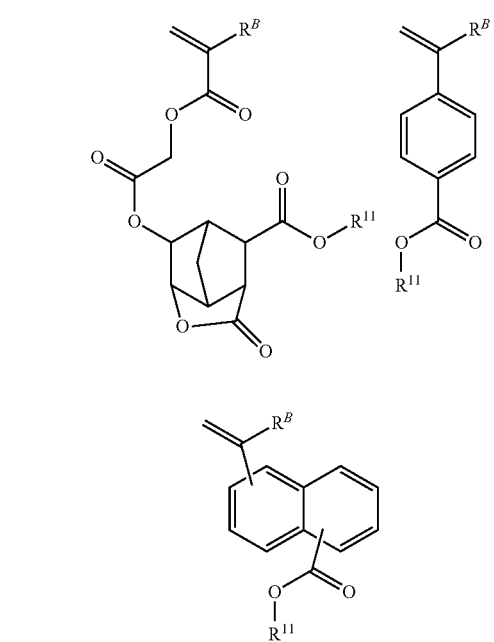

Examples of the monomer from which the recurring units (a2) are derived are shown below, but not limited thereto. $R^B$ and $R^{12}$ are as defined above.

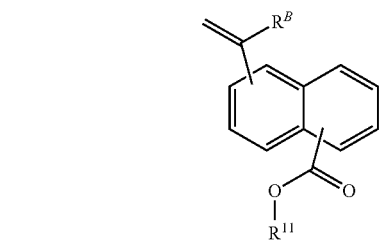

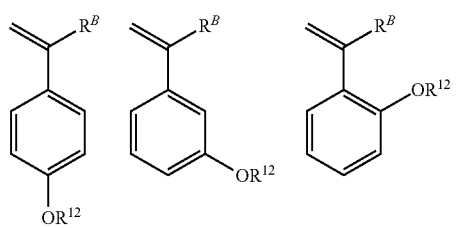

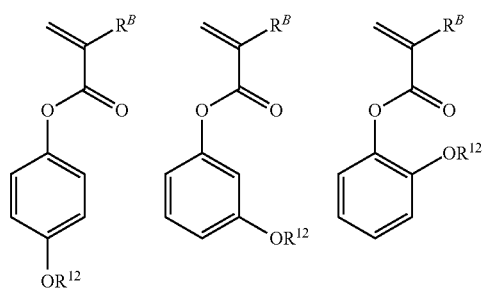

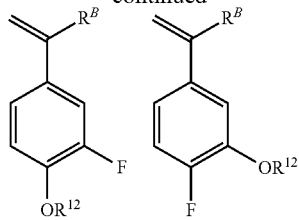

The acid labile groups represented by $R^{11}$ in formula (a1) and $R^{12}$ in formula (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

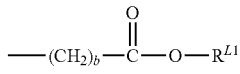 (AL-1)

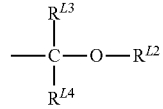 (AL-2)

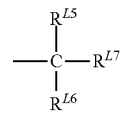 (AL-3)

Herein the broken line designates a valence bond.

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter aha, $C_1$-$C_{40}$ saturated hydrocarbyl groups are preferred, and $C_1$-$C_{20}$ saturated hydrocarbyl groups are more preferred.

In formula (AL-1), b is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$, and $R^{L4}$ bond together to form a $C_3$-$C_{20}$ ring with the carbon atom or carbon and oxygen atoms to which they are attached, the ring being preferably of 4 to 16 carbon atoms and especially alicyclic.

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter aha, $C_1$-$C_{20}$ saturated hydrocarbyl groups are preferred. Any two of $R^{L5}$, $R^{L6}$ and $R^{L7}$ may bond together to form a $C_3$-$C_{20}$ ring with the carbon atom to which they are attached, the ring being preferably of 4 to 16 carbon atoms and especially alicyclic.

The base polymer may further comprise recurring units (b) having a phenolic hydroxyl group as an adhesive group. Examples of suitable monomers from which recurring units (b) are derived are given below, but not limited thereto. Herein $R^B$ is as defined above.

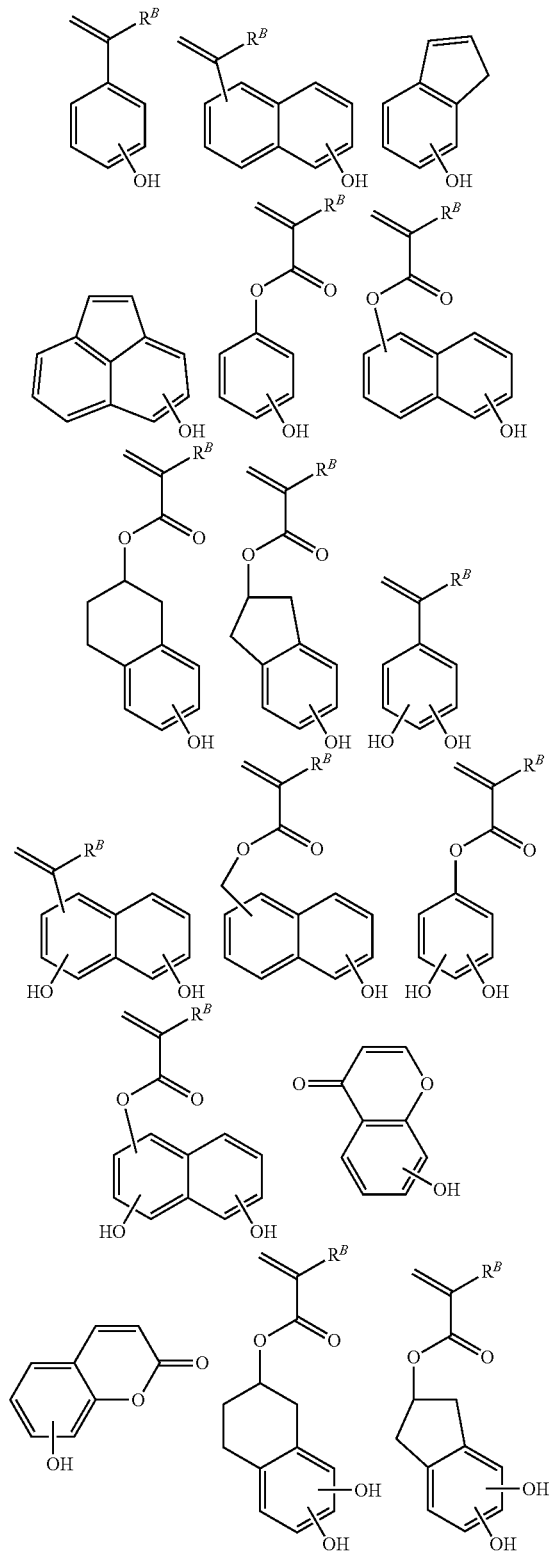

Further, recurring units (c) having another adhesive group selected from hydroxyl (other than the foregoing phenolic hydroxyl), lactone ring, ether bond, ester bond, carbonyl, cyano and carboxyl groups may also be incorporated in the base polymer. Examples of suitable monomers from which recurring units (c) are derived are given below, but not limited thereto. Herein $R^B$ is as defined above.

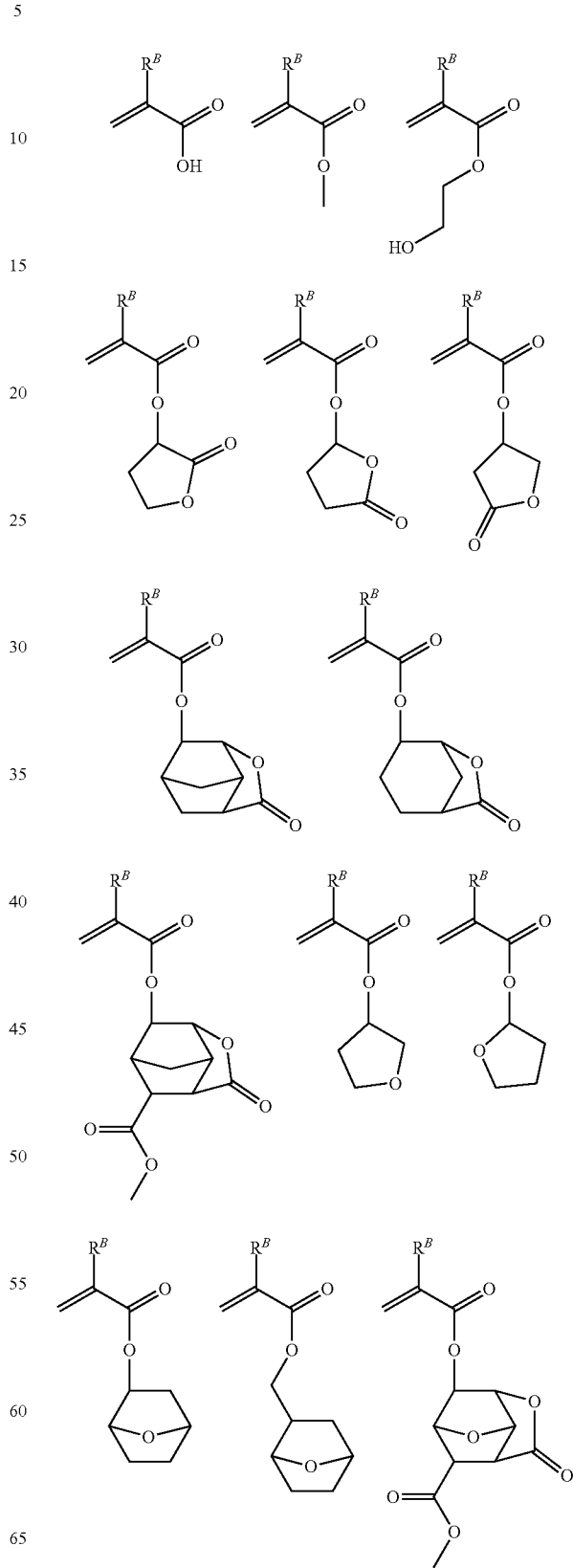

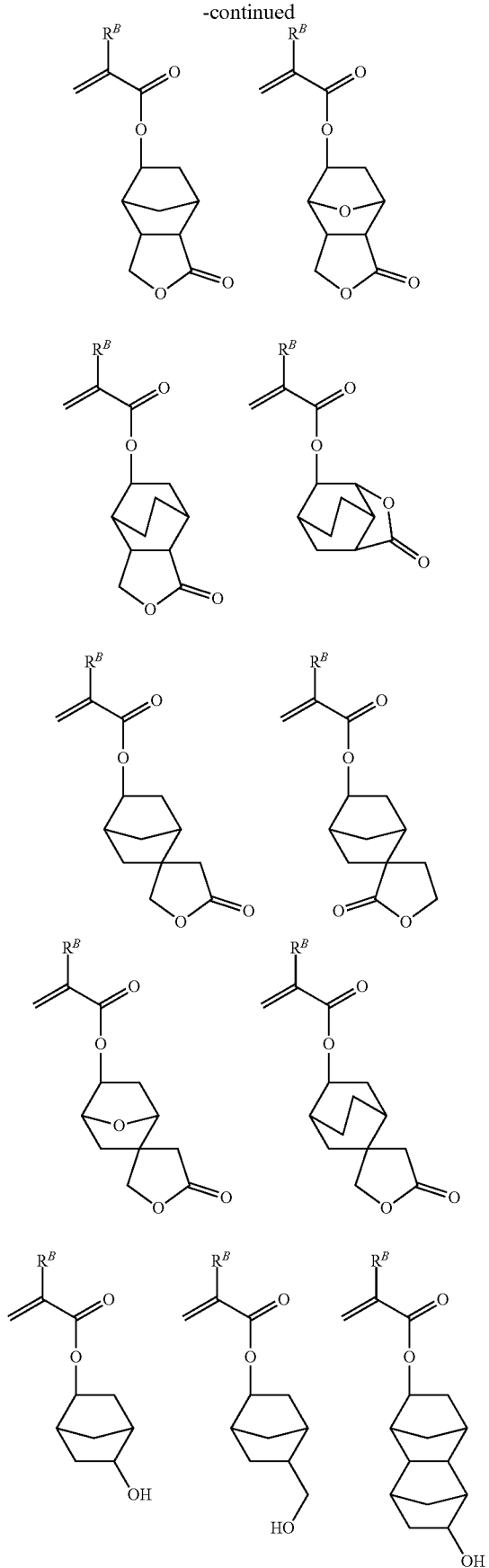
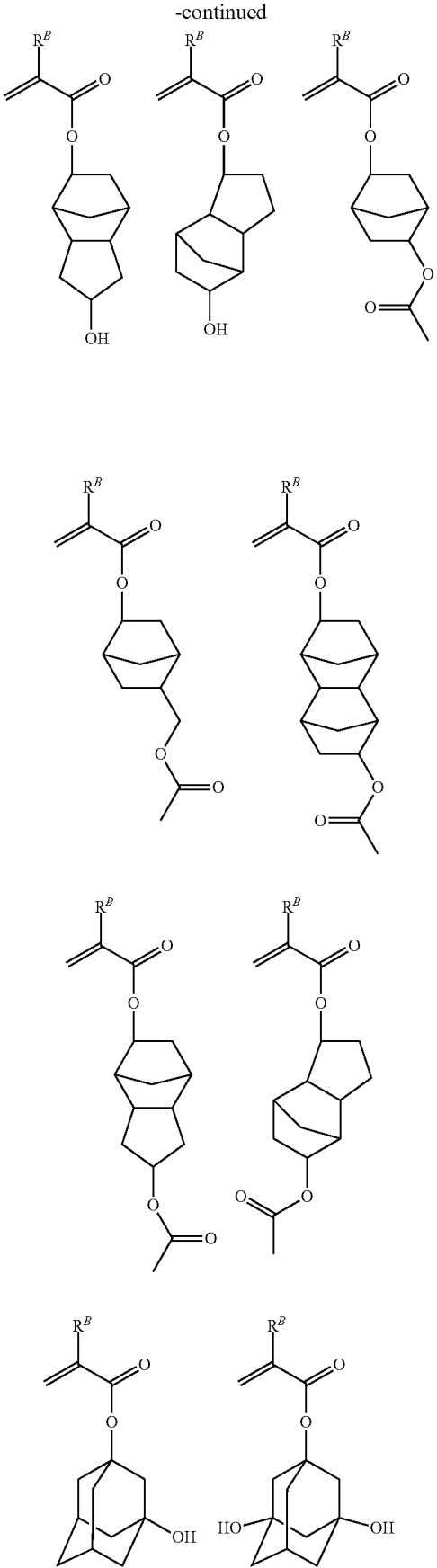

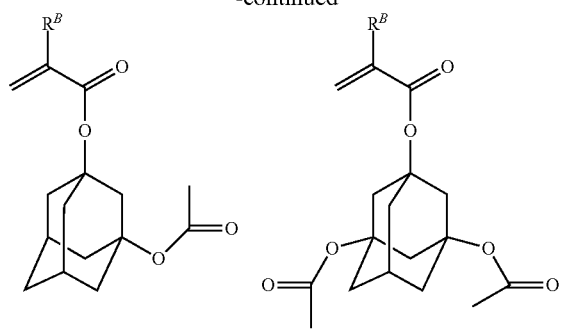
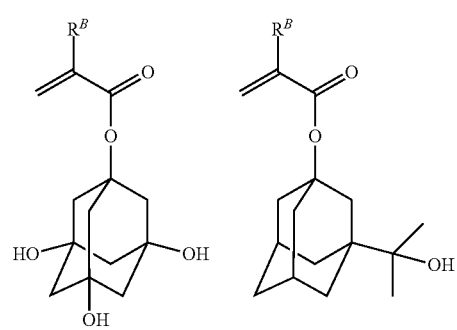
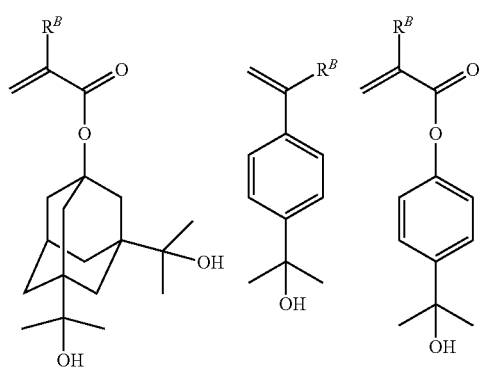
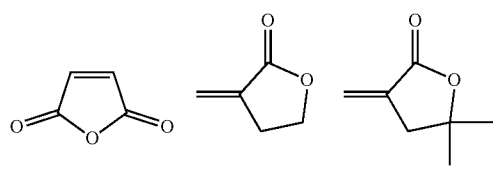
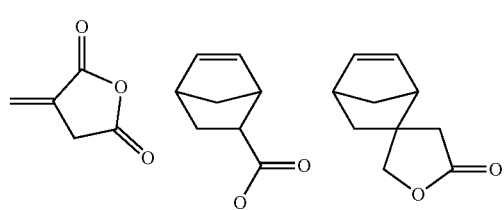
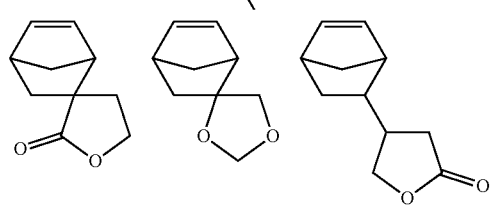
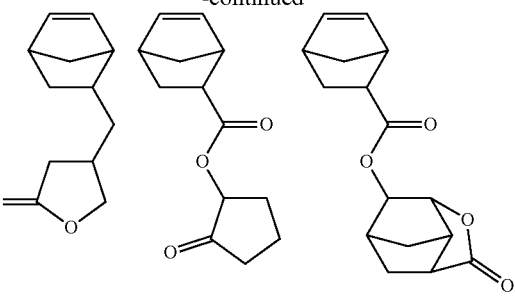
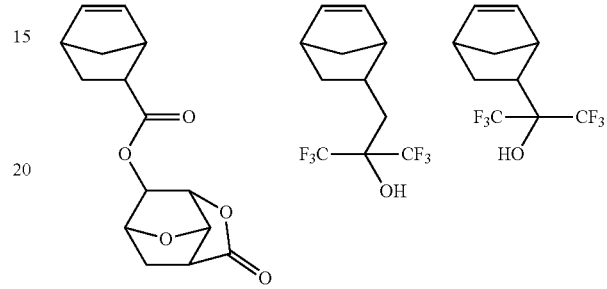
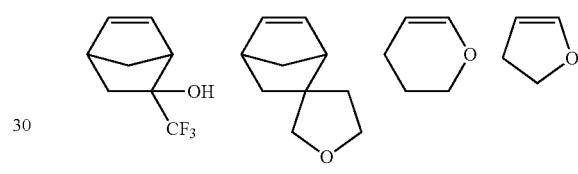
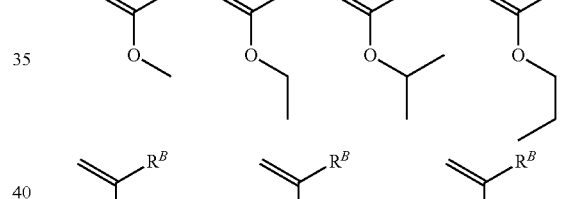
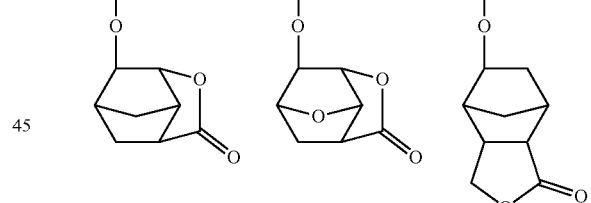
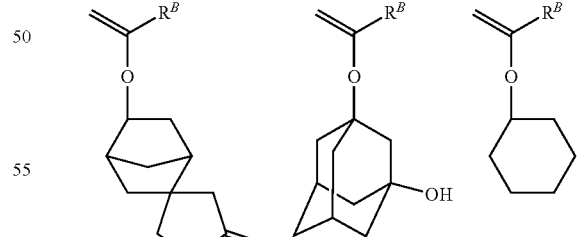
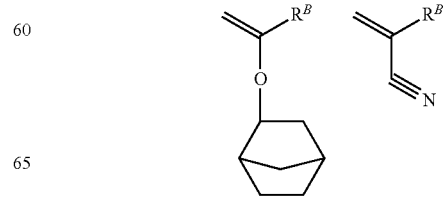

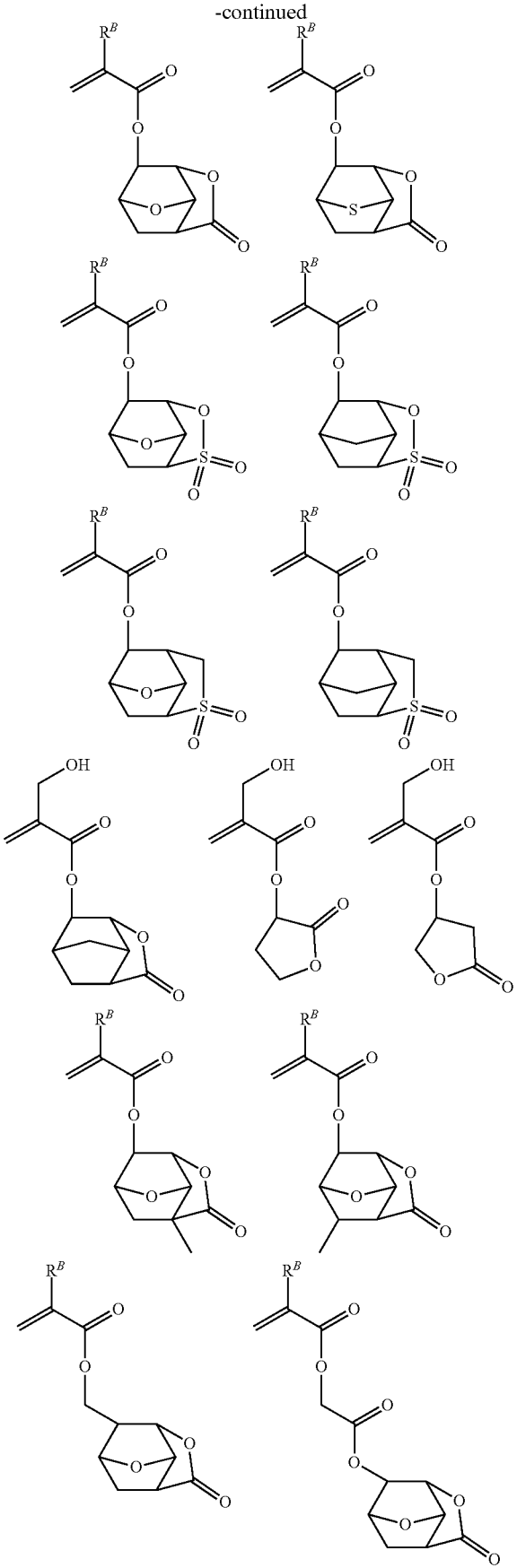
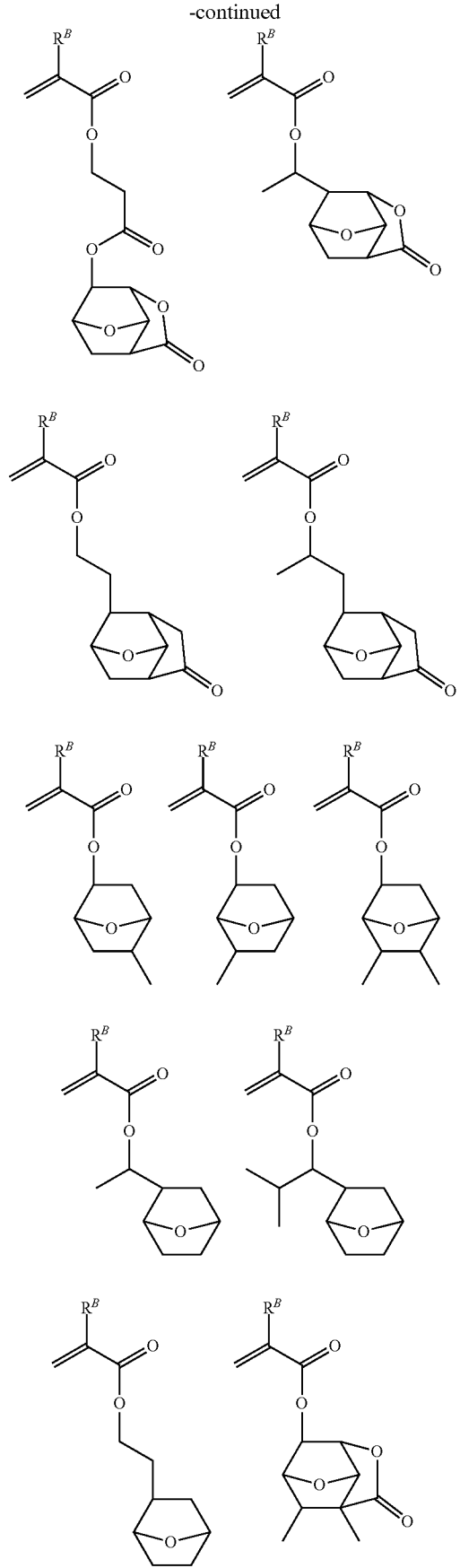

-continued
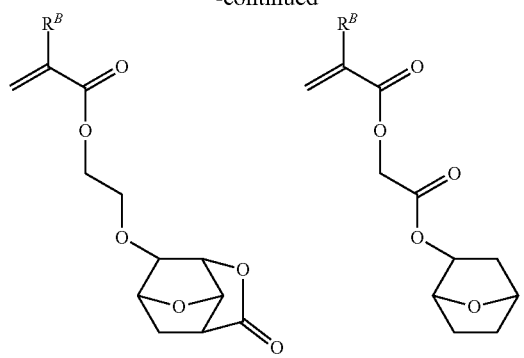
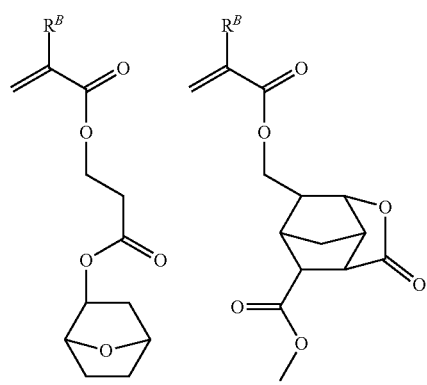
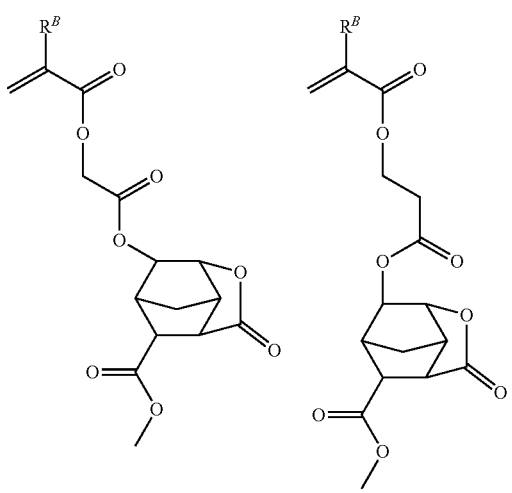
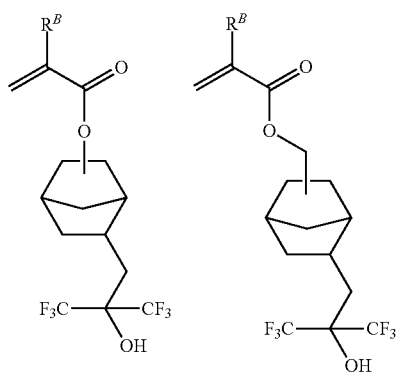
-continued
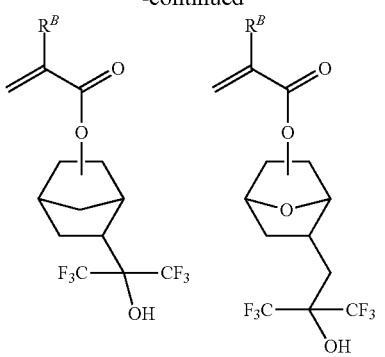
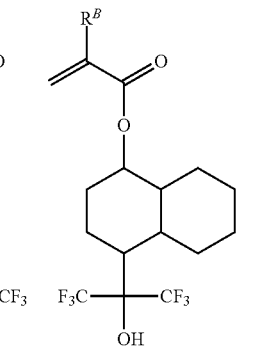
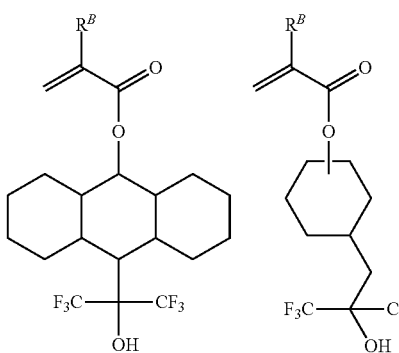
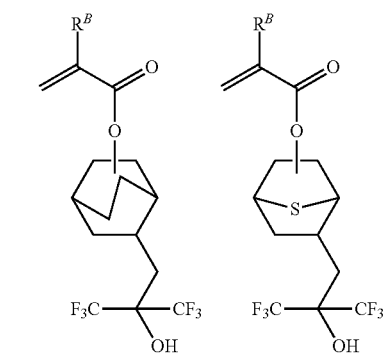

-continued
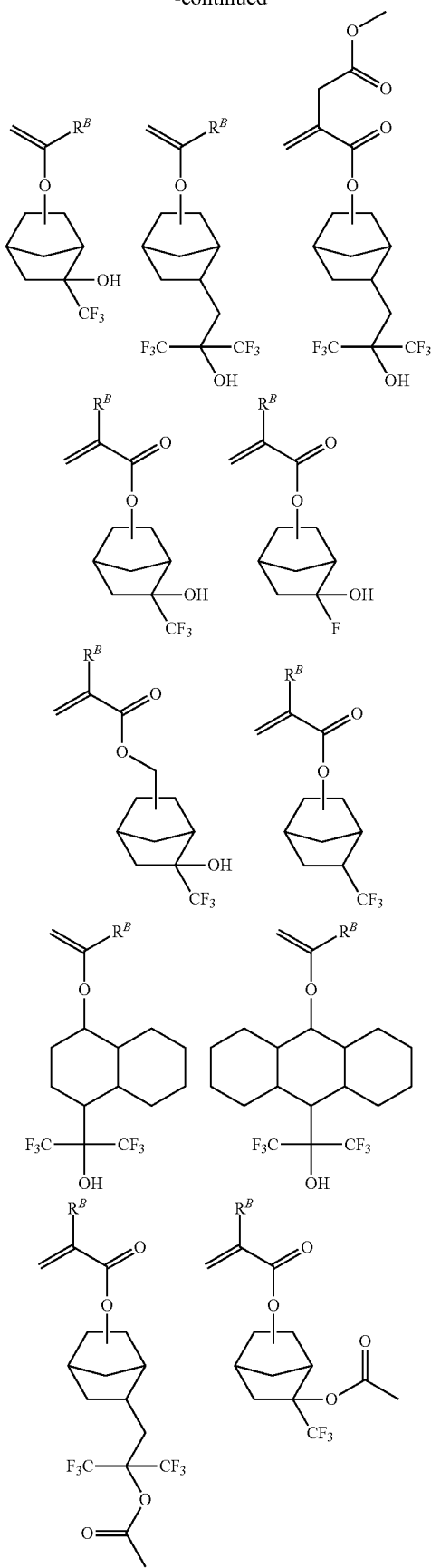
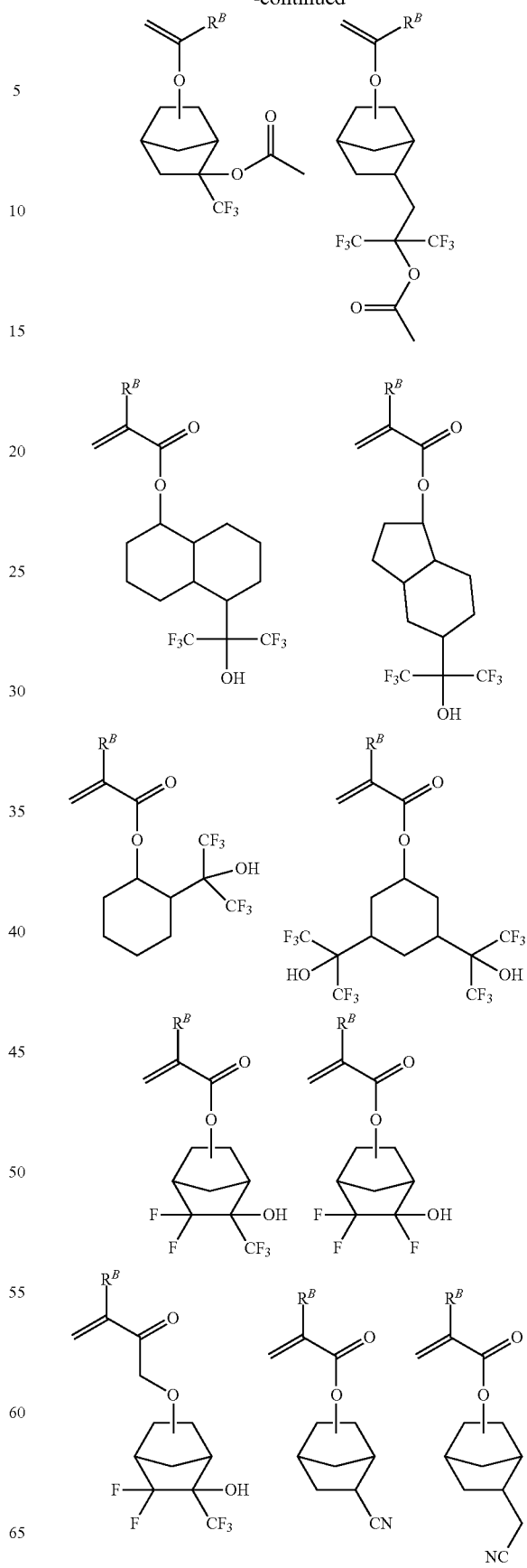

-continued
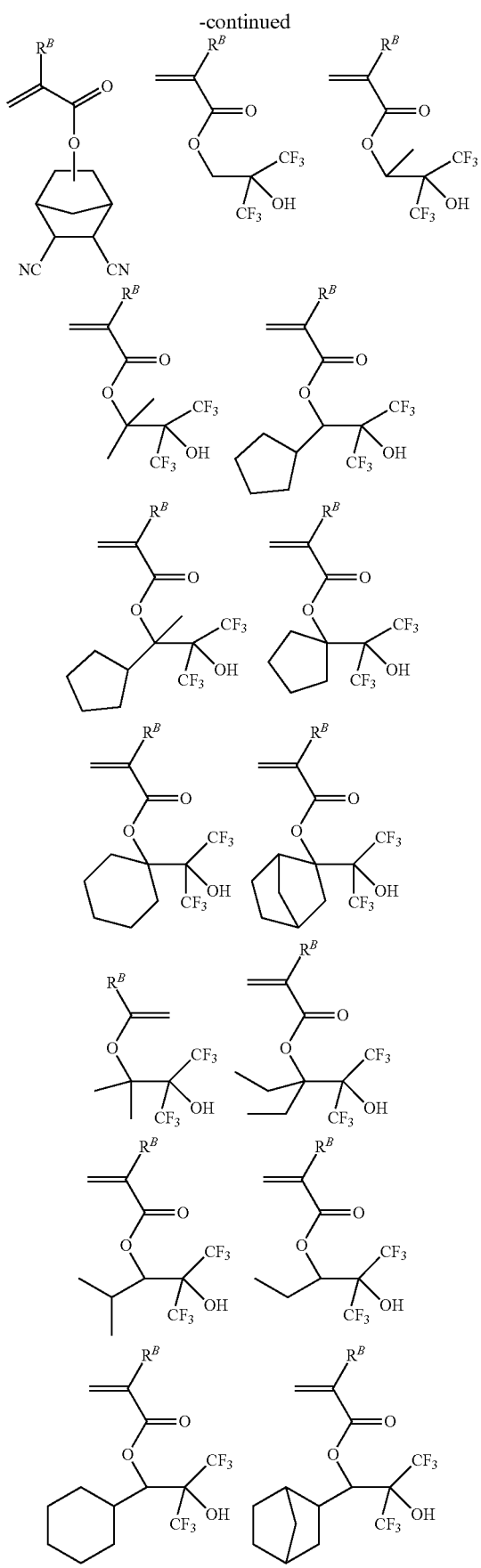
-continued
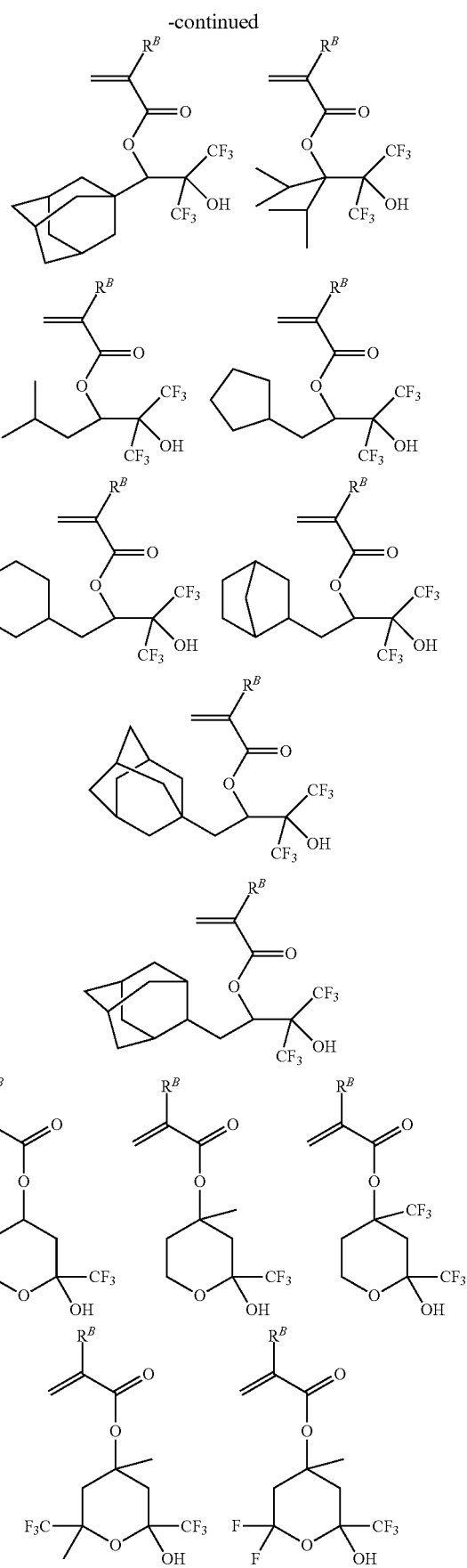

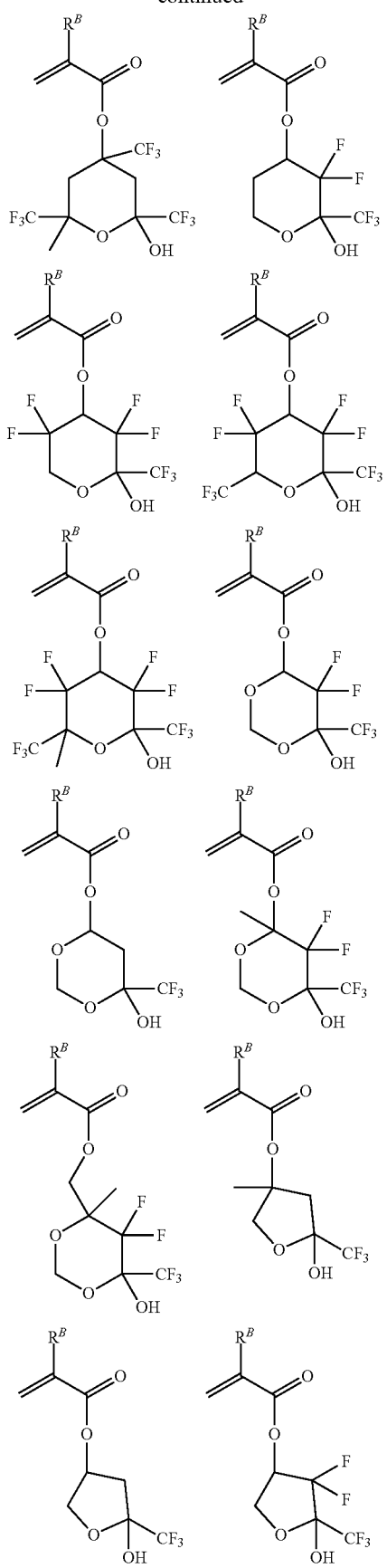
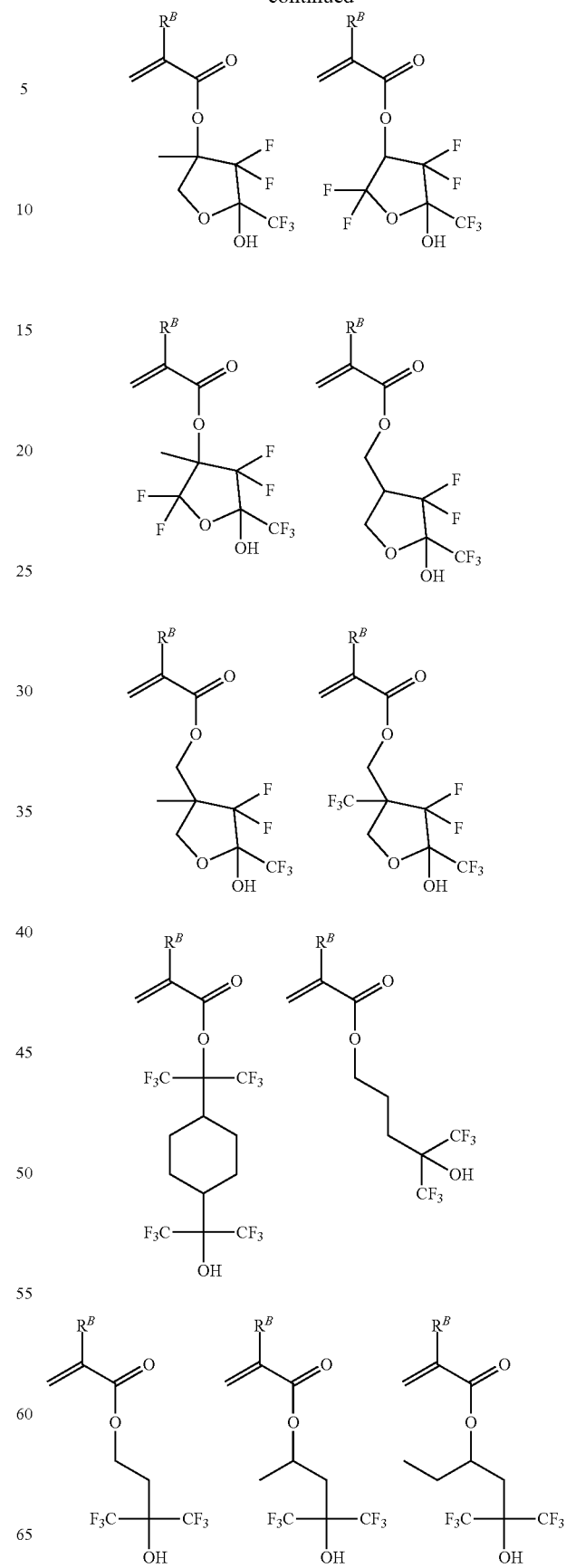

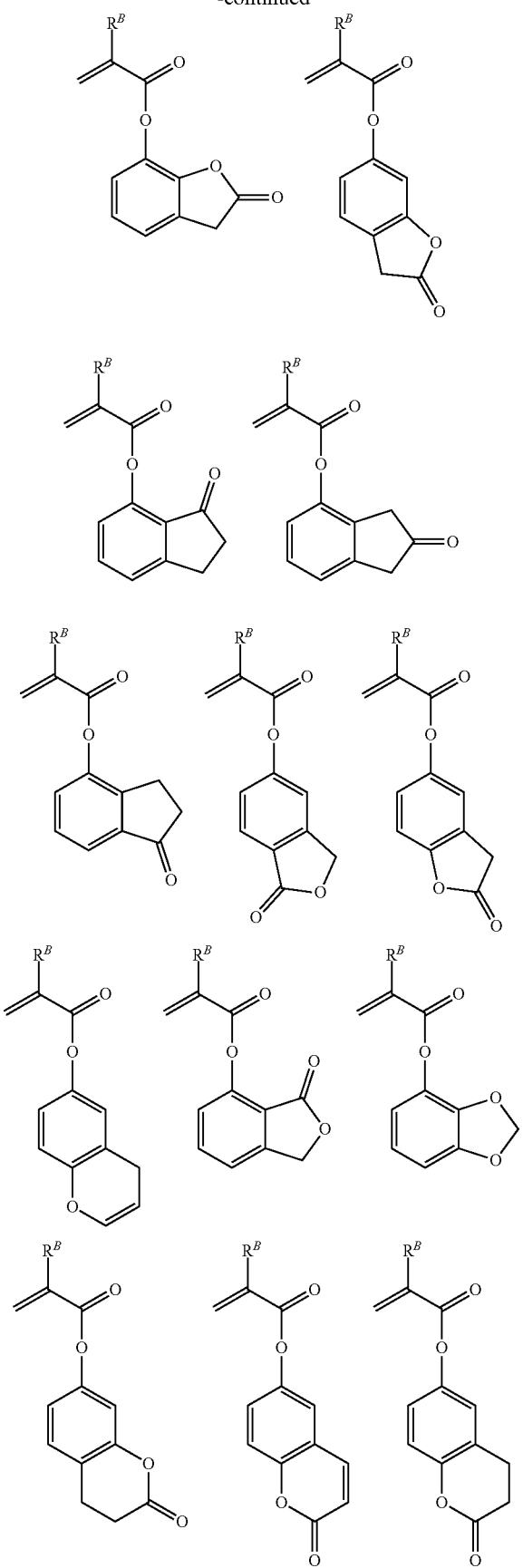
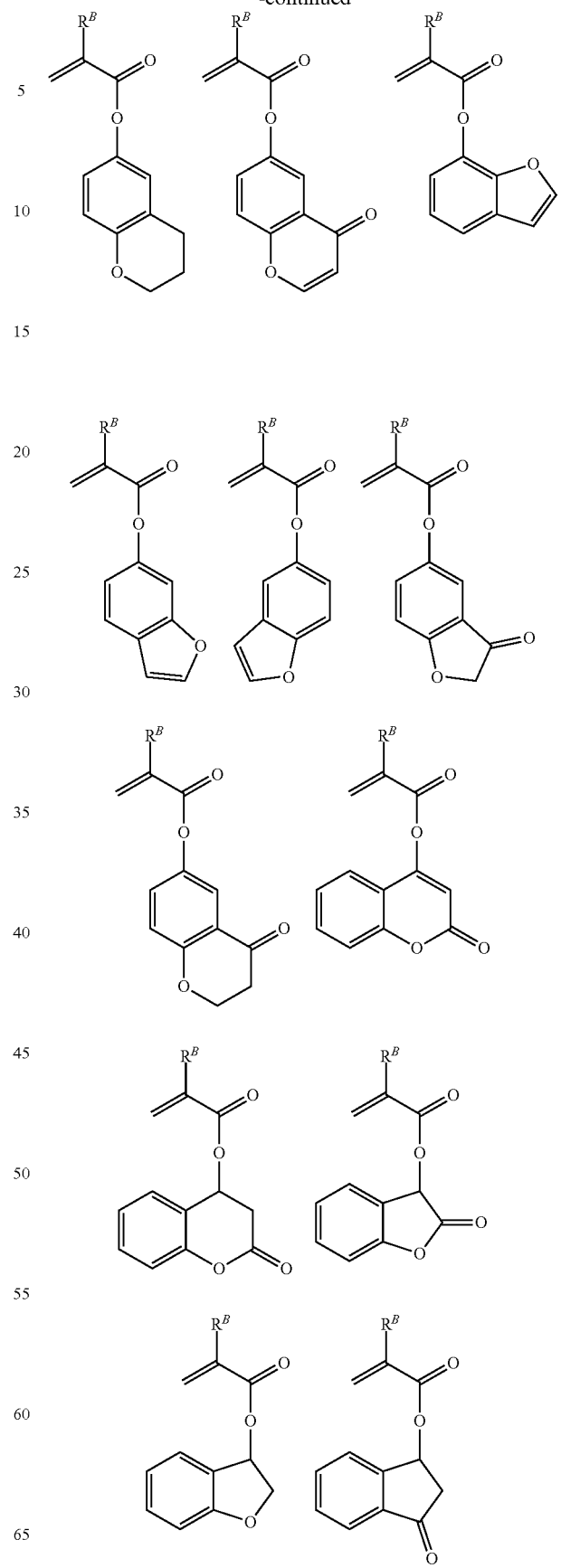

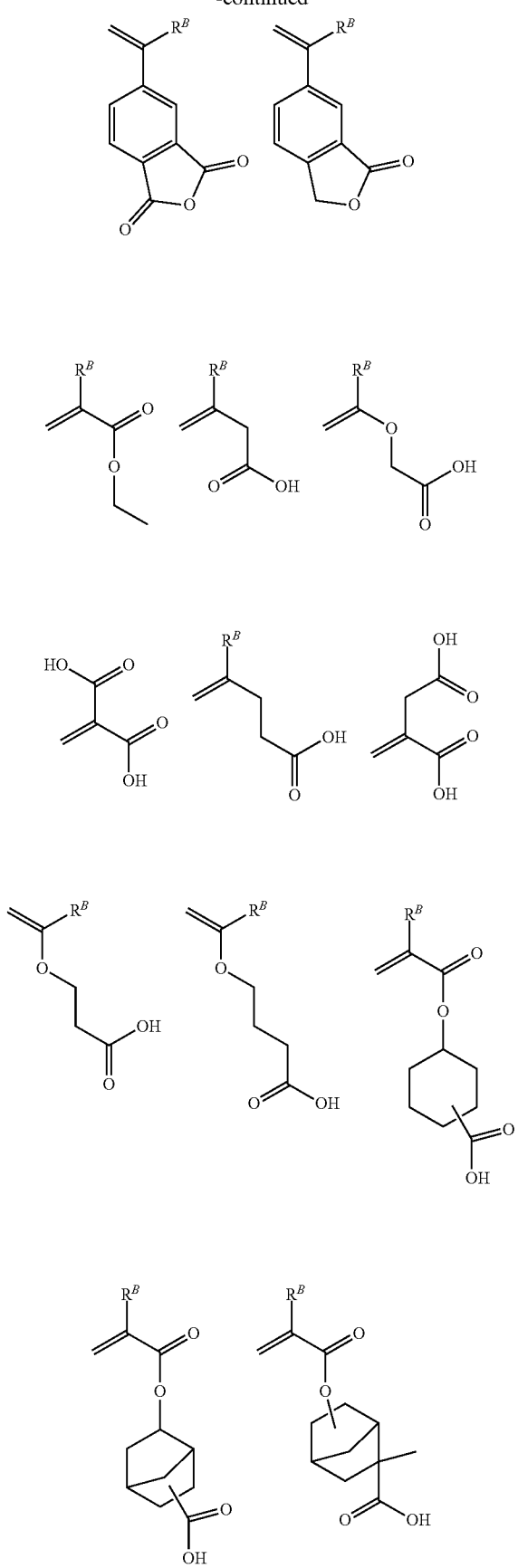
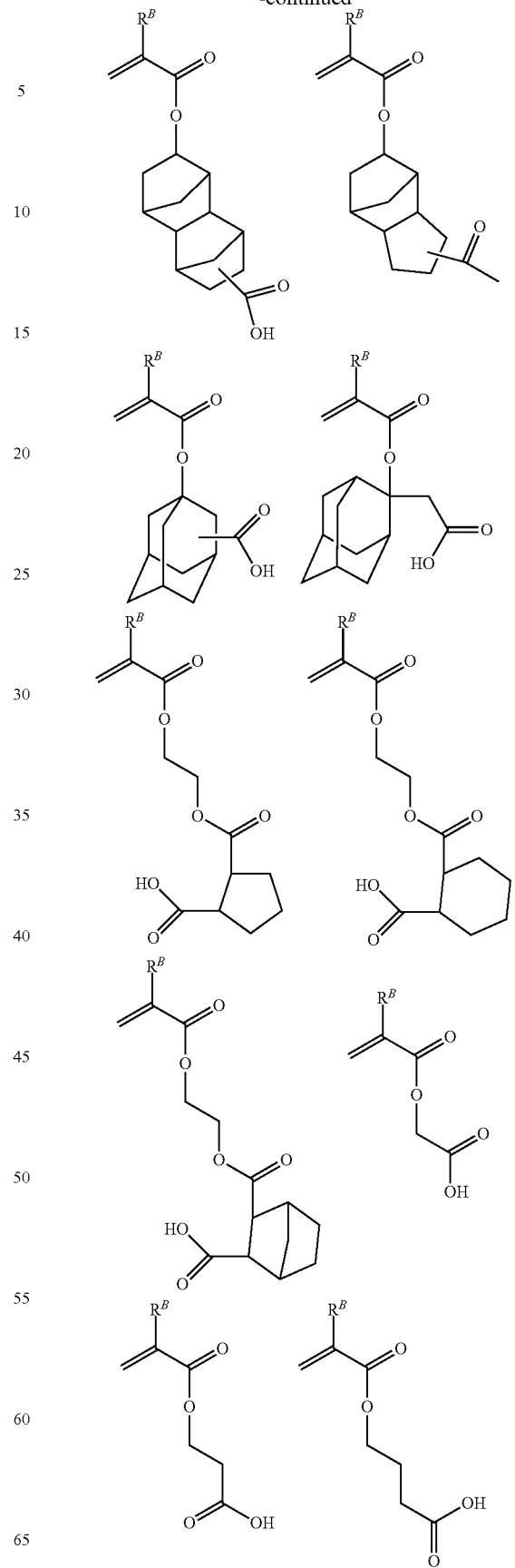

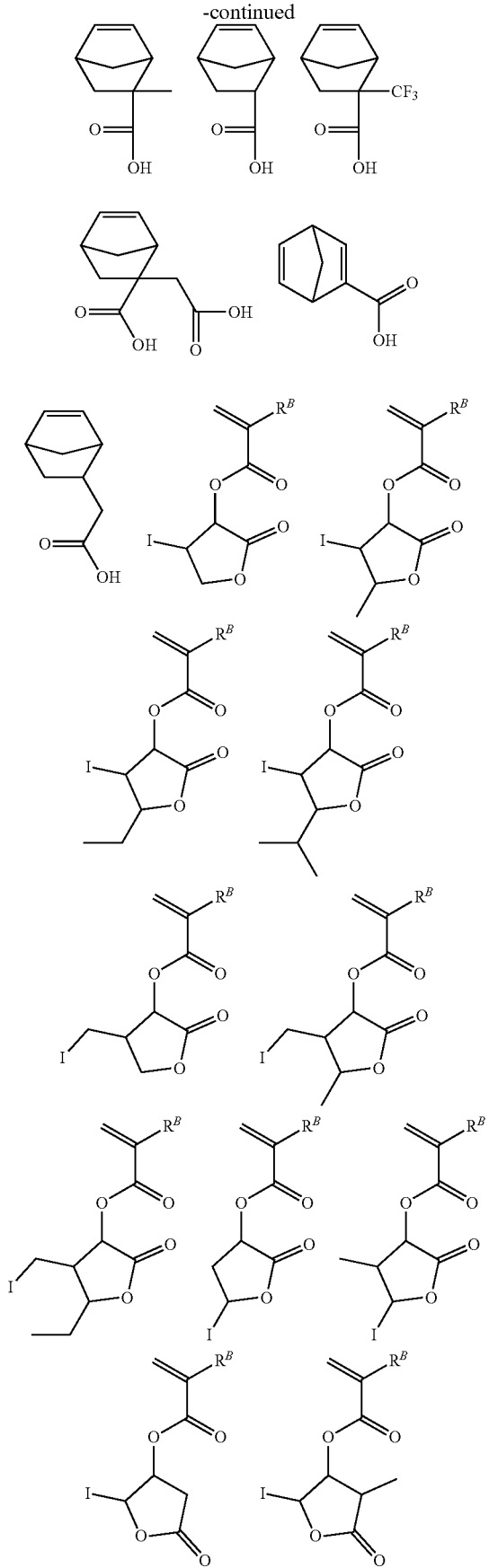
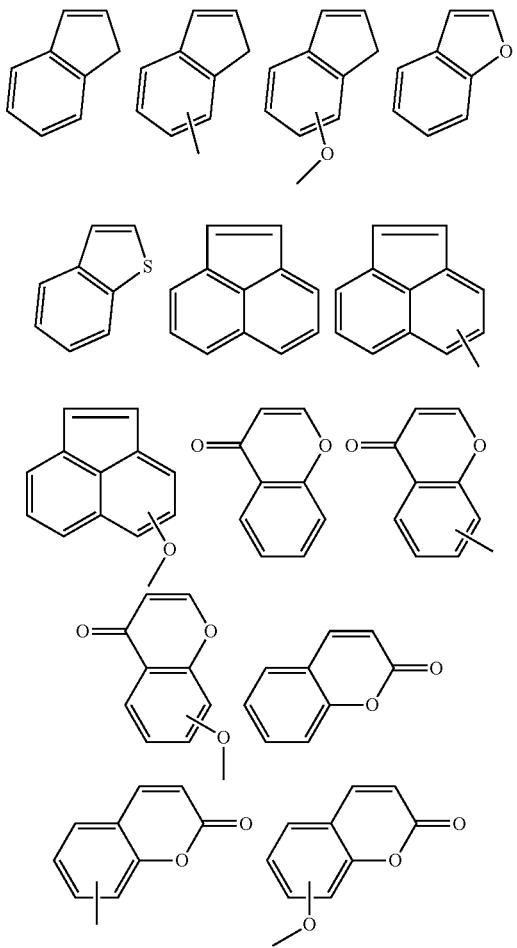
In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

-continued

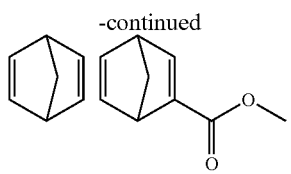

The base polymer may further comprise recurring units (e) derived from styrene, vinylnaphthalene, vinylanthracene, vinylpyrene, methyleneindene, vinylpyridine, and vinylcarbazole.

The base polymer may further comprise recurring units (f) derived from an onium salt having a polymerizable unsaturated bond. Preferred recurring units (f) include recurring units having formula (f1), recurring units having formula (f2) and recurring units having formula (f3). These units are simply referred to as recurring units (f1), (f2) and (f3), which may be used alone or in combination of two or more types.

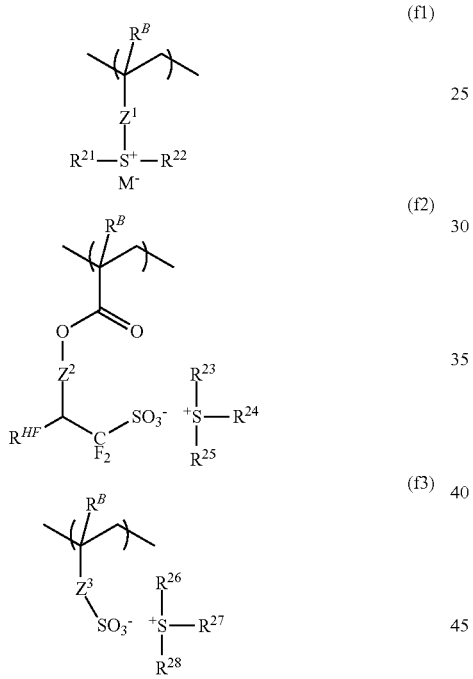

In formulae (f1) to (G), $R^B$ is each independently hydrogen or methyl. $Z^1$ is a single bond, a $C_1$-$C_6$ aliphatic hydrocarbylene group, phenylene group, naphthylene group, or $C_7$-$C_{18}$ group obtained by combining the foregoing, or —O—$Z^{11}$—, —C(=O)—O—$Z^{11}$— or —C(=O)—NH—$Z^{11}$—. $Z^{11}$ is a $C_1$-$C_6$ aliphatic hydrocarbylene group, phenylene group, naphthylene group, or $C_7$-$C_{18}$ group obtained by combining the foregoing which may contain a carbonyl moiety, ester bond, ether bond or hydroxyl moiety. $Z^2$ is a single bond, —$Z^{21}$—C(=O)—O—, —$Z^{21}$—O— or —$Z^{21}$—O—C(=O)—. $Z^{21}$ is a $C_1$-$C_{12}$ saturated hydrocarbylene group which may contain a carbonyl moiety, ester bond or ether bond. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—. $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety. Notably, the aliphatic hydrocarbylene group represented by $Z^{11}$ and $Z^{31}$ may be saturated or unsaturated and straight, branched or cyclic. The saturated hydrocarbylene group represented by $Z^{21}$ may be straight, branched or cyclic.

In formulae (f1) to (G), $R^{21}$ to $R^{28}$ are each independently halogen or a $C_1$-$C_{20}$ hydrocarbyl group which may contain a heteroatom. The hydrocarbyl group may be saturated or unsaturated and straight, branched or cyclic. Examples thereof are as will be exemplified later for the hydrocarbyl group represented by $R^{101}$ to $R^{105}$ in formulae (1-1) and (1-2).

A pair of $R^{23}$ and $R^{24}$ or $R^{26}$ and $R^{27}$ may bond together to form a ring with the sulfur atom to which they are attached. Examples of the ring are as will be exemplified later for the ring that $R^{101}$ and $R^{102}$ in formula (1-1), taken together, form with the sulfur atom to which they are attached.

In formula (f2), $R^{HF}$ is hydrogen or trifluoromethyl.

In formula (f1), M⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α-position and trifluoromethyl substituted at β-position as represented by the formula (f1-2).

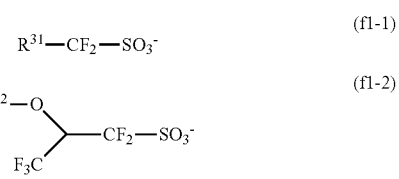

In formula (f1-1), $R^{31}$ is hydrogen or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic. Examples thereof are as will be exemplified for the hydrocarbyl group $R^{111}$ in formula (1A').

In formula (f1-2), $R^{32}$ is hydrogen or a $C_1$-$C_{30}$ hydrocarbyl or $C_2$-$C_{30}$ hydrocarbylcarbonyl group, which may contain an ether bond, ester bond, carbonyl moiety or lactone ring. The hydrocarbyl group and the hydrocarbyl moiety in the hydrocarbylcarbonyl group may be saturated or unsaturated and straight, branched or cyclic. Examples thereof are as will be exemplified for the hydrocarbyl group R111 in formula (1A').

Examples of the cation in the monomer from which recurring unit (f1) is derived are shown below, but not limited thereto. $R^B$ is as defined above.

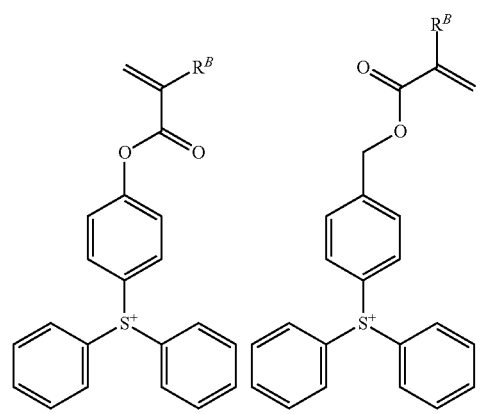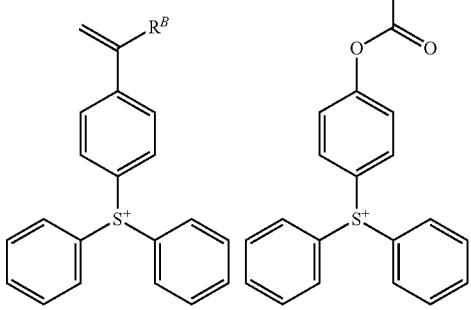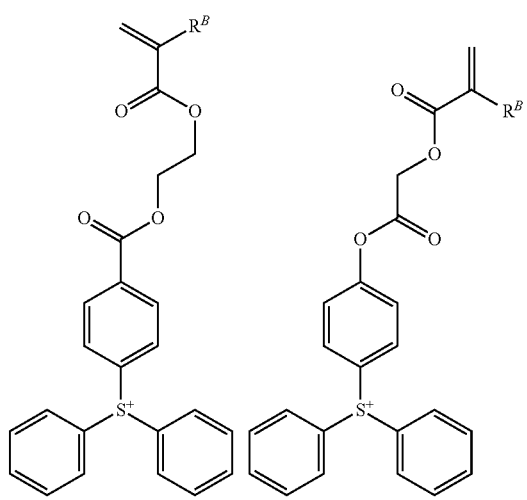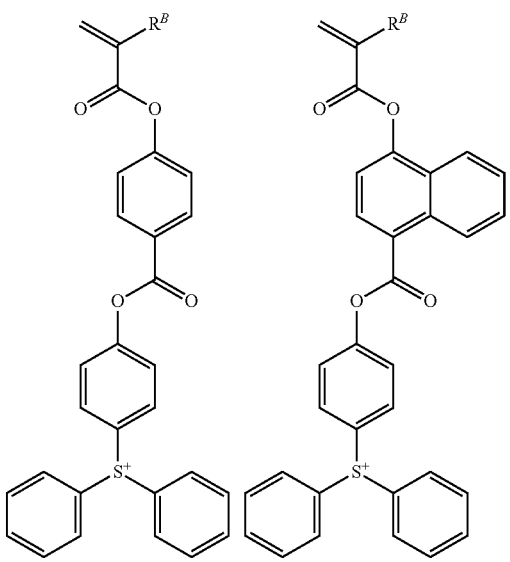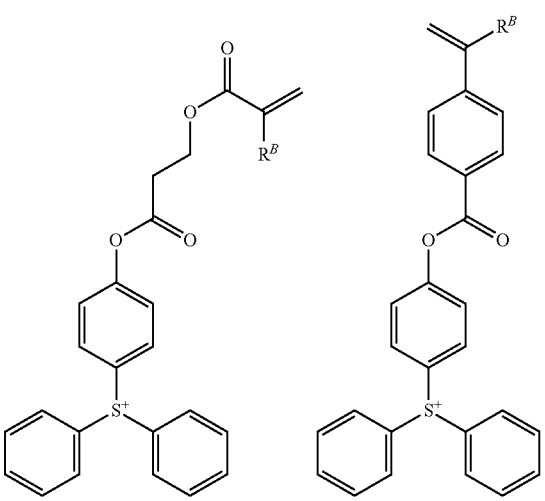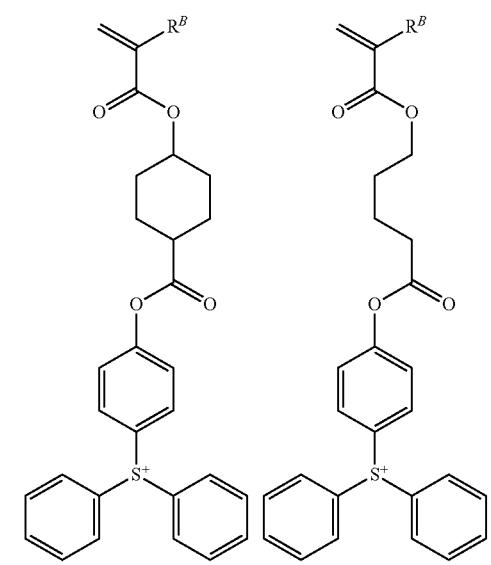

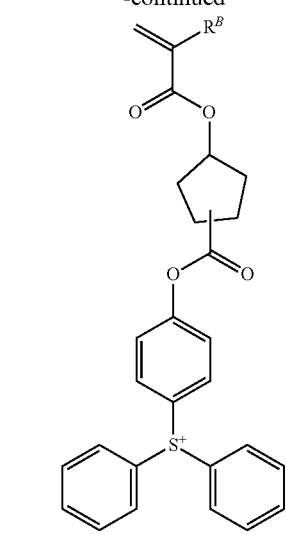
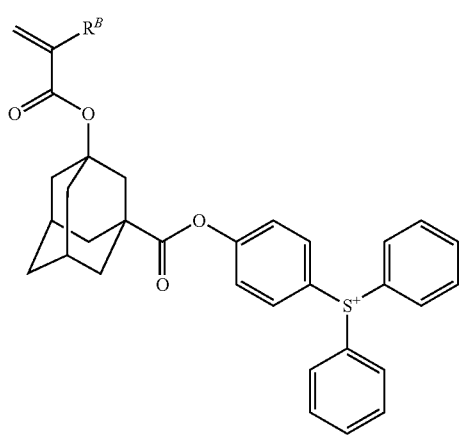
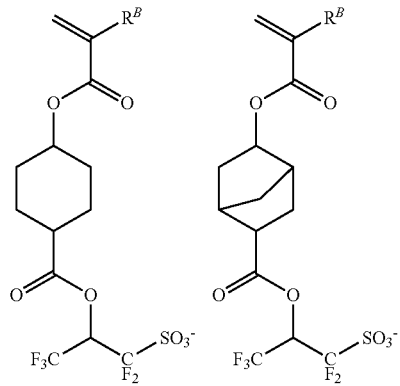
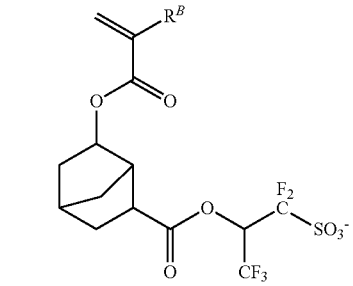
Examples of the cation in the monomer from which recurring unit (f2) or (f3) is derived are as will be exemplified for the cation in the sulfonium salt having formula (1-1).
Examples of the anion in the monomer from which recurring unit (f2) is derived are shown below, but not limited thereto. $R^B$ is as defined above.
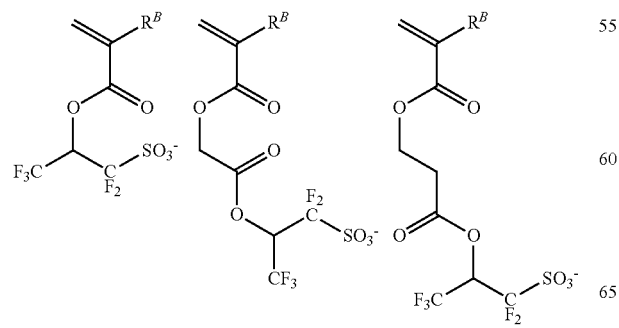
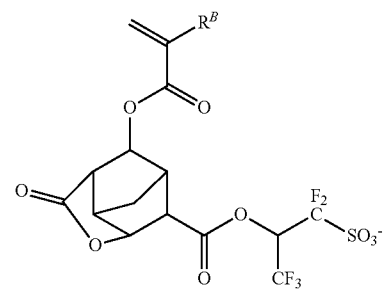
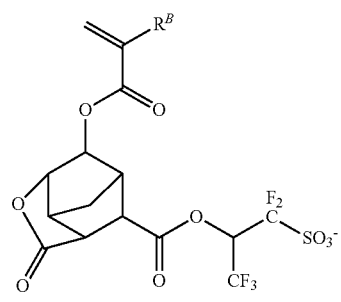
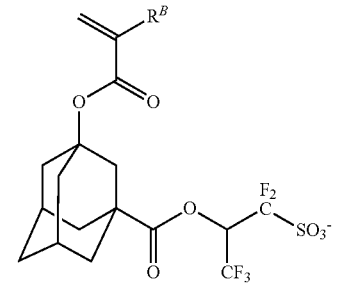

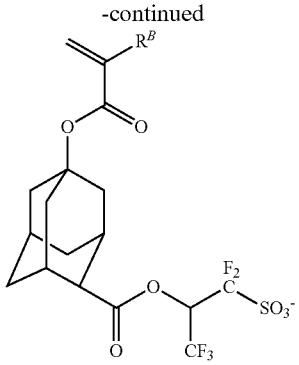
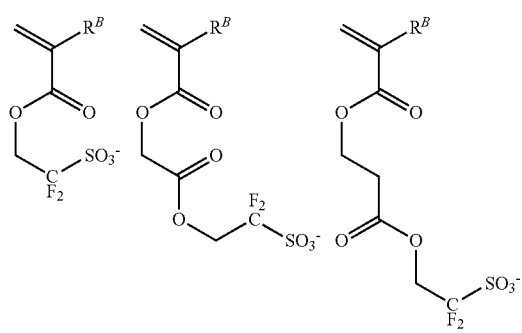
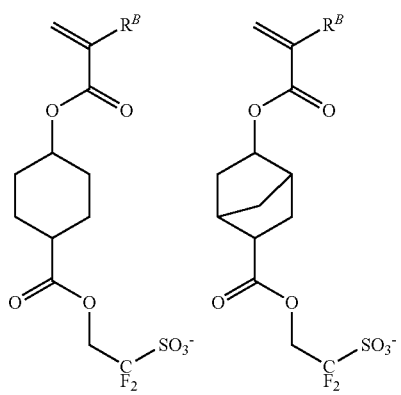
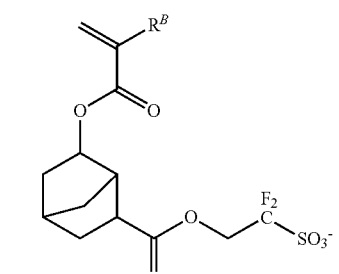
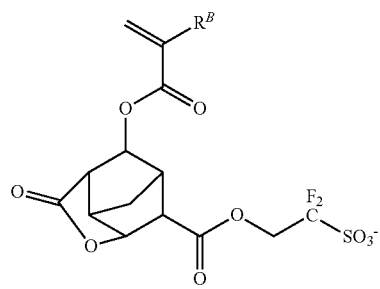
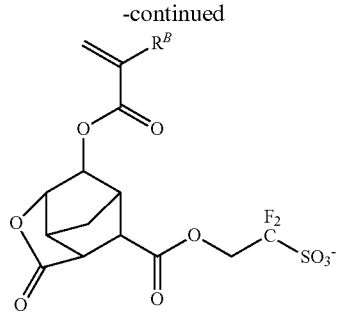
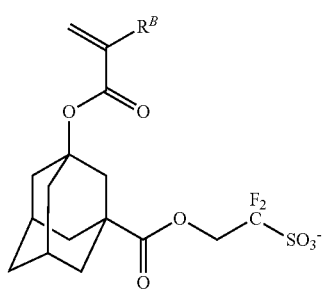
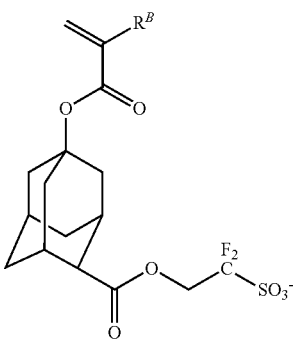
Examples of the anion in the monomer from which recurring unit (f3) is derived are shown below, but not limited thereto. $R^B$ is as defined above.
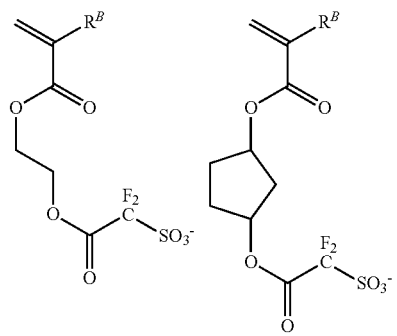

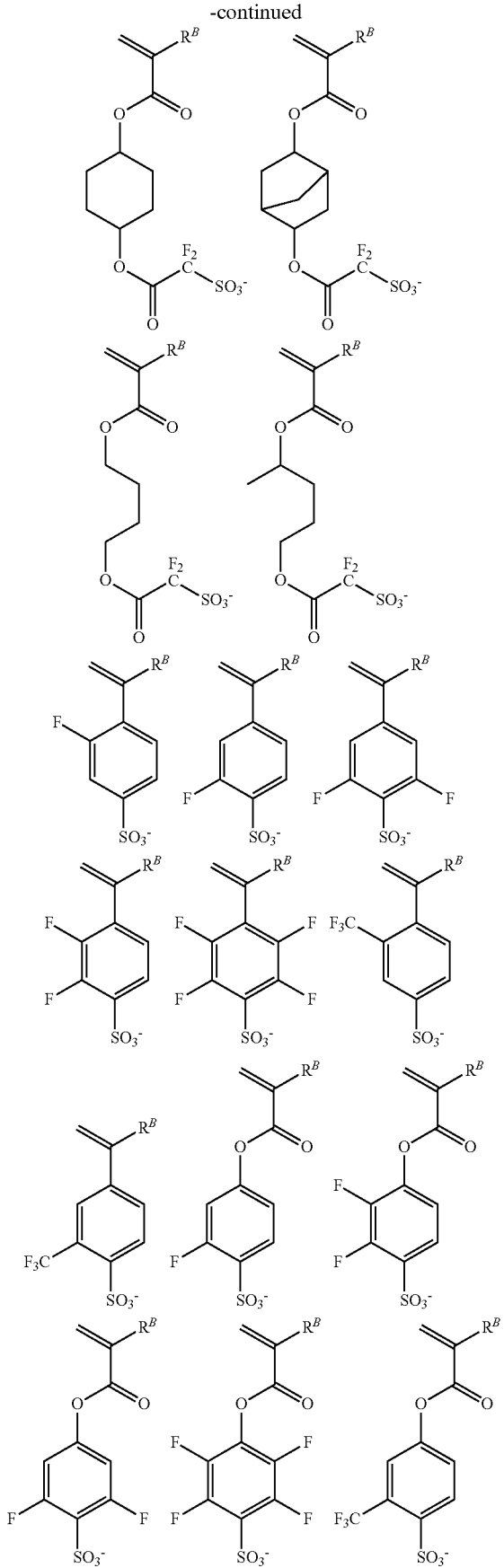

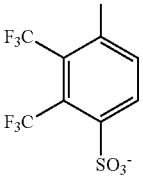

The attachment of an acid generator to the polymer main chain is effective in restraining acid diffusion, thereby preventing a reduction of resolution due to blur by acid diffusion. Also LWR or CDU is improved since the acid generator is uniformly distributed. Where a base polymer containing recurring units (f), i.e., polymer-bound acid generator is used, the addition of a separate acid generator may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d \leq 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and a1+a2+b+c+d+e+f=1.0.

For the base polymer for formulating the negative resist composition, an acid labile group is not necessarily essential. The base polymer comprises reclining units (b), and optionally recurring units (c), (d), (e), and/or (f). A fraction of these units is: preferably $0 < b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, $f=f1+2+f3$, meaning that unit (f) is at least one of units (f1) to (f3), and b+c+d+e+f=1.0.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the polymerization temperature is 50 to 80° C. and the reaction time is 2 to 100 hours, more preferably 5 to 20 hours.

Where a monomer having a hydroxyl group is copolymerized, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a Mw in the range of 1,000 to 500,000, and more preferably 2,000 to 30,000, as measured by GPC versus polystyrene standards using THF solvent. A Mw in the range ensures that the resist film has heat resistance and solubility in alkaline developer.

If a base polymer has a wide Mw/Mn, which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, sulfonium salts having the formula (1-1) and iodonium salts having the formula (1-2) are also preferred.

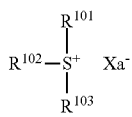
(1-1)

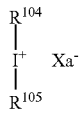
(1-2)

In formulae (1-1) and (1-2), $R^{101}$ to $R^{105}$ are each independently halogen or a $C_4$-$C_{20}$ hydrocarbyl group which may contain a heteroatom. Suitable halogen atoms include fluorine, chlorine, bromine and iodine. The $C_1$-$C_{20}$ hydrocarbyl group may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ saturated cyclic hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, propenyl, butenyl, and hexenyl; $C_2$-$C_{20}$ alkynyl groups such as ethynyl, propynyl and butynyl; $C_3$-$C_{20}$ unsaturated alicyclic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, and tert-butylnaphthyl; $C_7$-$C_{20}$ aralkyl groups such as benzyl and phenethyl; and combinations thereof. In the foregoing groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, ester bond, sulfonic ester bond, carbonate moiety, lactone ring, sultone ring, carboxylic anhydride or haloalkyl moiety.

Also, $R^{101}$ and $R^{102}$ may bond together to form a ring with the sulfur atom to which they are attached. Preferred examples of the ring are shown by the following structure.

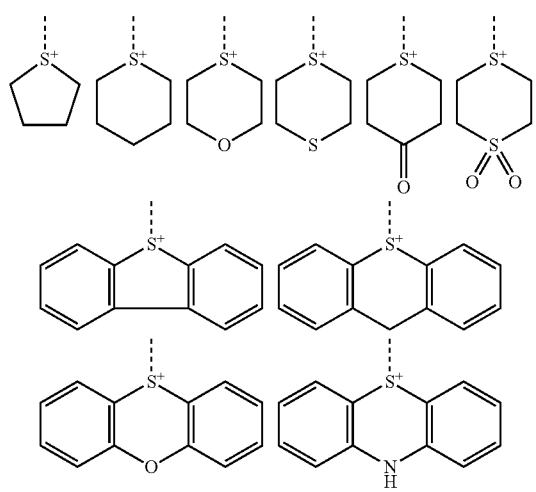

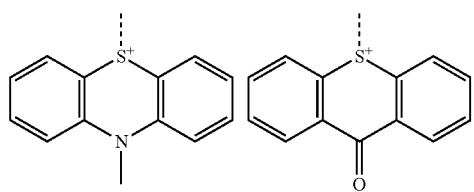
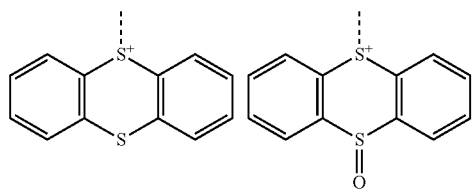
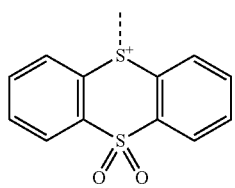
Herein the broken line designates a point of attachment to $R^{103}$.
Examples of the cation in the sulfonium salt having formula (1-1) are shown below, but not limited thereto.
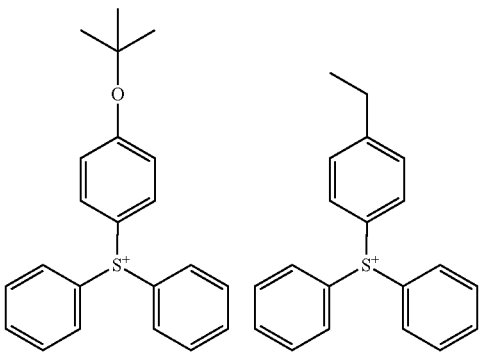
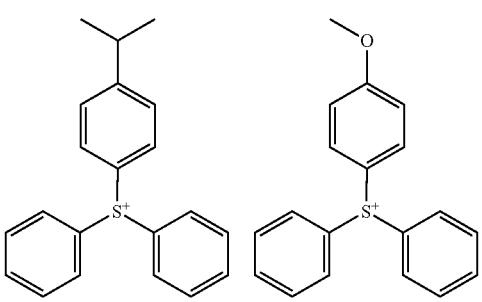
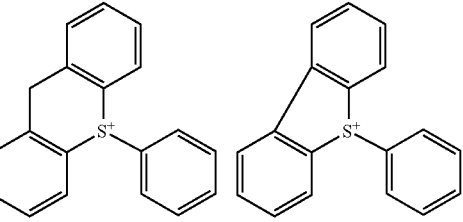
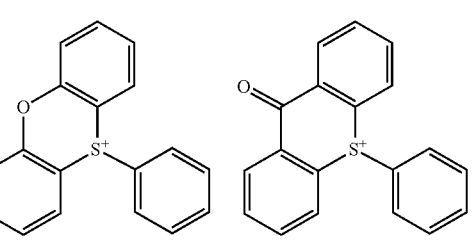
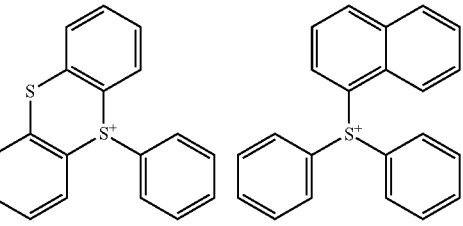
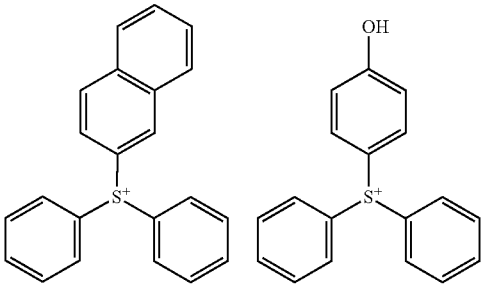

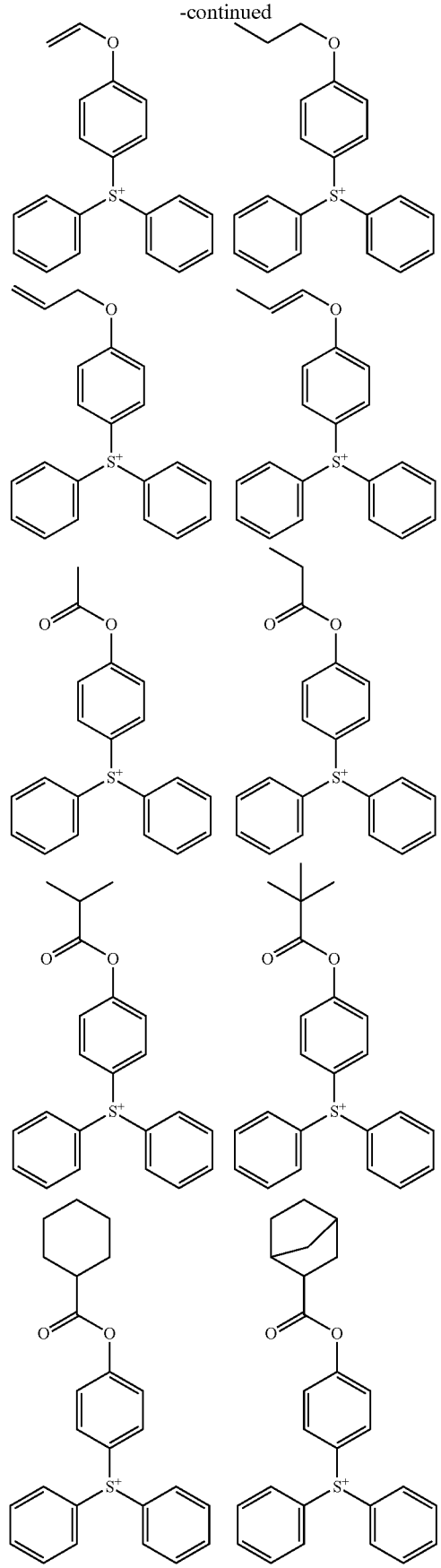
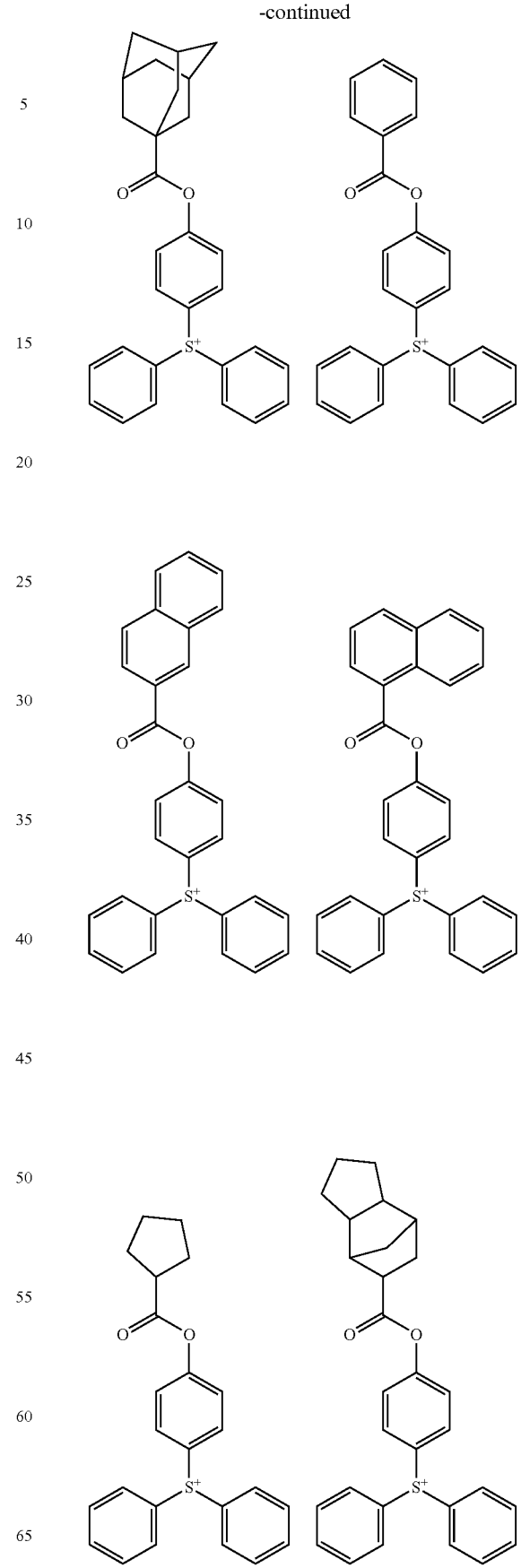

73
-continued
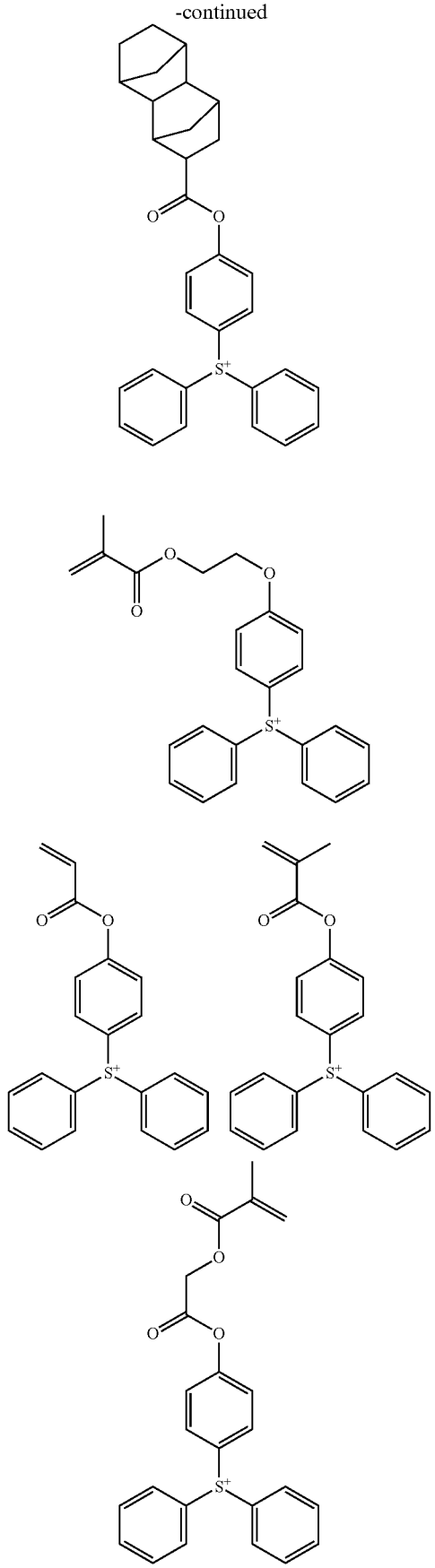
74
-continued
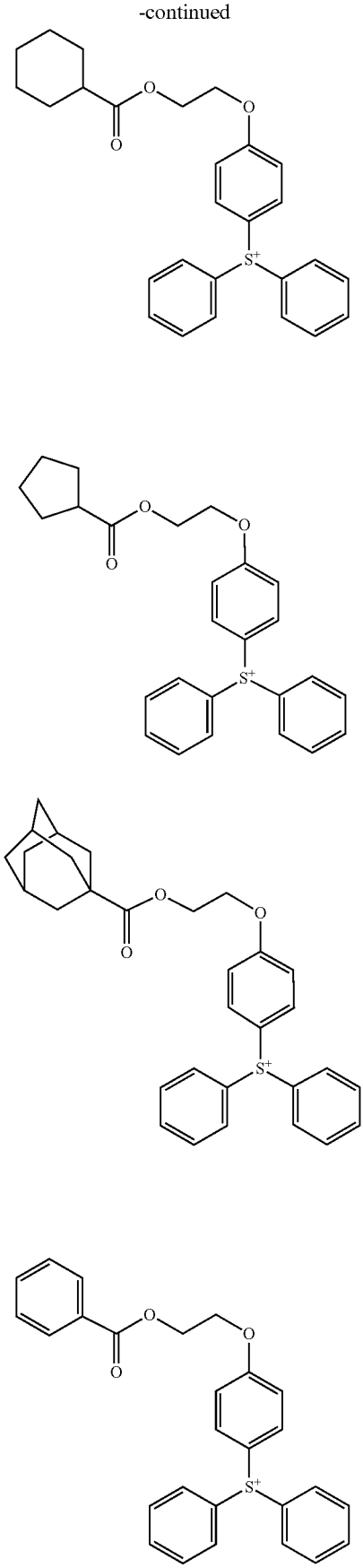

75
-continued
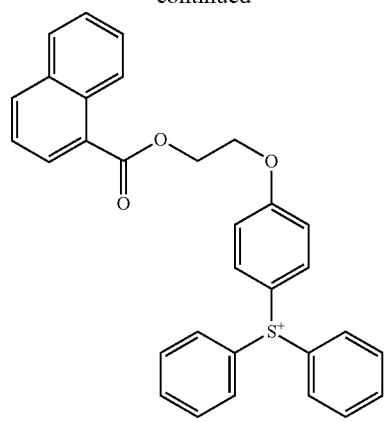
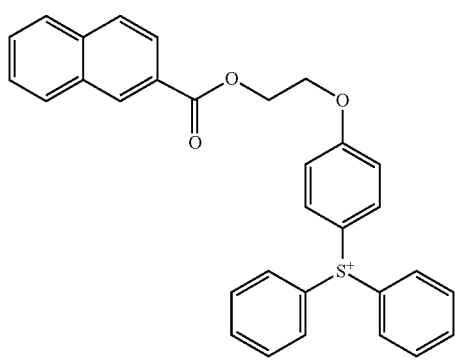
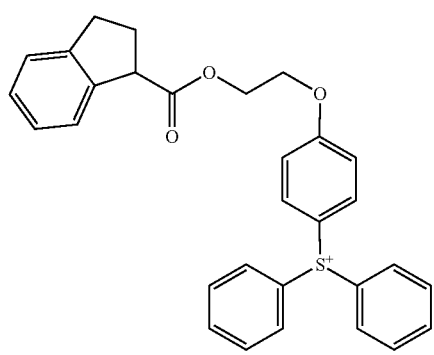
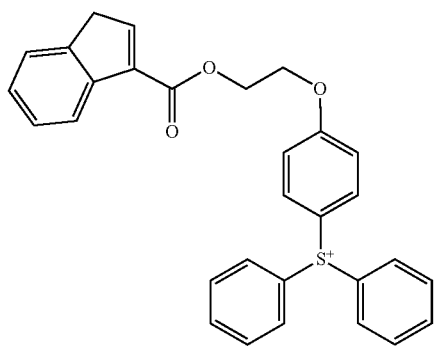
76
-continued
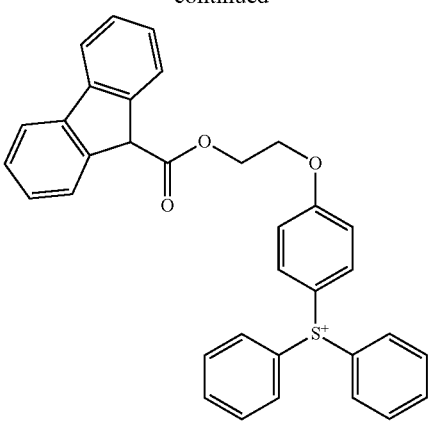
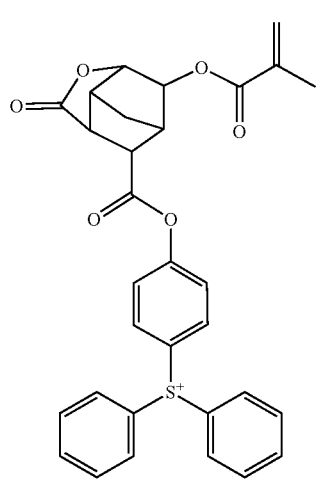
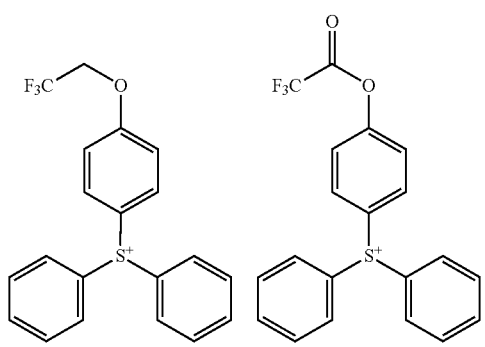
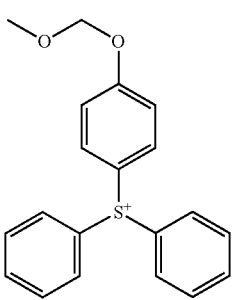

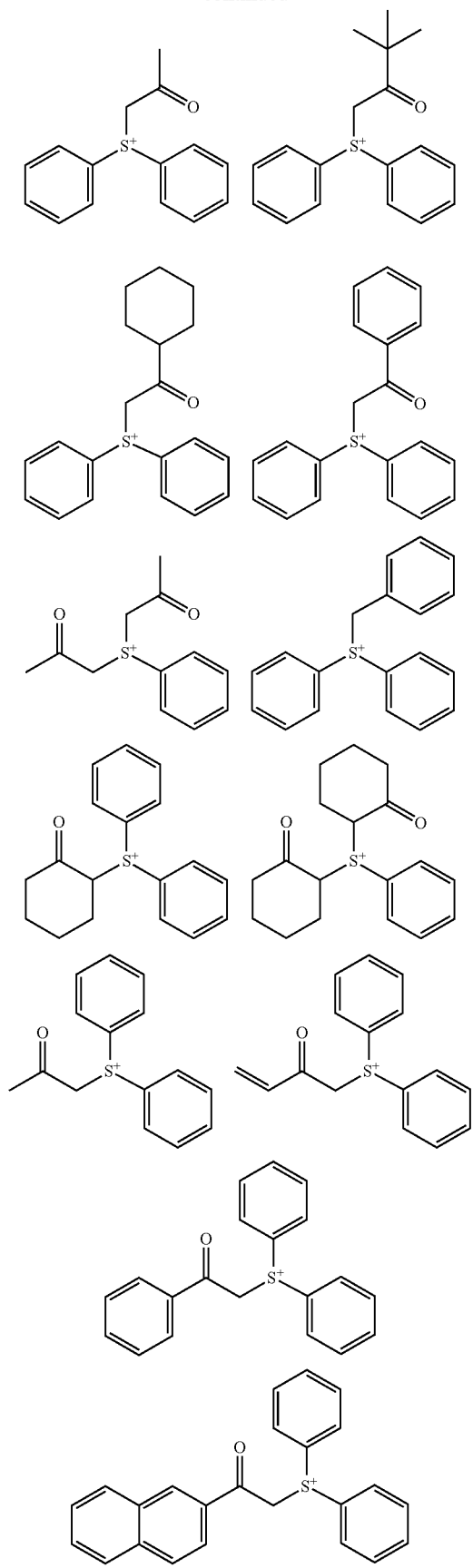
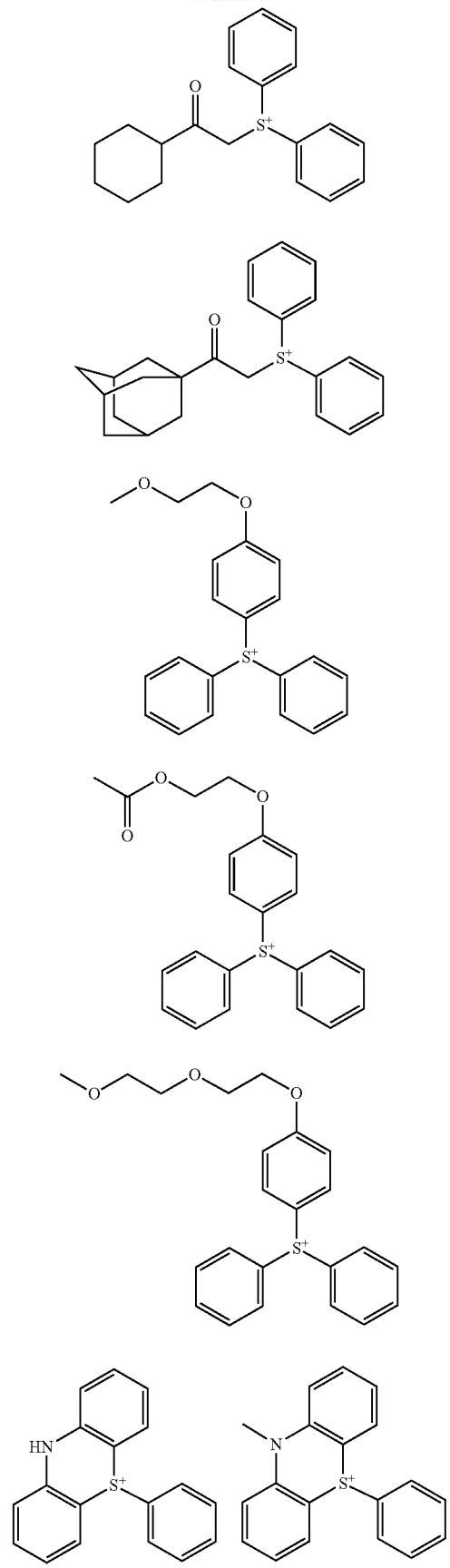

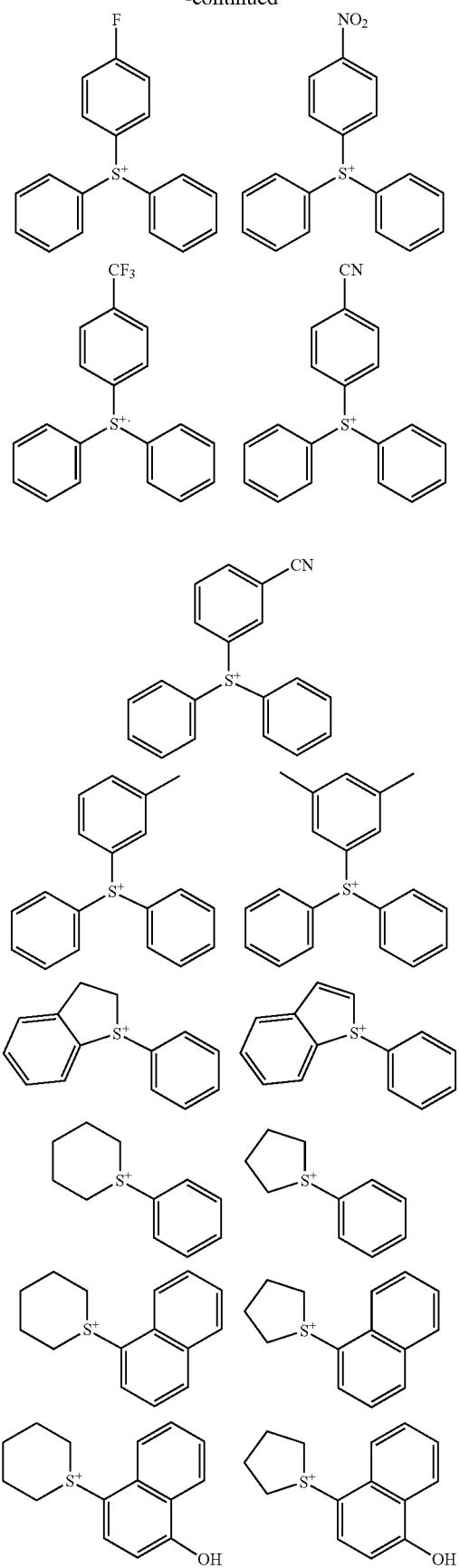
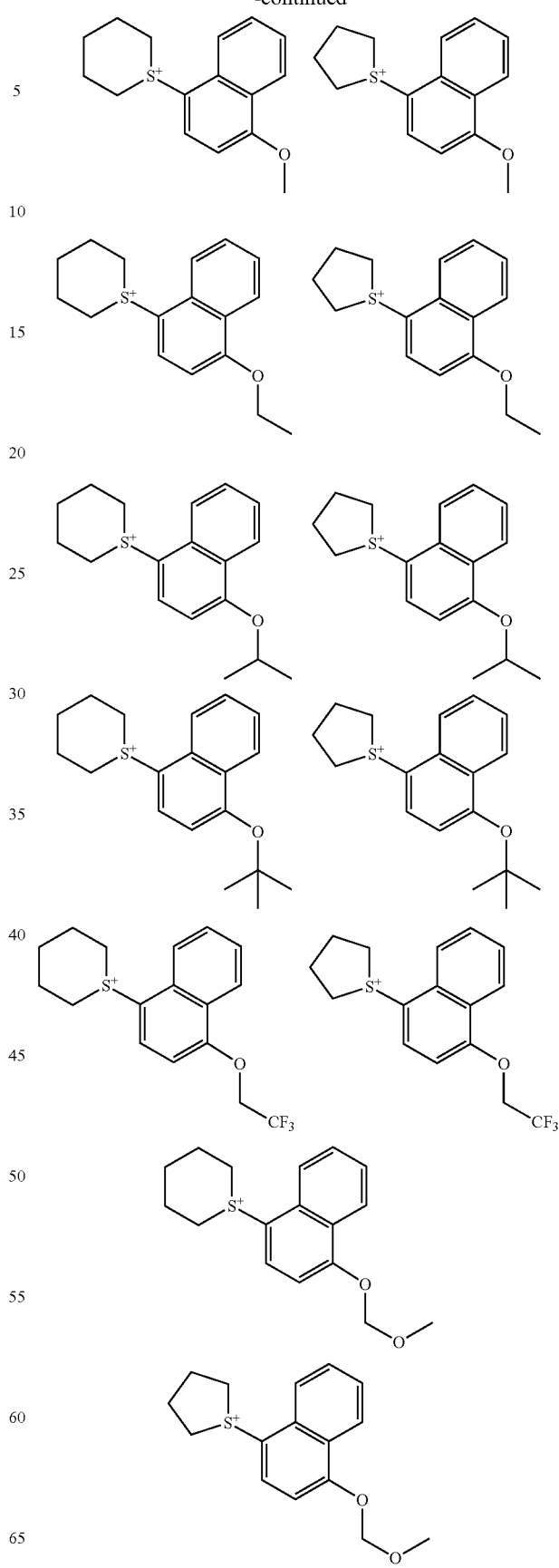

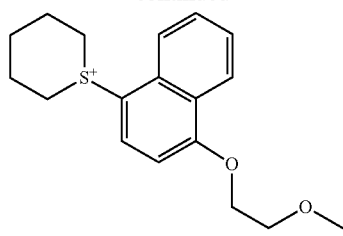
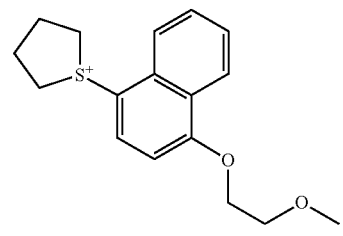
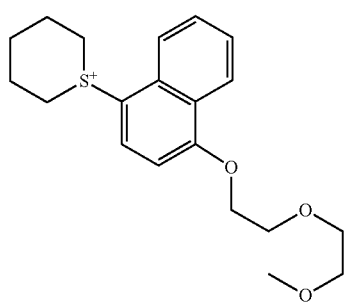
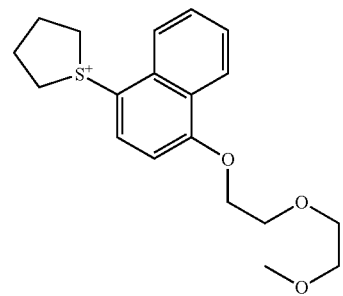
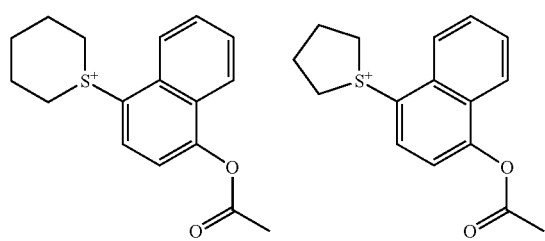
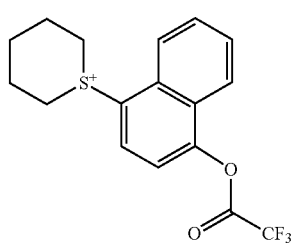
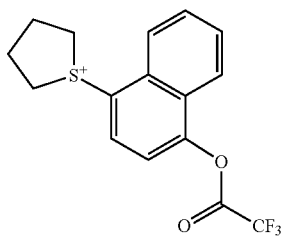
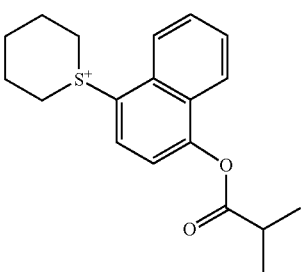
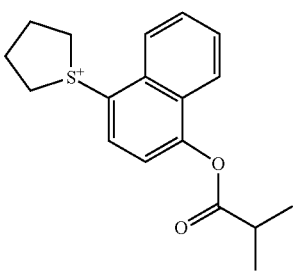
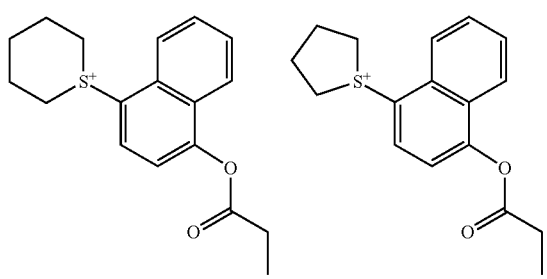
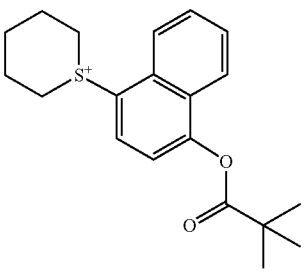
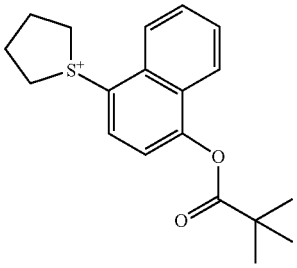

83
-continued
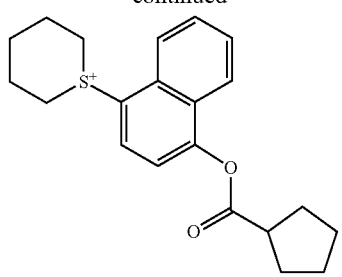
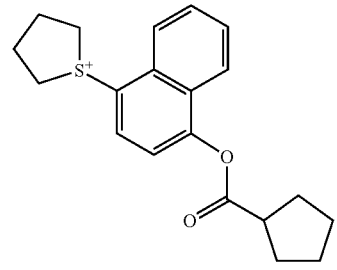
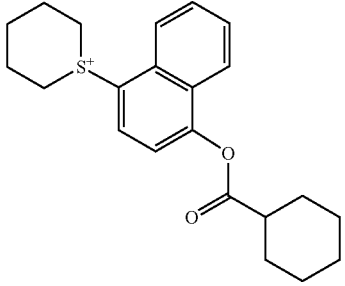
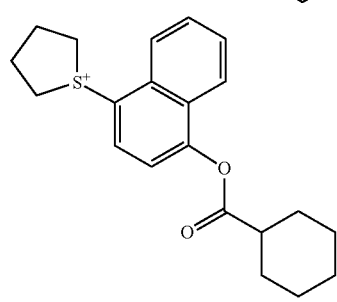
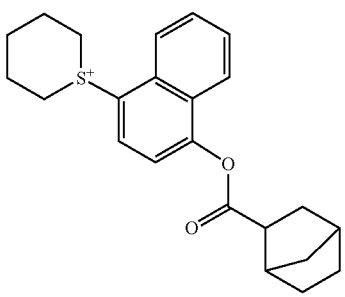
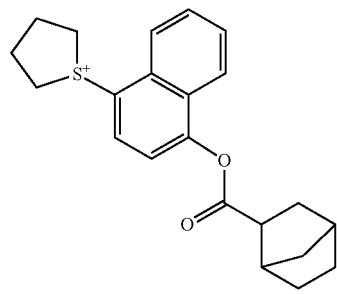
84
-continued
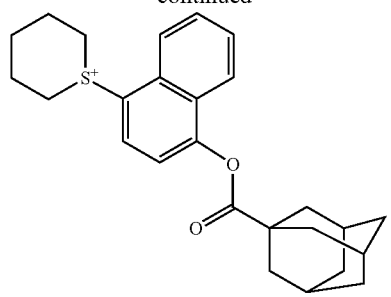
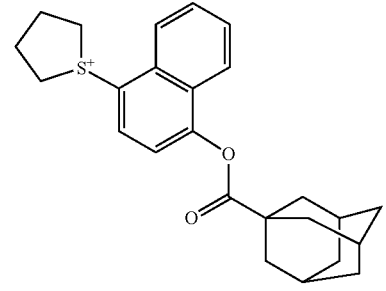
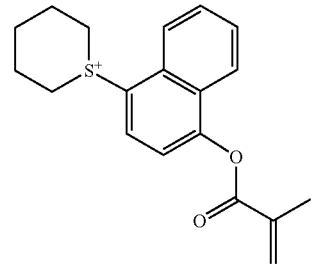
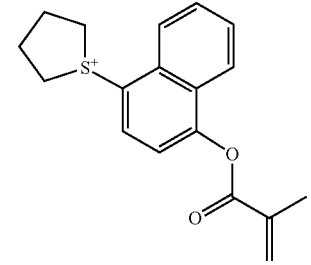
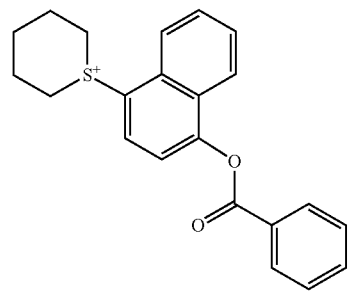
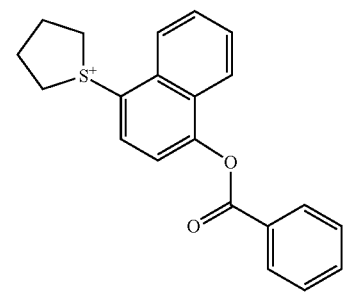

85
-continued
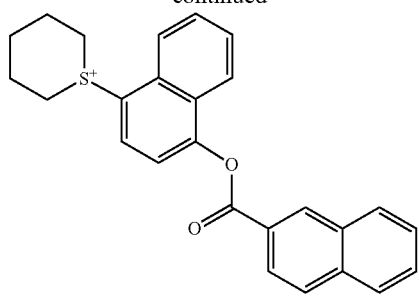
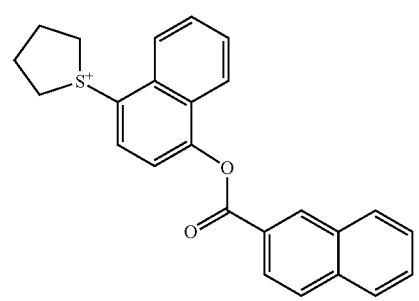
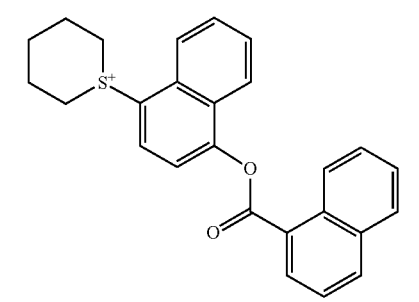
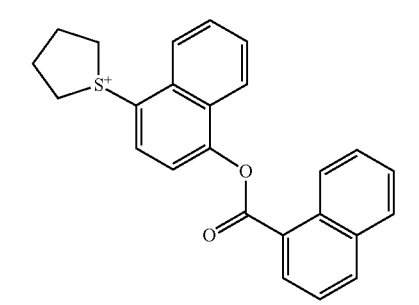
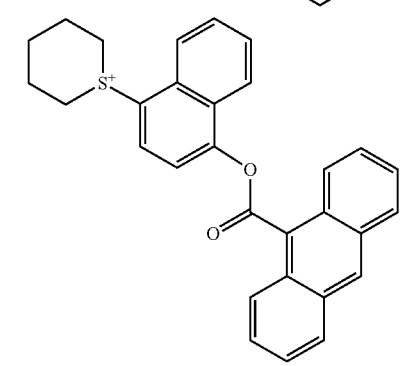
86
-continued
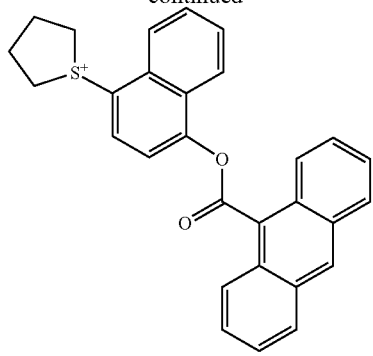
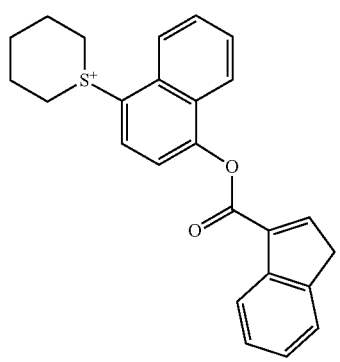
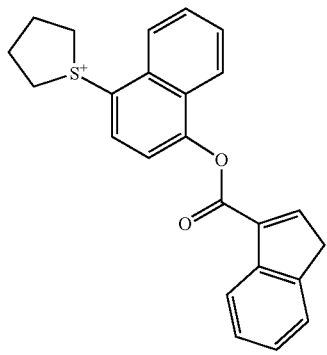
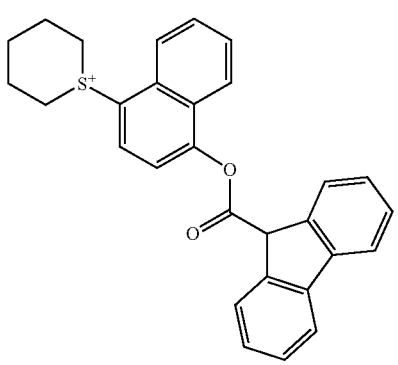

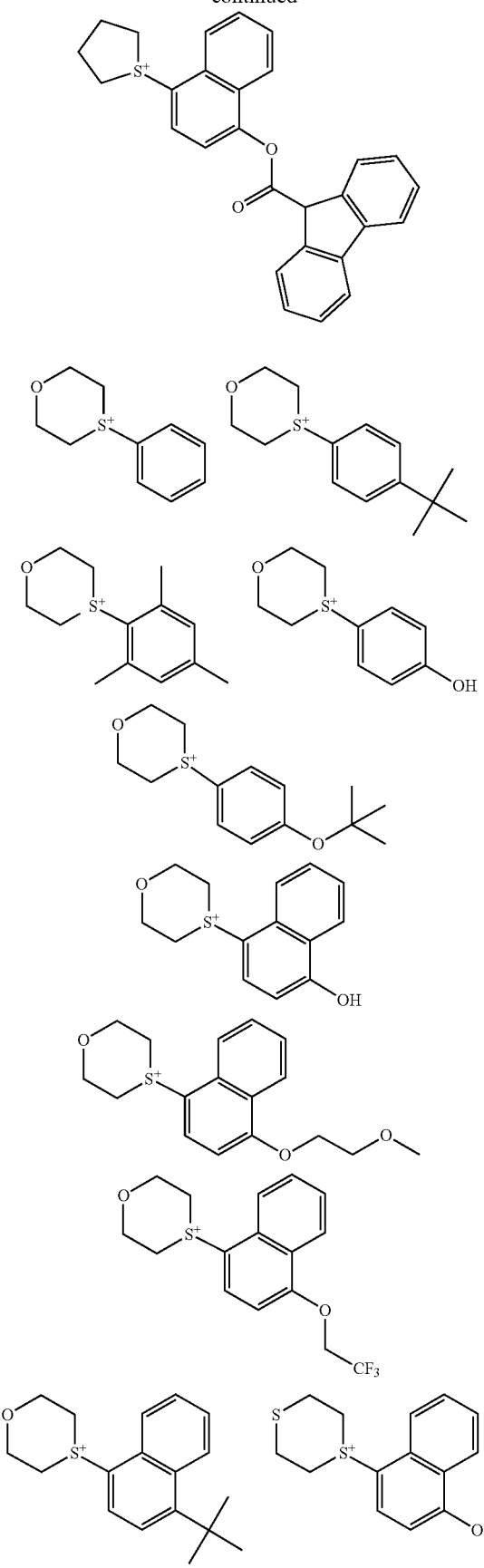
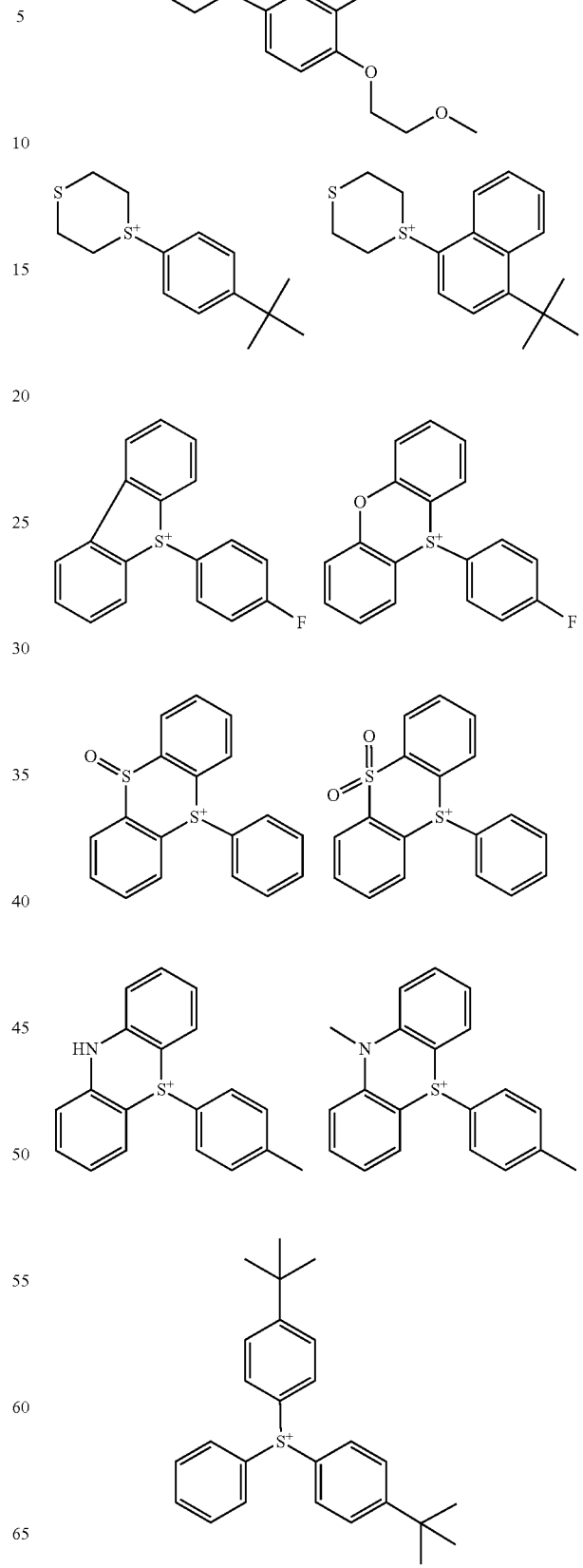

89
-continued
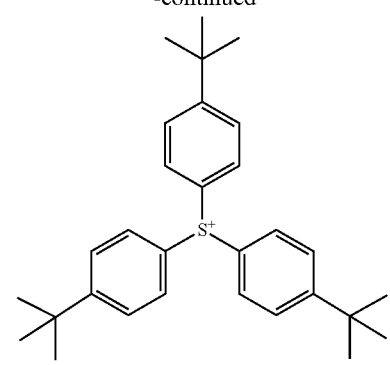
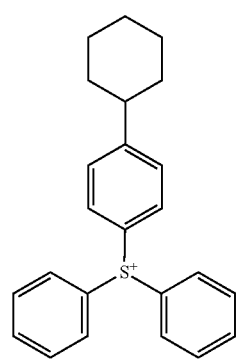
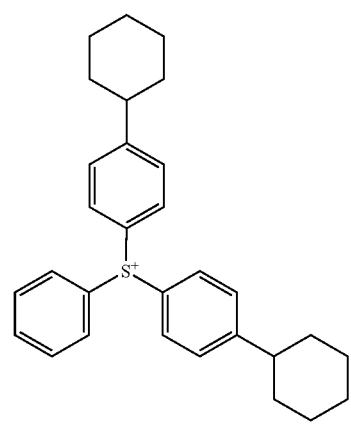 [SMILES: c1ccc([S+](c2ccc(C3CCCCC3)cc2)c2ccc(C3CCCCC3)cc2)cc1]
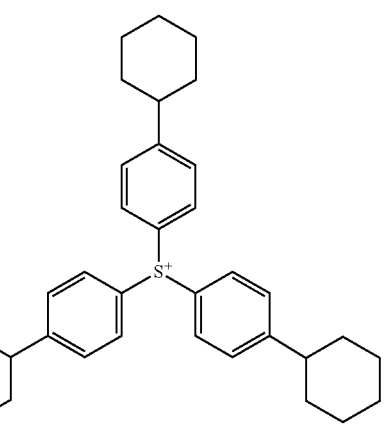
90
-continued
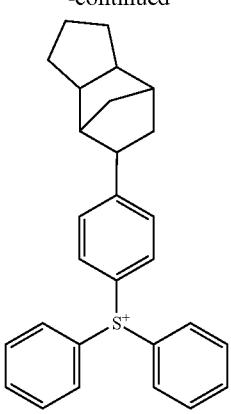
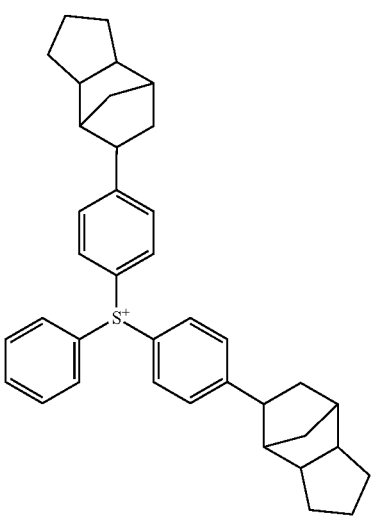
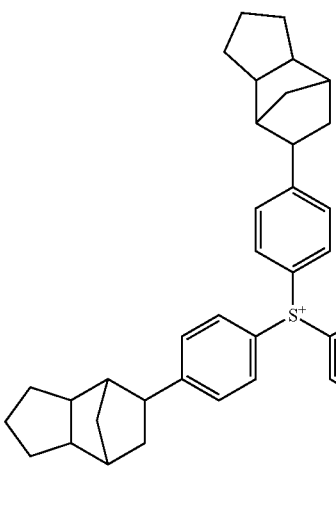

91
-continued
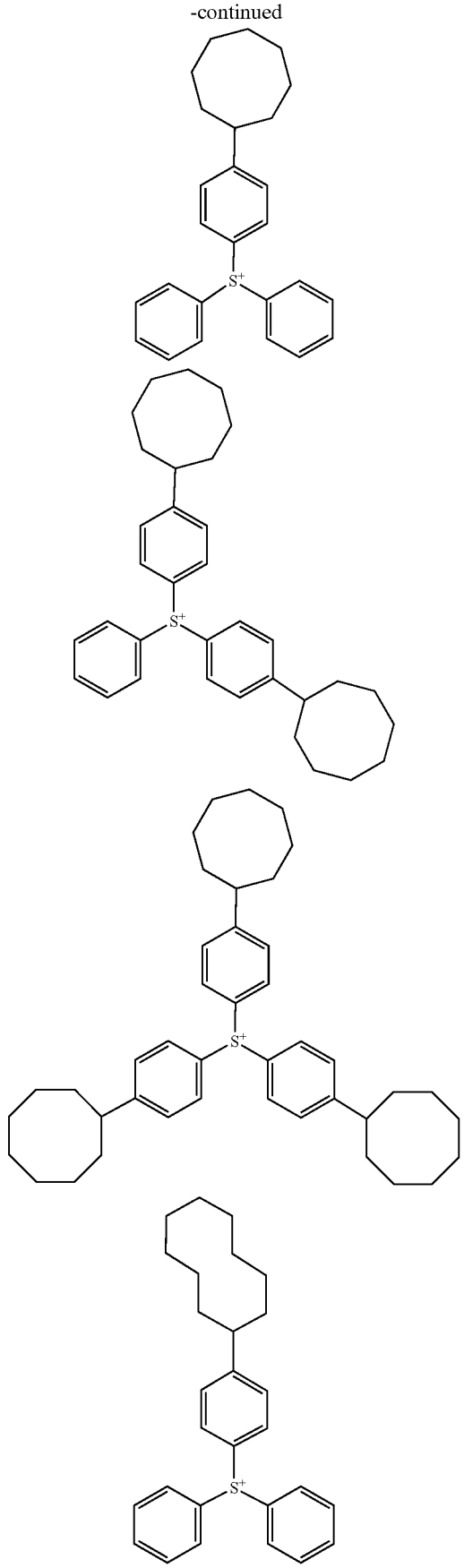
92
-continued
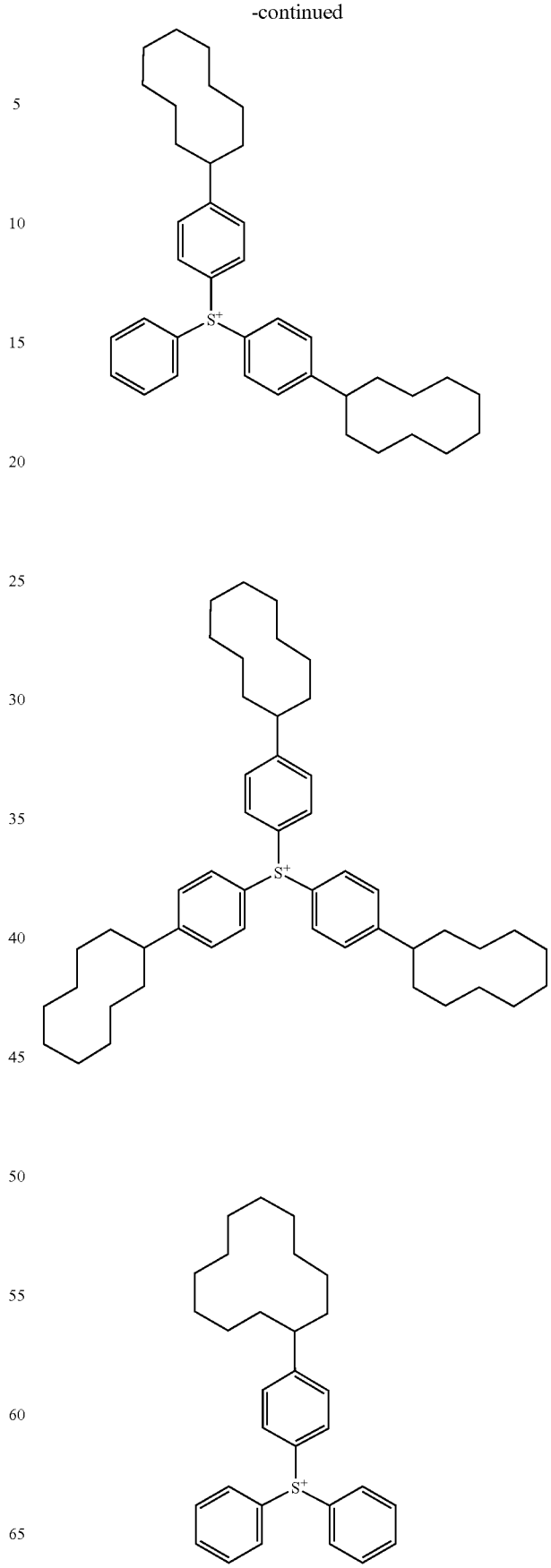

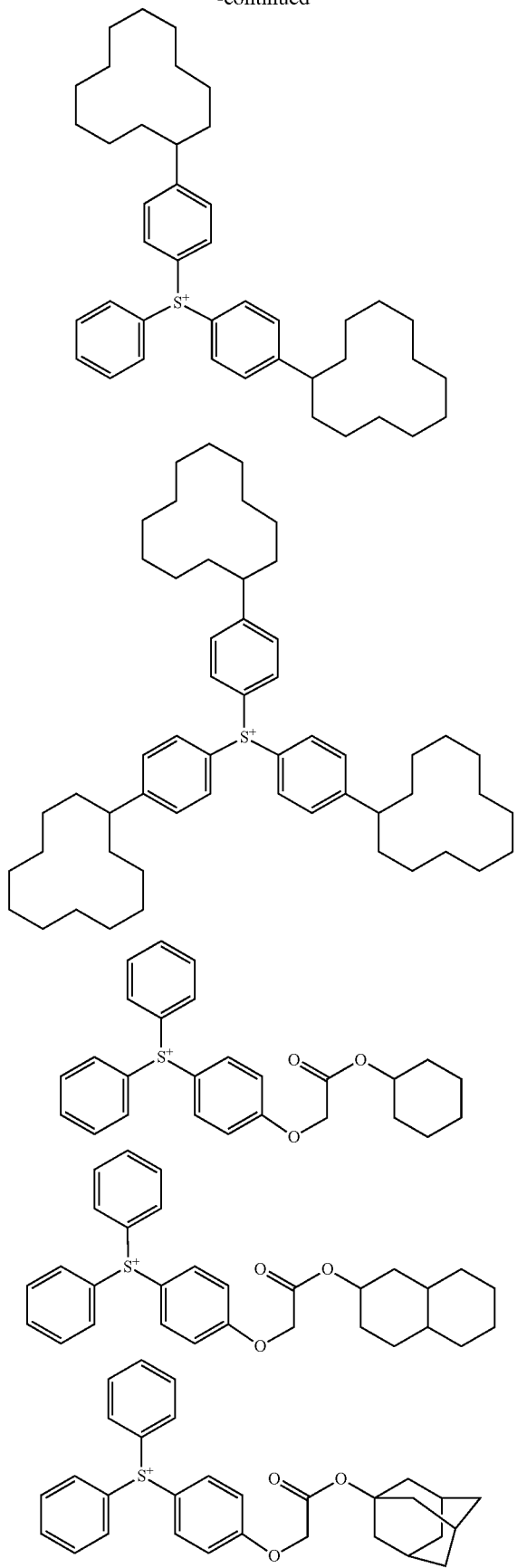
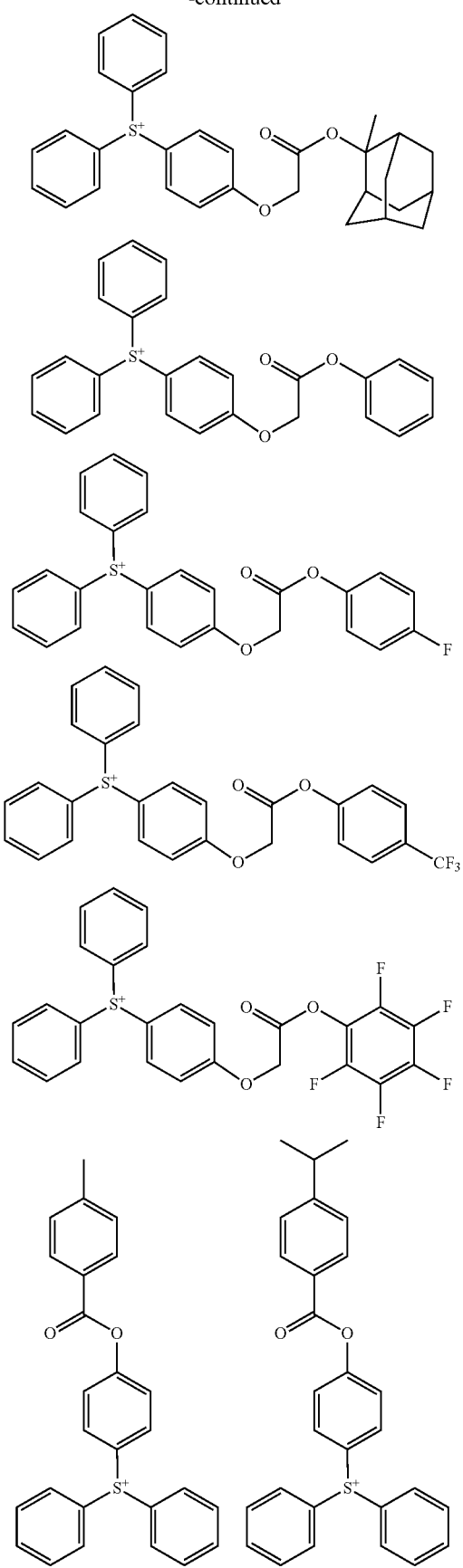

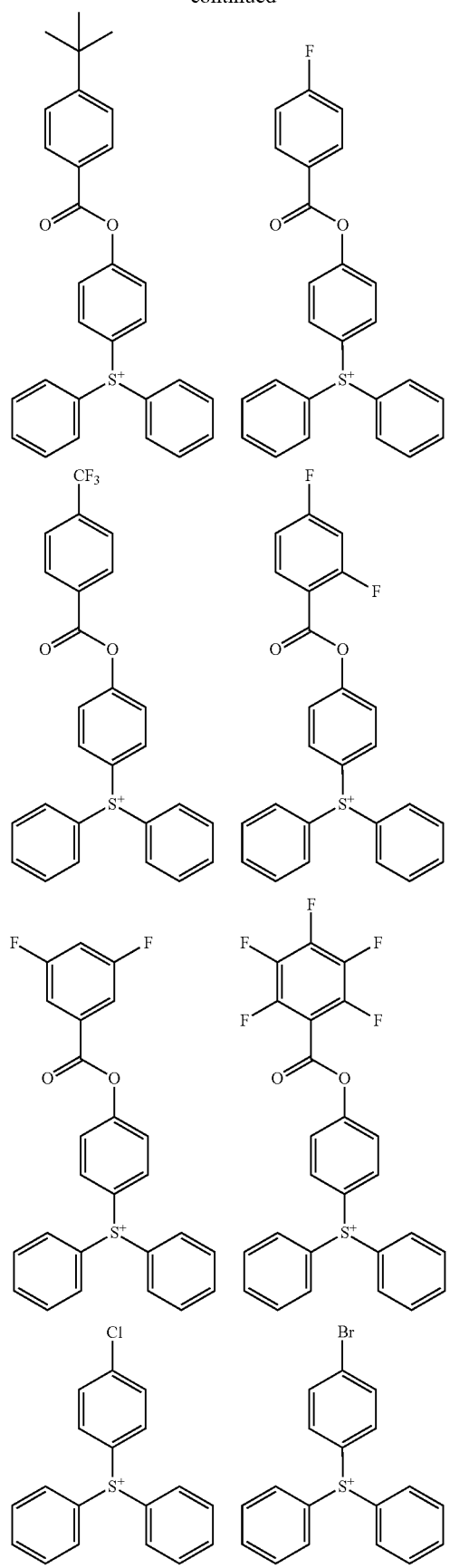
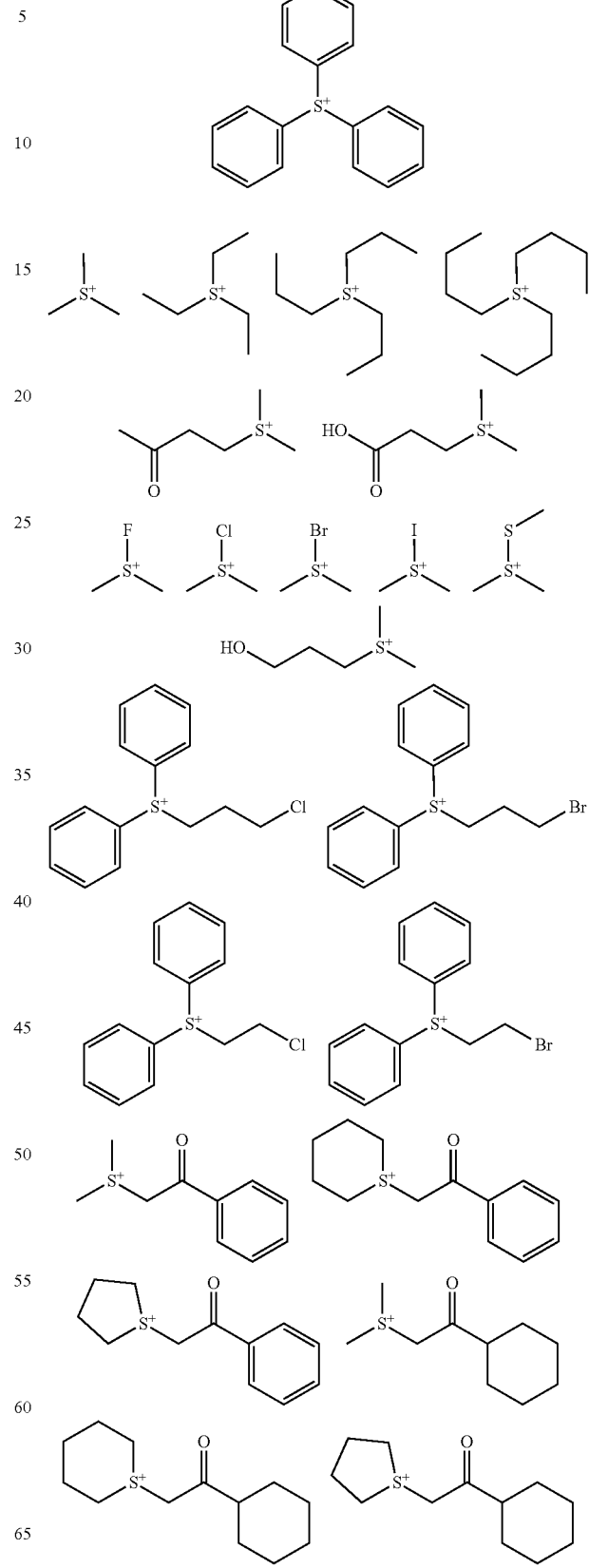

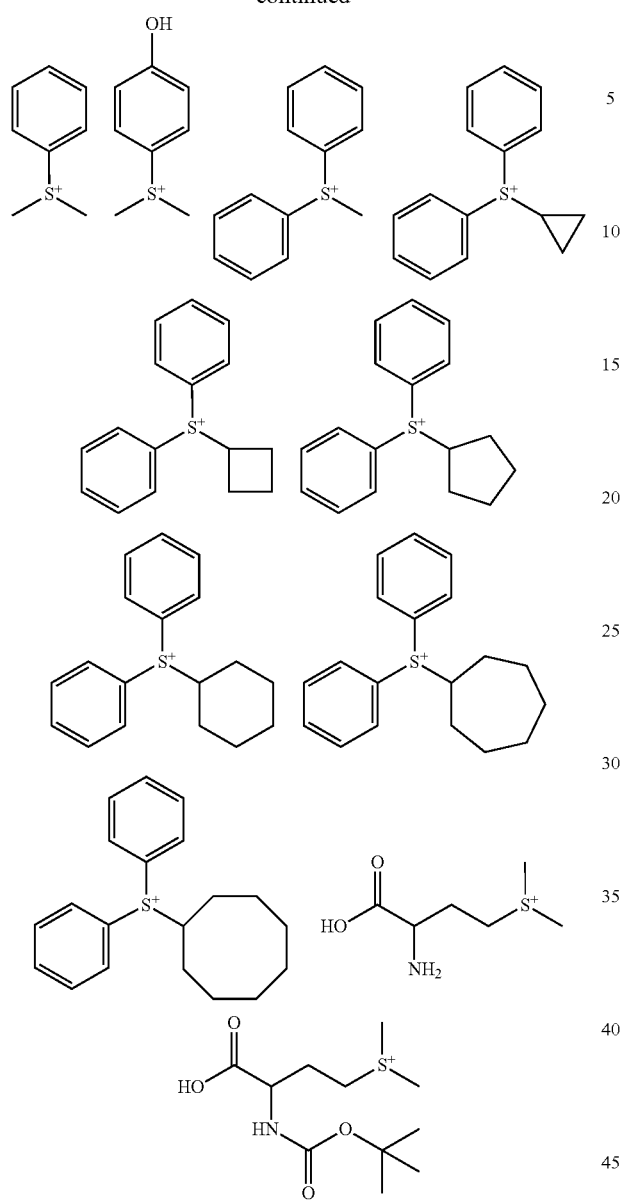
Examples of the cation in the iodonium salt having formula (1-2) are shown below, but not limited thereto.
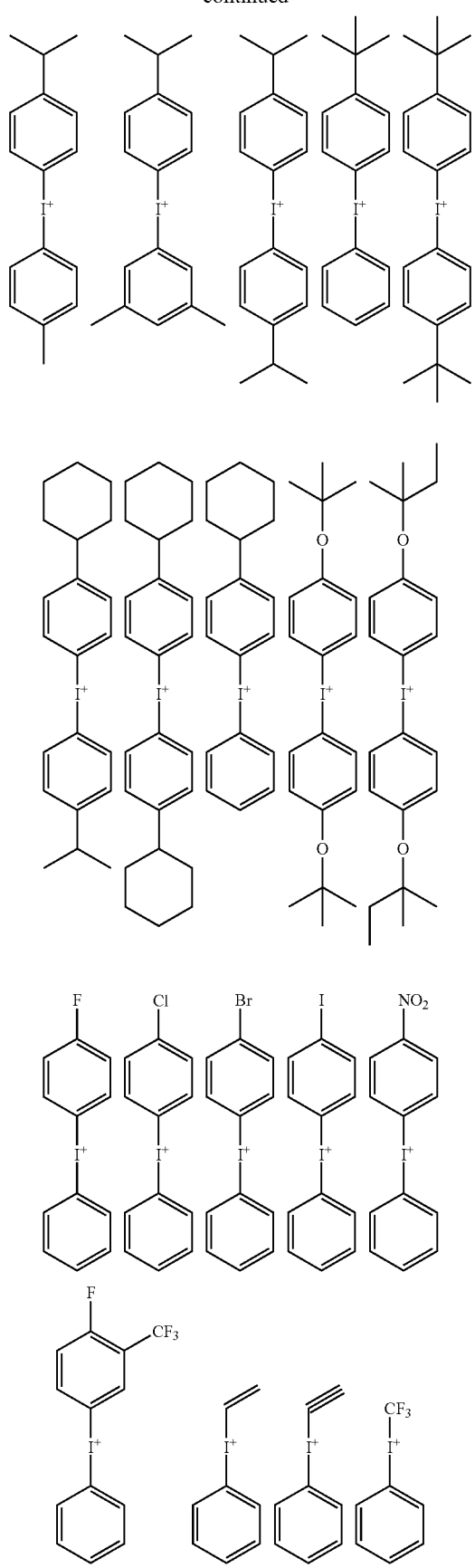

-continued

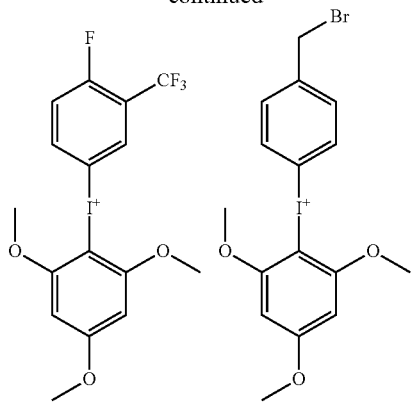

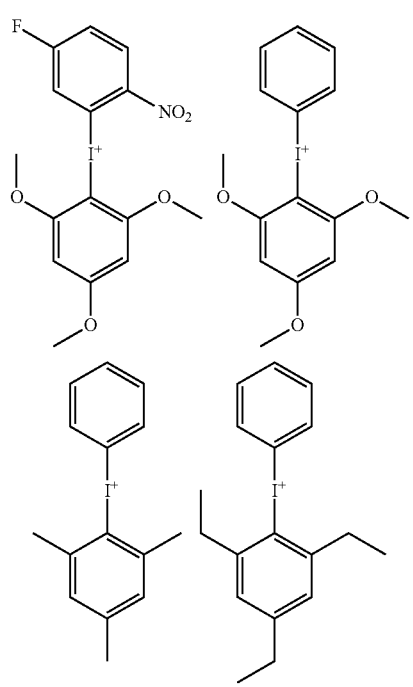

-continued

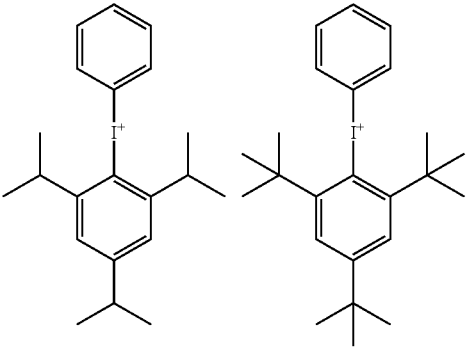

In formulae (1-1) and (1-2), Xa⁻ is an anion selected from the following formulae (1A) to (1D).

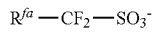
(1A)

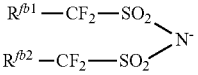
(1B)

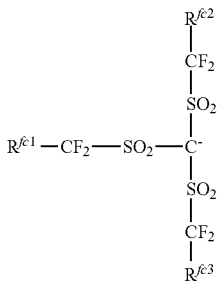
(1C)

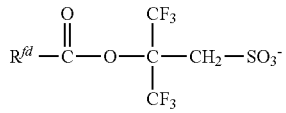
(1D)

In formula (1A), $R^{fa}$ is fluorine or a $C_1$-$C_{40}$ hydrocarbyl group which may contain a heteroatom. The hydrocarbyl group may be saturated or unsaturated and straight, branched or cyclic, and examples thereof are as will be exemplified for the hydrocarbyl group $R^{111}$ in formula (1A').

Of the anions of formula (1A), a structure having formula (1A') is preferred.

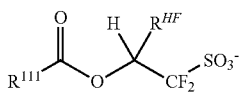
(1A')

In formula (1A'), $R^{HF}$ is hydrogen or trifluoromethyl, preferably trifluoromethyl.

$R^{111}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation. The hydrocarbyl group may be saturated or unsaturated and straight, branched or cyclic. Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{38}$ unsaturated aliphatic hydrocarbyl groups such as allyl and 3-cyclohexenyl; $C_6$-$C_{38}$ aryl groups such as phenyl, 1-naphthyl, 2-naphthyl; $C_7$-$C_{38}$ aralkyl groups such as benzyl and diphenylmethyl; and combinations thereof.

In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having an anion of formula (1 A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are as exemplified for the anion having formula (1A) in JP-A 2018-197853 (US 20180335696).

In formula (1B), $R^{fb1}$ and $R^{fb2}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and the ring-forming pair is preferably a fluorinated ethylene or fluorinated propylene group.

In formula (1C), $R^{fc1}$, $R^{fc2}$ and $R^{fc3}$ are each independently fluorine or a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$ in formula (1A'). Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and the ring-forming pair is preferably a fluorinated ethylene or fluorinated propylene group.

In formula (1D), $R^{fd}$ is a $C_1$-$C_{40}$ hydrocarbyl group which may contain a heteroatom. The hydrocarbyl group may be saturated or unsaturated and straight, branched or cyclic. Suitable hydrocarbyl groups are as exemplified above for $R^{111}$.

With respect to the synthesis of the sulfonium salt having an anion of formula (1D), reference is made to JP-A 2010-215608 and JP-A 2014-133723.

Examples of the anion having formula (1D) are as exemplified for the anion having formula (1D) in JP-A 2018-197853 (US 20180335696).

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

Also compounds having the formula (2) are useful as the PAG.

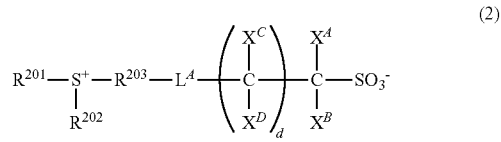
(2)

In formula (2), $R^{201}$ and $R^{202}$ are each independently halogen or a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

The hydrocarbyl groups $R^{201}$ and $R^{202}$ may be saturated or unsaturated and straight, branched or cyclic. Examples thereof include $C_1$-$C_{30}$ alkyl groups such as methyl, ethyl, propyl, isopropyl, n-butyl, sec-butyl, tert-butyl, n-pentyl, tert-pentyl, n-hexyl, n-octyl, 2-ethylhexyl, n-nonyl, and n-decyl; $C_3$-$C_{30}$ cyclic saturated hydrocarbyl groins such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; $C_6$-$C_{30}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl, and anthracenyl; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

The hydrocarbylene group $R^{203}$ may be saturated or unsaturated and straight, branched or cyclic. Examples thereof include $C_1$-$C_{30}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; $C_3$-$C_{30}$ cyclic saturated hydrocarbylene groups such as cyclopentanediyl, cyclohexanediyl, norbornanediyl and adamantanediyl; $C_6$-$C_{30}$ arylene groups such as phenylene, methylphenylene, ethylphenylene, n-propylphenylene, isopropylphenylene, n-butylphenylene, isobutylphenylene, sec-butylphenylene, tert-butylphenylene, naphthylene, methylnaphthylene, ethylnaphthylene, n-propylnaphthylene, isopropylnaphthylene, n-butylnaphthylene, isobutylnaphthylene, and tert-butylnaphthylene; and combinations thereof. In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Of the heteroatoms, oxygen is preferred.

In formula (2), $L^A$ is a single bond, ether bond or a $C_1$-$C_{20}$ hydrocarbylene group which may contain a heteroatom. The hydrocarbylene group may be saturated or unsaturated and straight, branched or cyclic. Examples thereof are as exemplified above for $R^{203}$.

In formula (2), $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl.

In formula (2), d is an integer of 0 to 3.

Of the PAGs having formula (2), those having formula (2') are preferred.

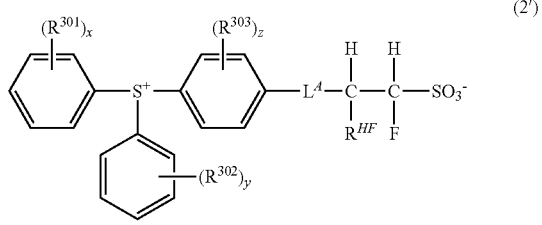

(2')

In formula (2'), $L^A$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ hydrocarbyl group which may contain a heteroatom. The hydrocarbyl group may be saturated or unsaturated and straight, branched or cyclic. Examples thereof are as exemplified above for $R^{111}$ in formula (1A'). The subscripts x and y are each independently an integer of 0 to 5, and z is an integer of 0 to 4.

Examples of the PAG having formula (2) are as exemplified for the PAG having formula (2) in JP-A 2017-026980.

Of the foregoing PAGs, those having an anion of formula (1A') or (1D) are especially preferred because of reduced acid diffusion and high solubility in the solvent. Also those having an anion of formula (2') are especially preferred because of extremely reduced acid diffusion.

Also a sulfonium or iodonium salt having an anion containing an iodized or brominated aromatic ring may be used as the PAG. Suitable are sulfonium and iodonium salts having the formulae (3-1) and (3-2).

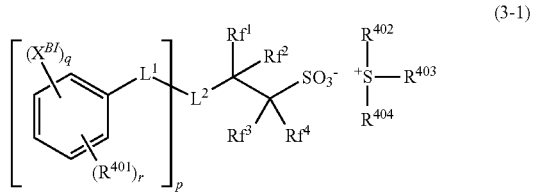

(3-1)

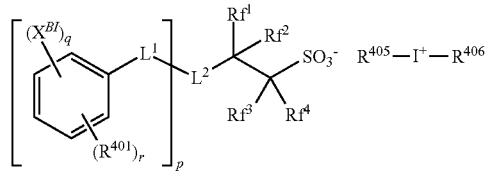

(3-2)

In formulae (3-1) and (3-2), p is an integer of 1 to 3, q is an integer of 1 to 5, and r is an integer of 0 to 3, and 1≤q+r≤5. Preferably, q is 1, 2 or 3, more preferably 2 or 3, and r is 0, 1 or 2.

In formulae (3-1) and (3-2), $X^{BI}$ is iodine or bromine, and may be the same or different when p and/or q is 2 or more.

$L^1$ is a single bond, ether bond, ester bond, or a $C_1$-$C_6$ saturated hydrocarbylene group which may contain an ether bond or ester bond. The saturated hydrocarbylene group may be straight, branched or cyclic.

$L^2$ is a single bond or a $C_1$-$C_{20}$ divalent linking group when p is 1, and a $C_1$-$C_{20}$ tri- or tetravalent linking group which may contain oxygen, sulfur or nitrogen when p is 2 or 3.

$R^{401}$ is a hydroxyl group, carboxyl group, fluorine, chlorine, bromine, amino group, or a $C_1$-$C_{20}$ saturated hydrocarbyl, $C_1$-$C_{20}$ saturated hydrocarbyloxy, $C_2$-$C_{20}$ saturated hydrocarbylcarbonyl, $C_2$-$C_{20}$ saturated hydrocarbyloxycarbonyl, $C_2$-$C_{20}$ saturated hydrocarbylcarbonyloxy or $C_1$-$C_{20}$ saturated hydrocarbylsulfonyloxy group, which may contain fluorine, chlorine, bromine, hydroxyl, amino or ether bond, or —N($R^{401A}$)($R^{401B}$), —N($R^{401C}$)—C(=O)—$R^{401D}$ or —N($R^{401C}$)—C(=O)—O—$R^{401D}$. $R^{401A}$ and $R^{401B}$ are each independently hydrogen or a $C_1$-$C_6$ saturated hydrocarbyl group. $R^{401C}$ is hydrogen or a $C_1$-$C_6$ saturated hydrocarbyl group which may contain halogen, hydroxyl, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. $R^{401D}$ is a $C_1$-$C_{16}$ aliphatic hydrocarbyl group, $C_6$-$C_{14}$ aryl group or $C_7$-$C_{15}$ aralkyl group, which may contain halogen, hydroxyl, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. The aliphatic hydrocarbyl group may be saturated or unsaturated and straight, branched or cyclic. The saturated hydrocarbyl, saturated hydrocarbyloxy, saturated hydrocarbyloxycarbonyl, saturated hydrocarbylcarbonyl, and saturated hydrocarbylcarbonyloxy groups may be straight, branched or cyclic. Groups $R^{401}$ may be the same or different when p and/or r is 2 or more. Of these, $R^{401}$ is preferably hydroxyl, —N($R^{401C}$)—C(=O)—$R^{401D}$, —N($R^{401C}$)—C(=O)—O—$R^{401D}$, fluorine, chlorine, bromine, methyl or methoxy.

In formulae (3-1) and (3-2), $Rf^1$ to $Rf^4$ are each independently hydrogen, fluorine or trifluoromethyl, at least one of $Rf^1$ to $Rf^4$ is fluorine or trifluoromethyl, or $Rf^1$ and $Rf^2$, taken together, may form a carbonyl group. Preferably, both $Rf^3$ and $Rf^4$ are fluorine.

$R^{402}$ to $R^{406}$ are each independently halogen or a $C_1$-$C_{20}$ hydrocarbyl group which may contain a heteroatom. The hydrocarbyl group may be saturated or unsaturated and straight, branched or cyclic. Examples thereof include those exemplified above for the hydrocarbyl groups $R^{101}$ to $R^{105}$ in formulae (1-1) and (1-2). In these groups, some or all of the hydrogen atoms may be substituted by hydroxyl, carboxyl, halogen, cyano, nitro, mercapto, sultone, sulfone, or sulfonium salt-containing moieties, and some carbon may be replaced by an ether bond, ester bond, carbonyl moiety, amide bond, carbonate moiety or sulfonic acid ester bond. $R^{402}$ and $R^{403}$ may bond together to form a ring with the sulfur atom to which they are attached. Exemplary rings are the same as described above for the ring that $R^{101}$ and $R^{102}$ in formula (1-1), taken together, form with the sulfur atom to which they are attached.

Examples of the cation in the sulfonium salt having formula (3-1) include those exemplified above as the cation in the sulfonium salt having formula (1-1). Examples of the cation in the iodonium salt having formula (3-2) include those exemplified above as the cation in the iodonium salt having formula (1-2).

Examples of the anion in the onium salts having formulae (3-1) and (3-2) are shown below, but not limited thereto. Herein $X^{BI}$ is as defined above.

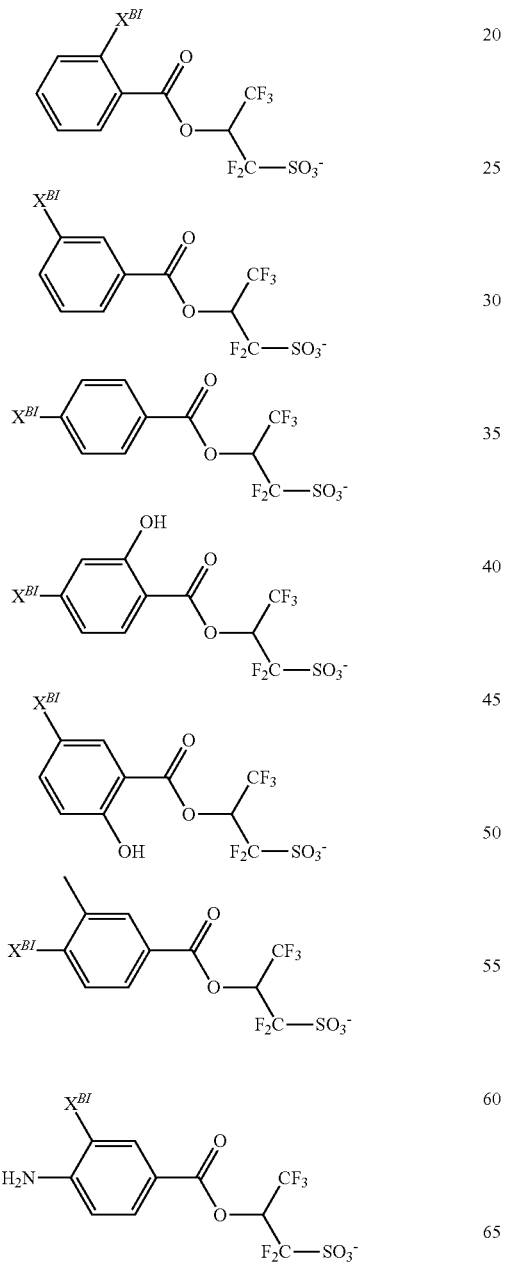

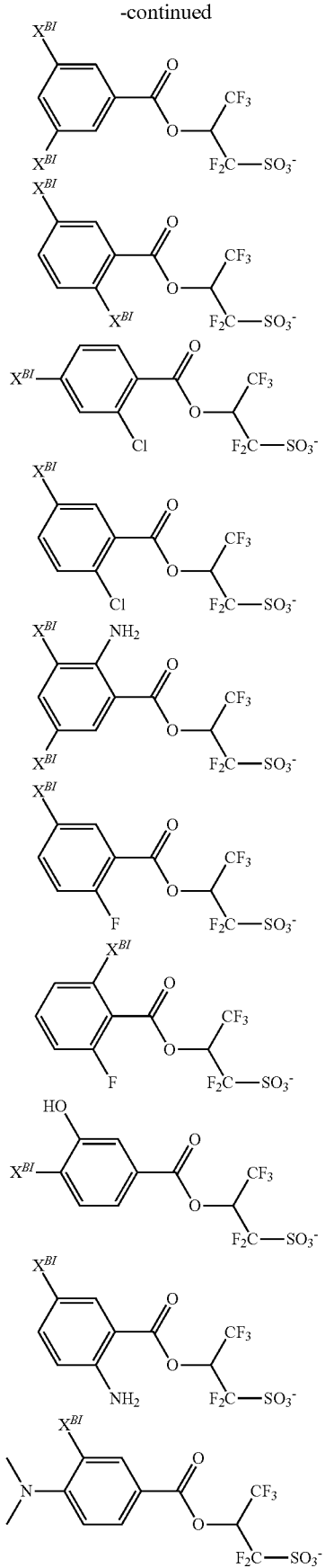

107 -continued
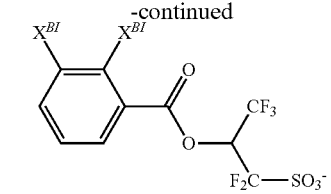
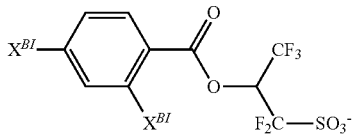
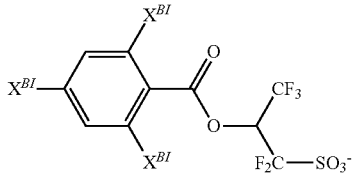
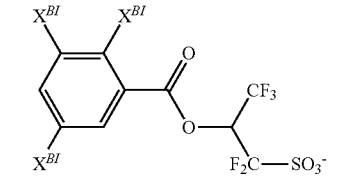
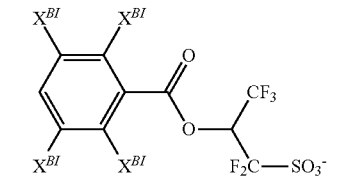
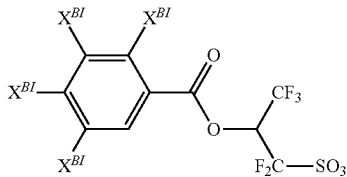
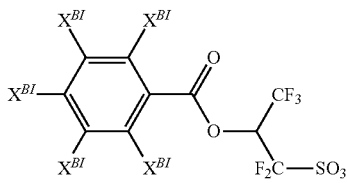
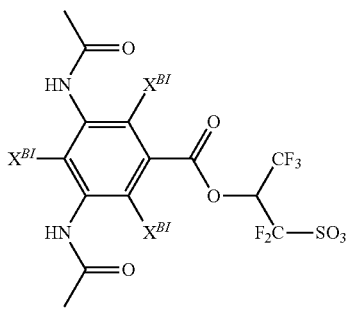
108 -continued
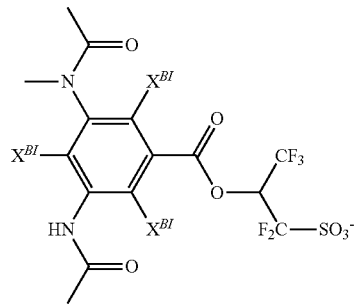
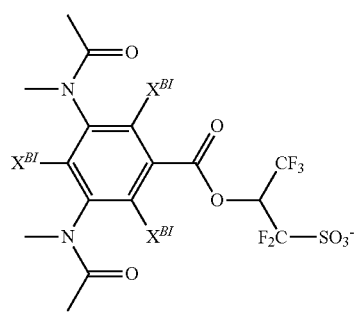
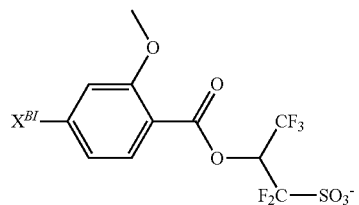
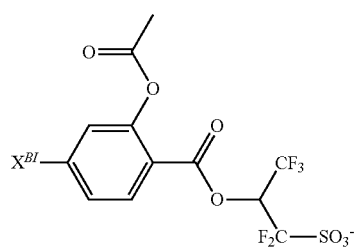
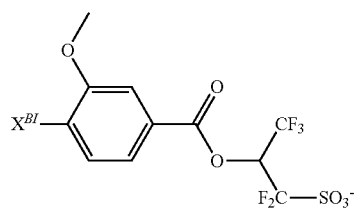
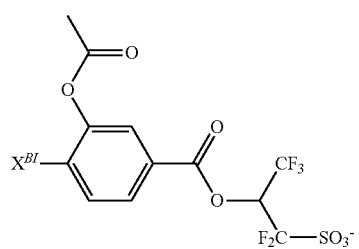

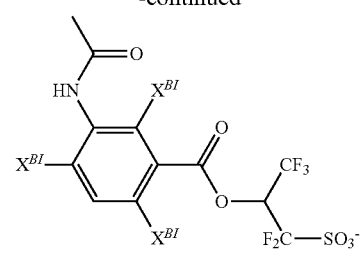
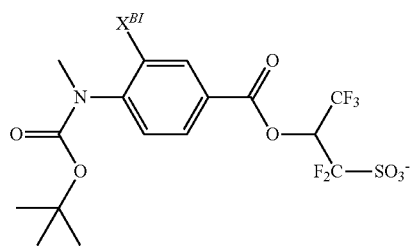
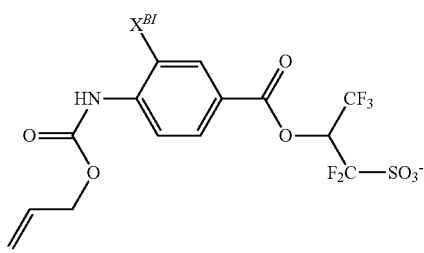
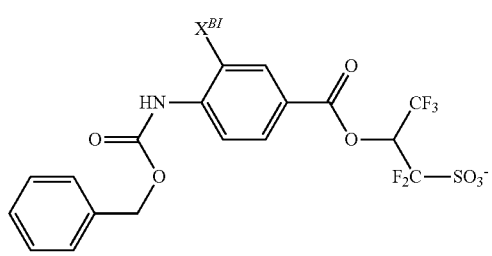
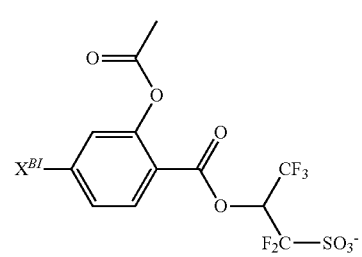
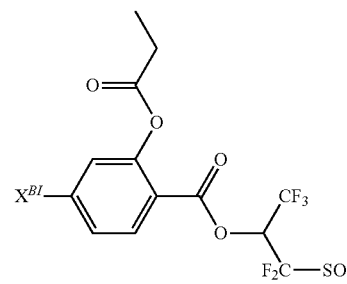
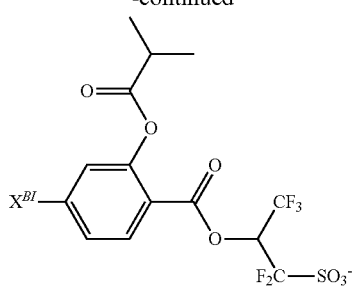
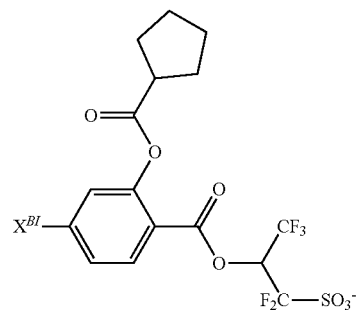
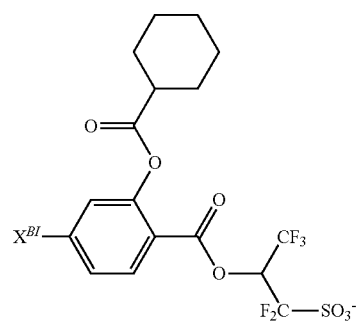
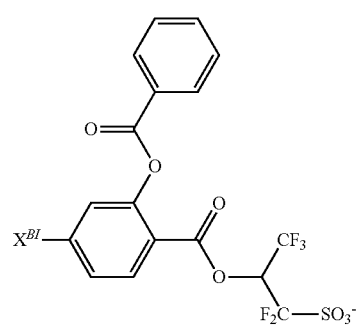
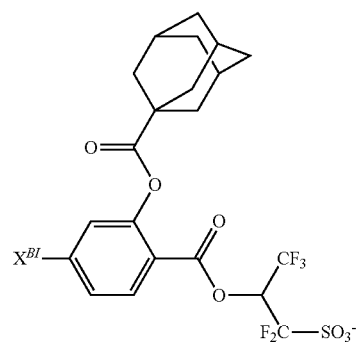

111
-continued
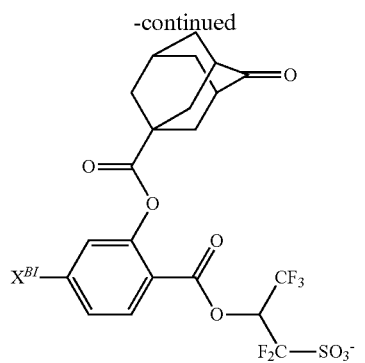
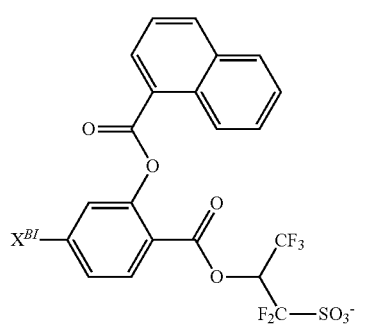
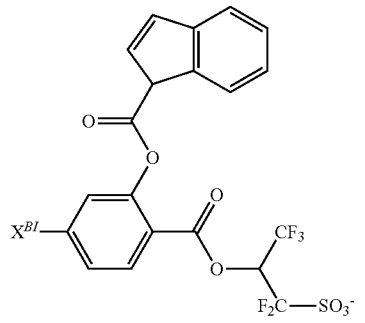
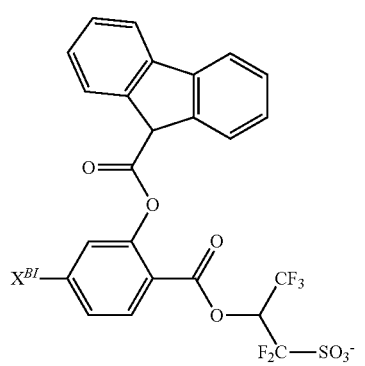
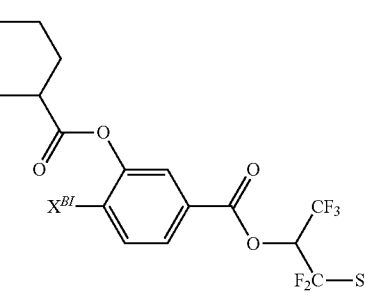
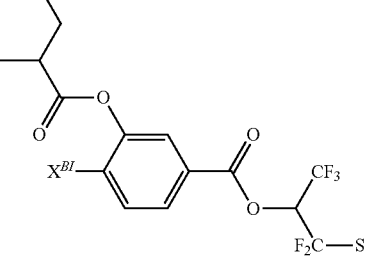
112
-continued
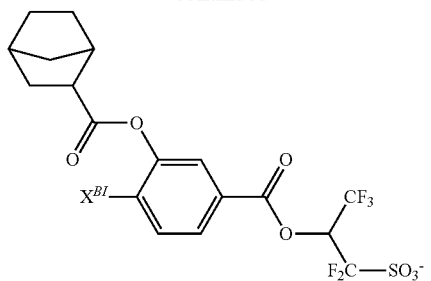
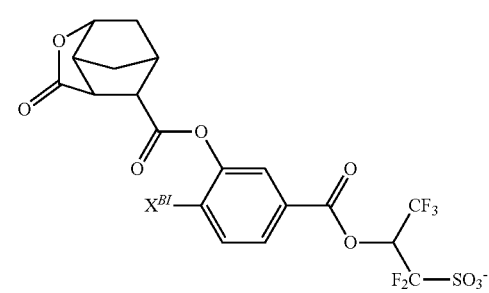
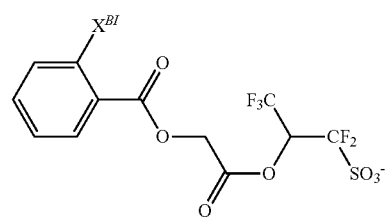
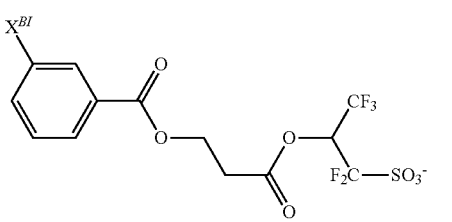
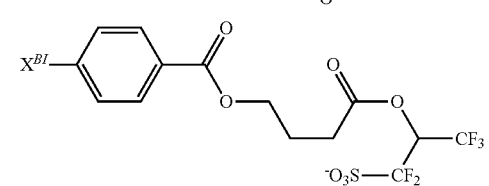
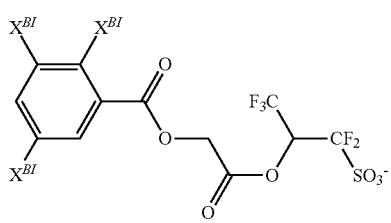
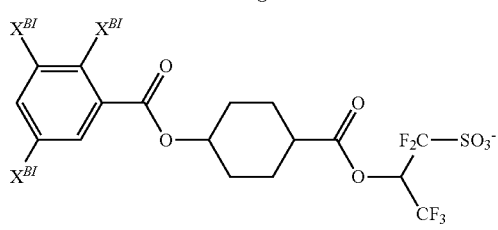

-continued
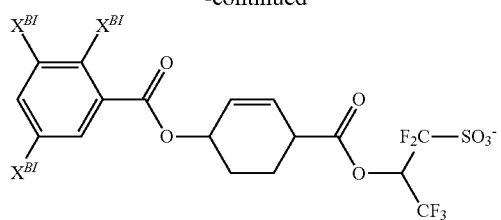
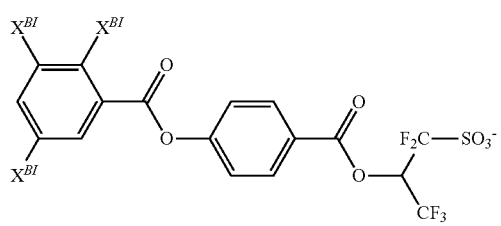
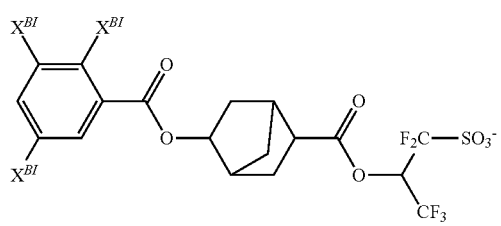
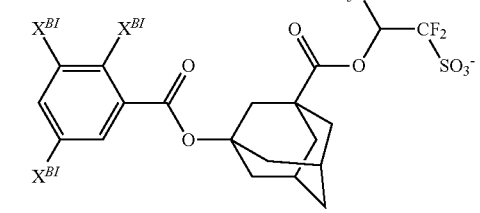
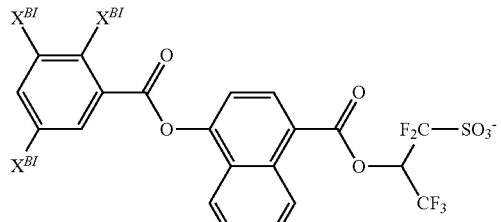
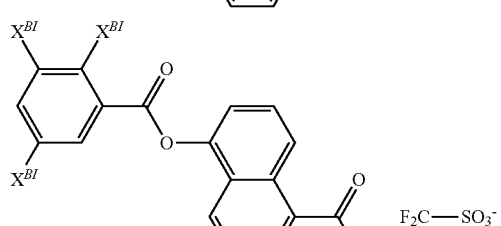
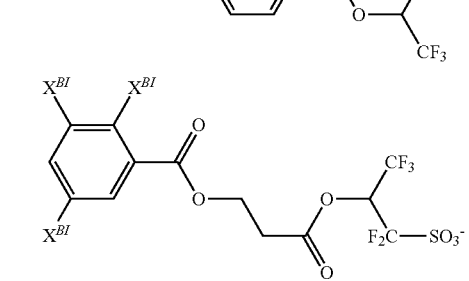
-continued
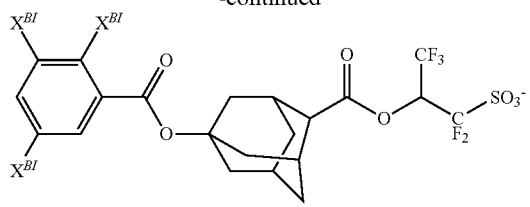
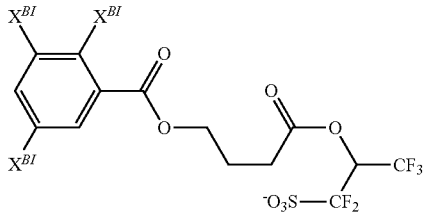
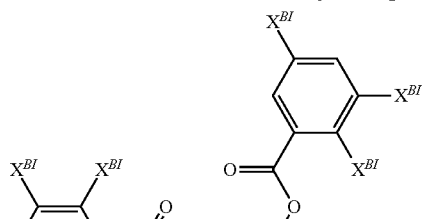
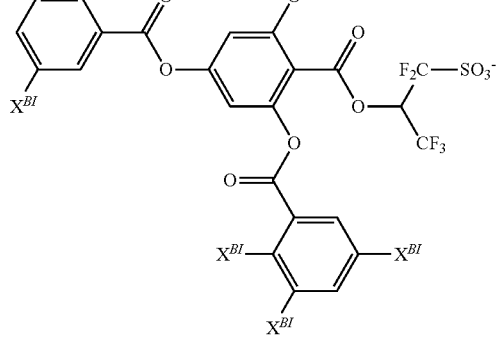
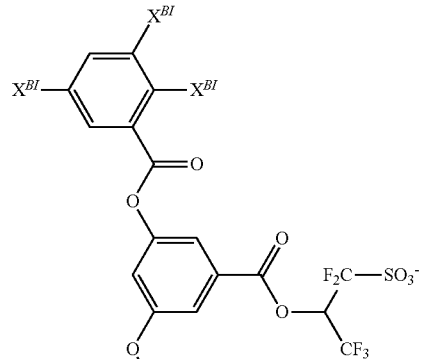
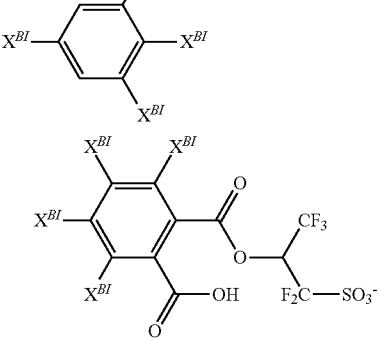

115
-continued
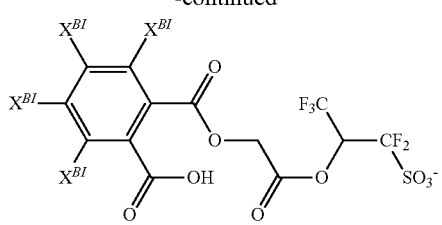
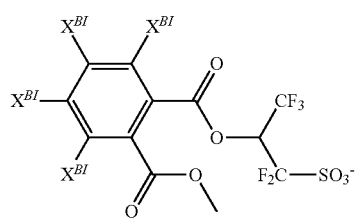
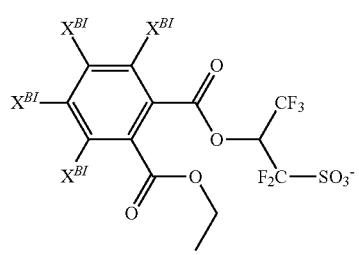
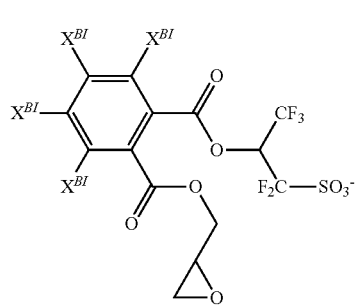
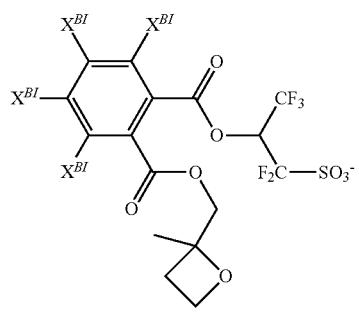
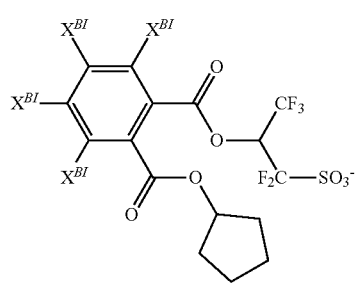
116
-continued
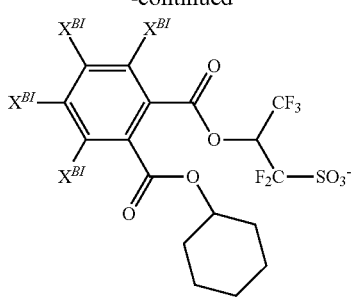
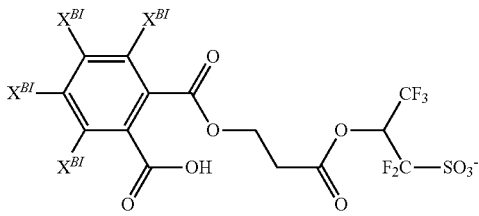
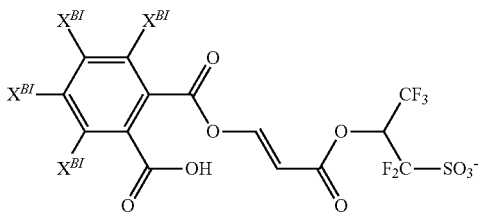
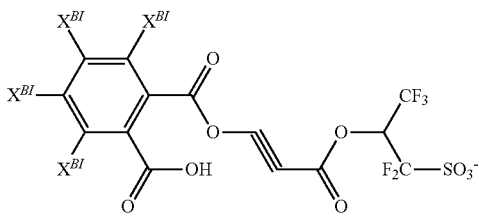
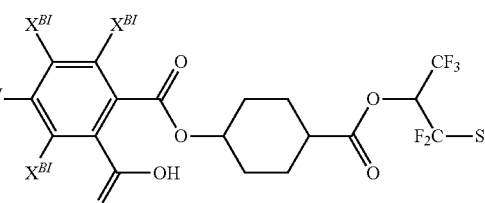
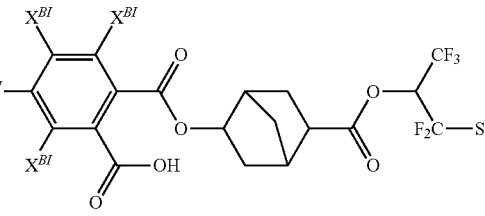
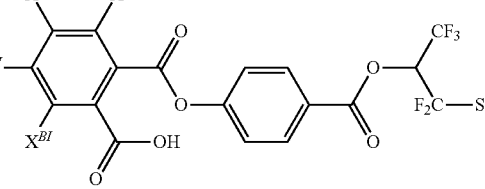

117
-continued
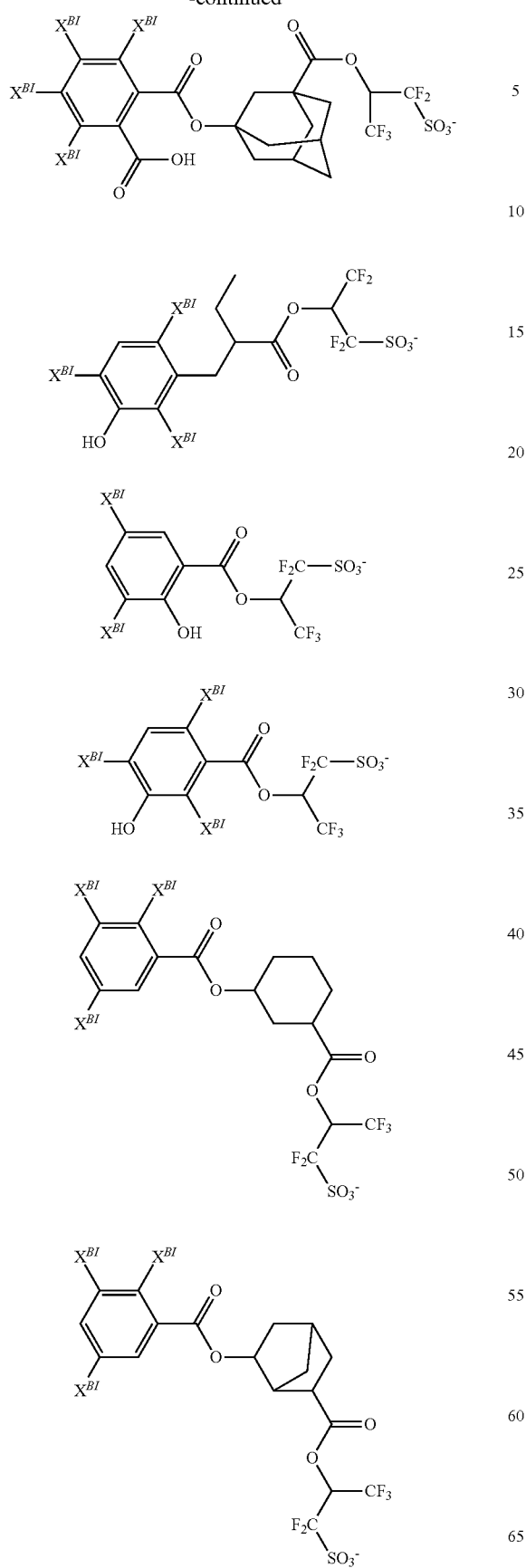
118
-continued
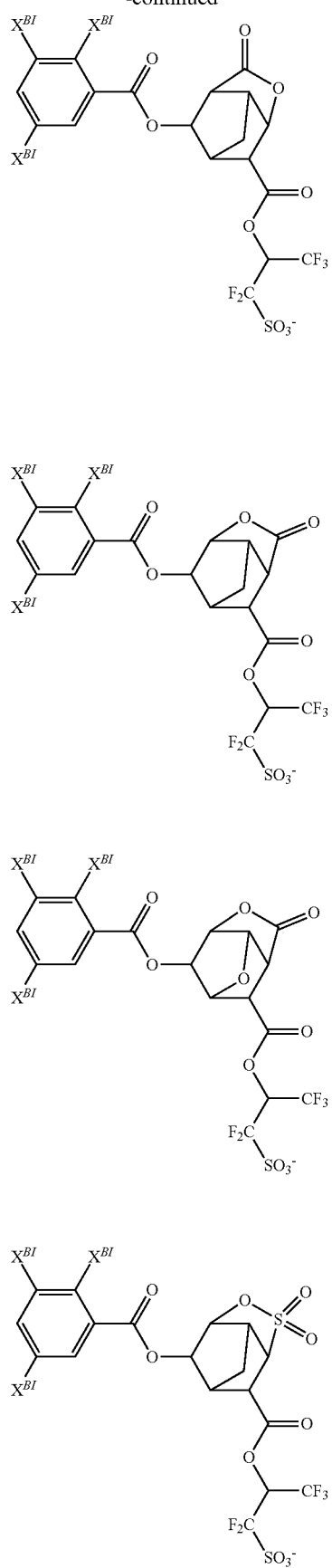

119
-continued
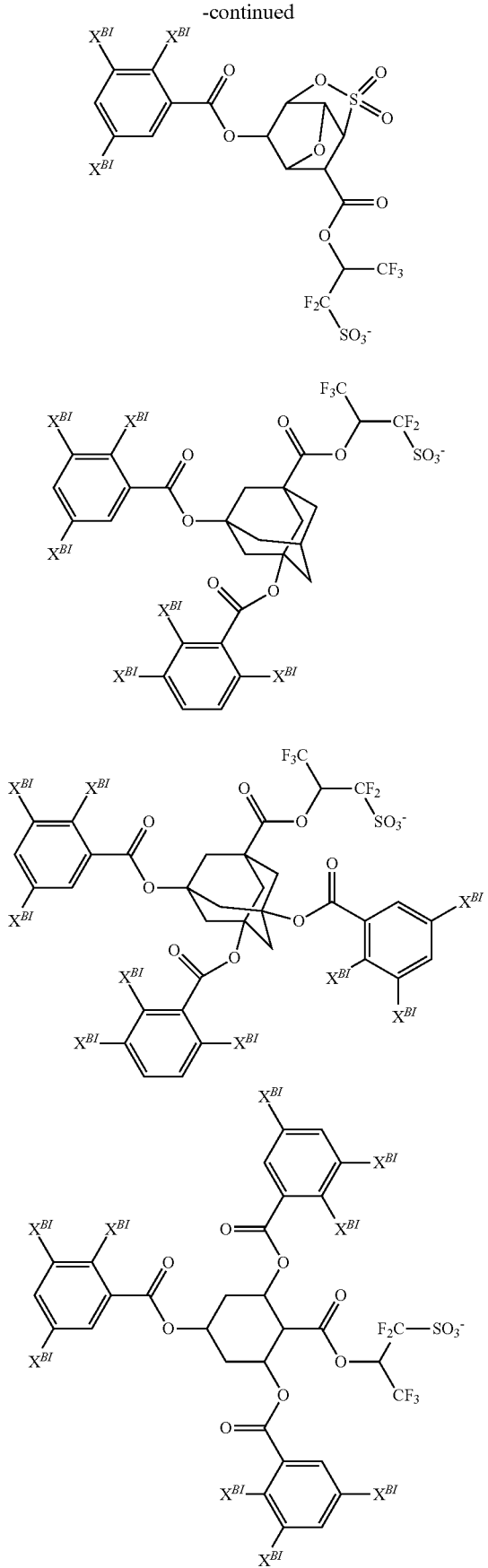
120
-continued
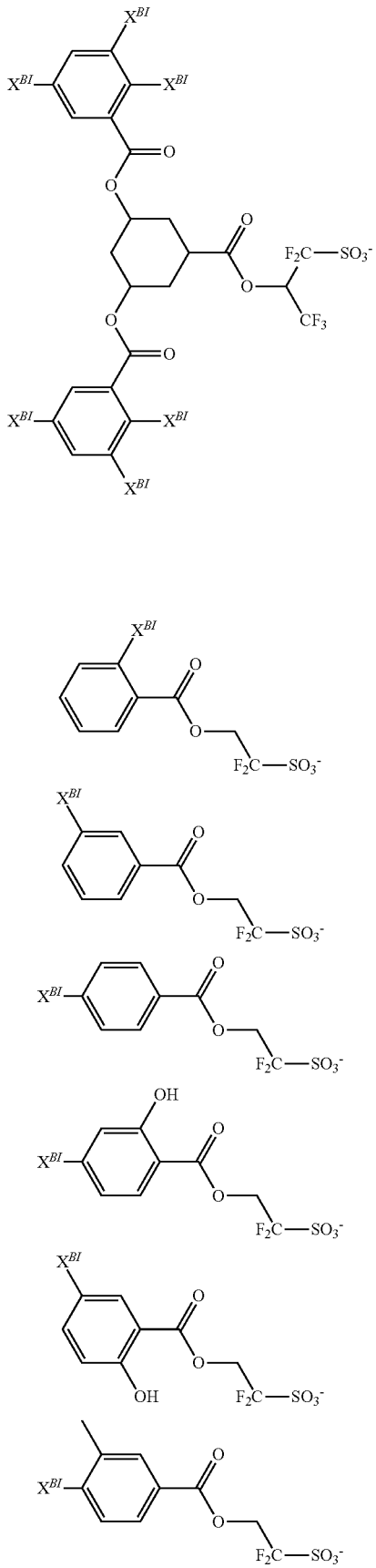

121
-continued
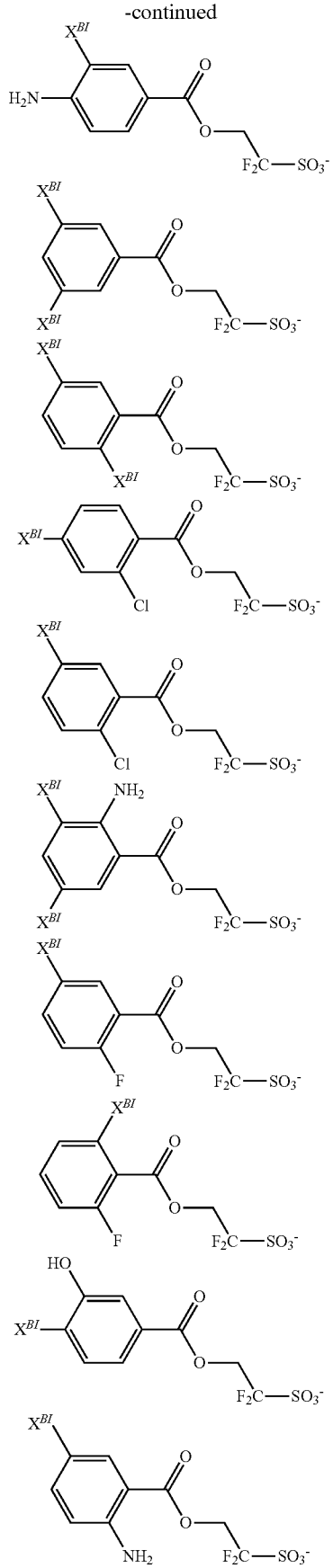
122
-continued
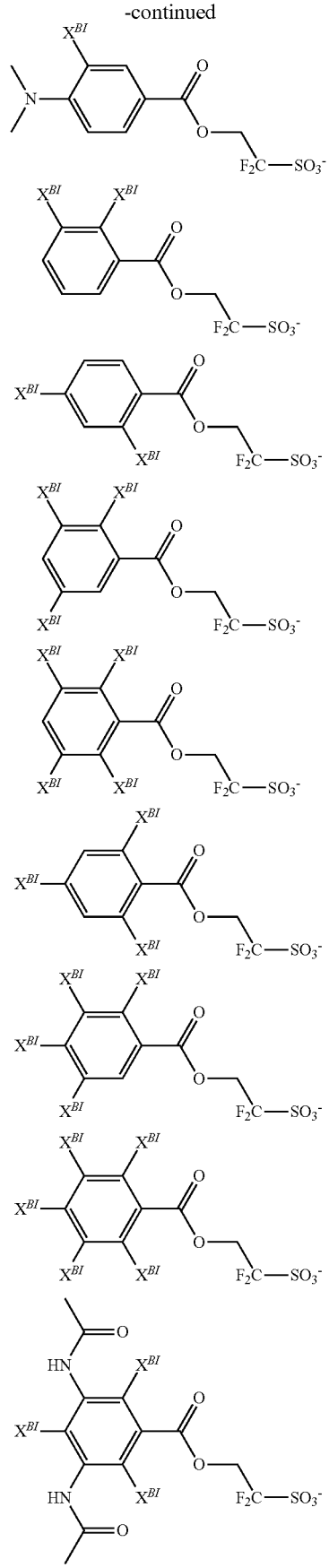

123
-continued
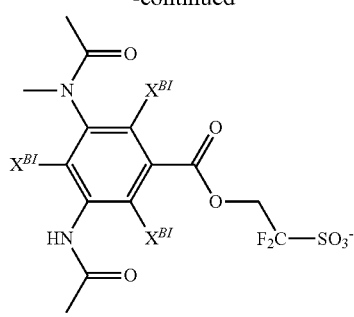
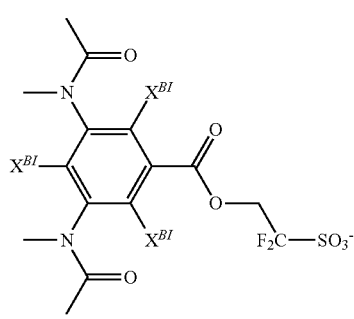
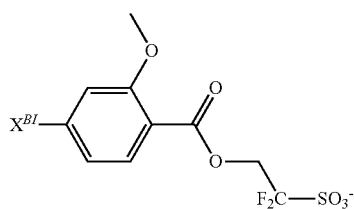
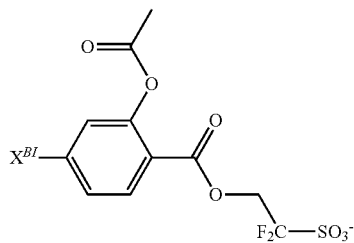
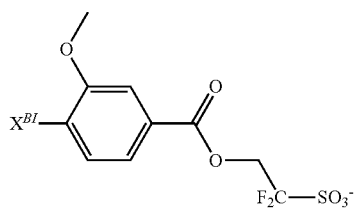
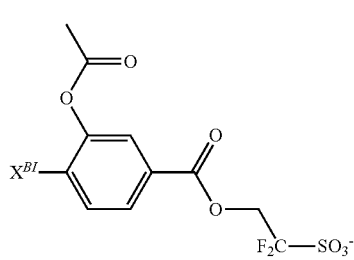
124
-continued
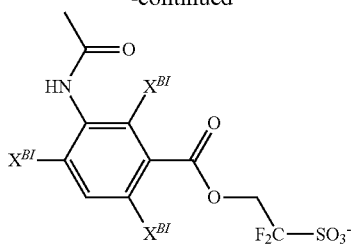
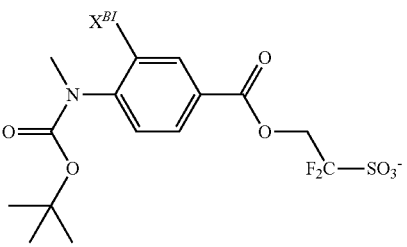
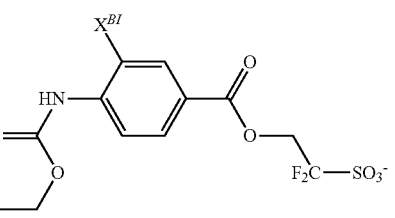
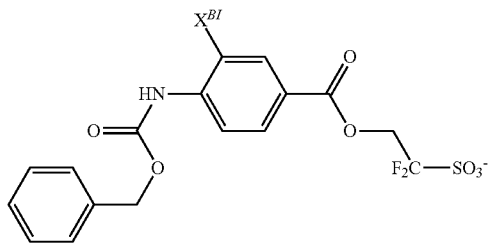
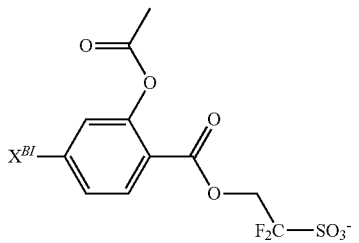
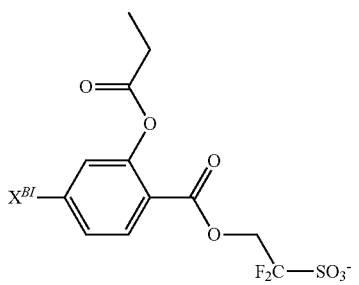

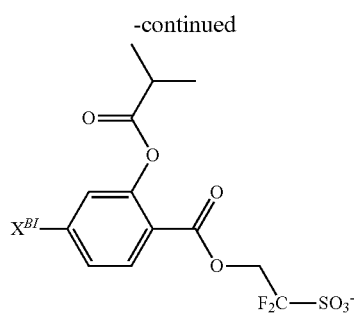
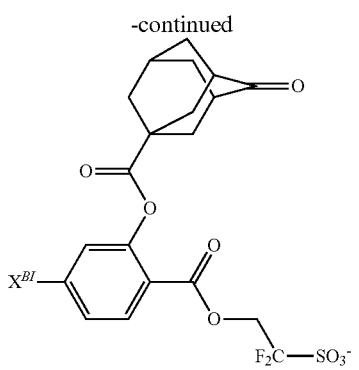

127
-continued
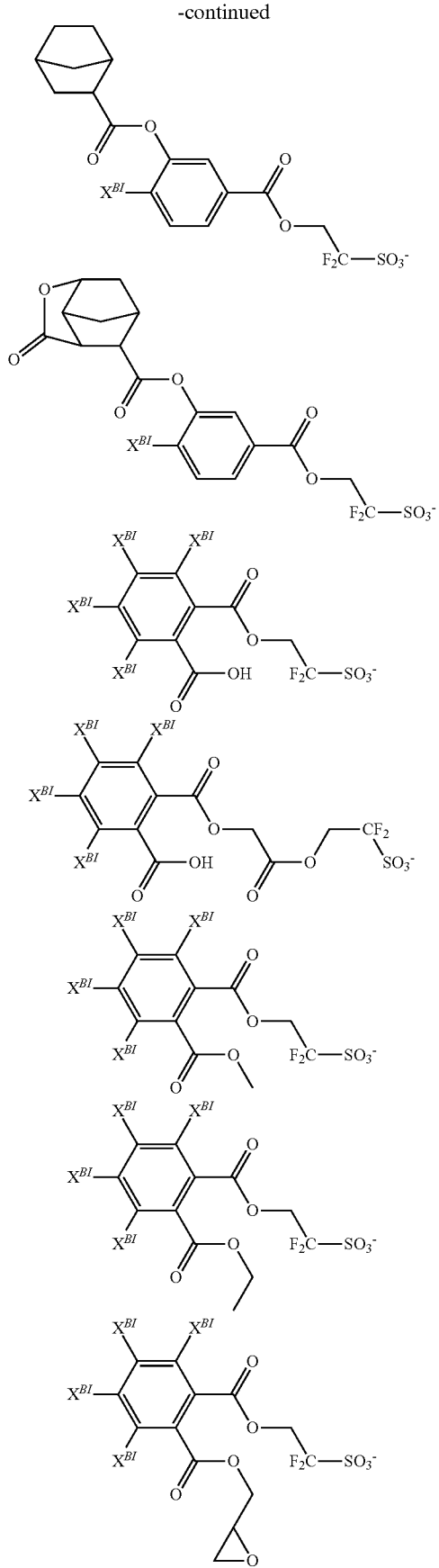
128
-continued
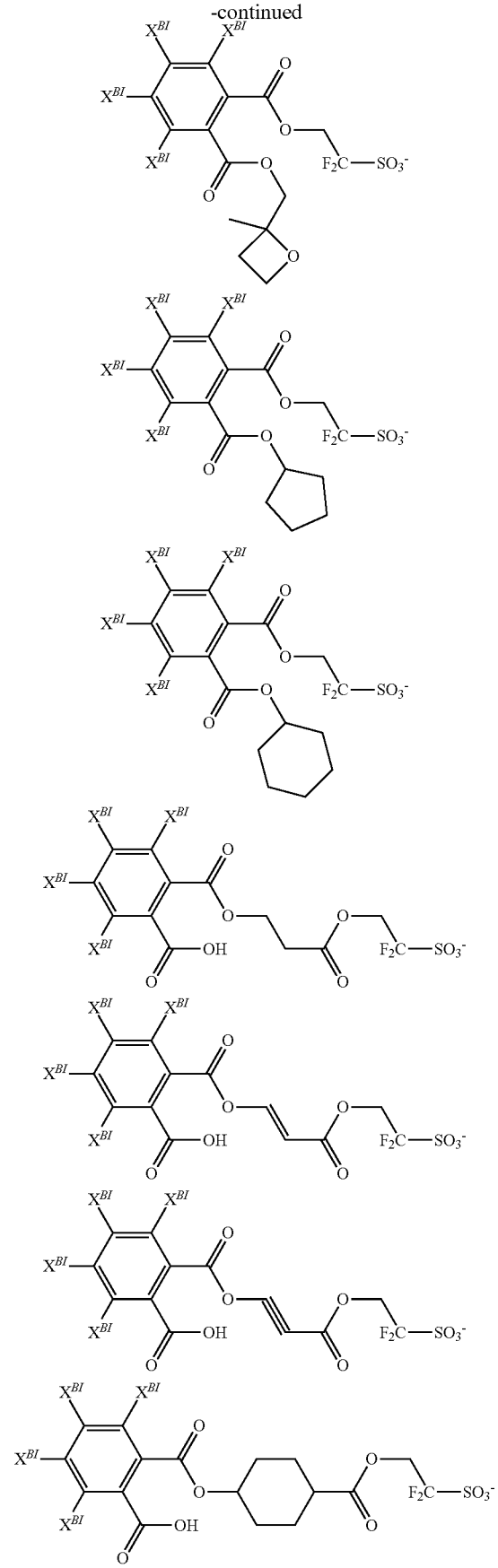

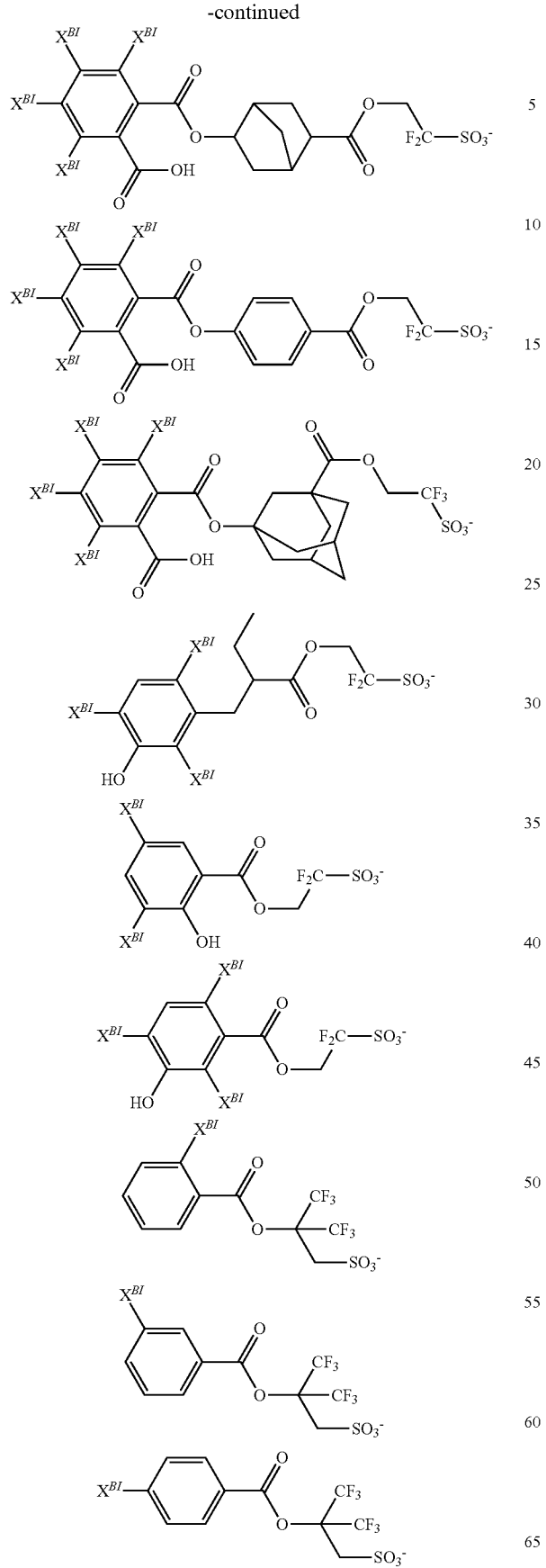
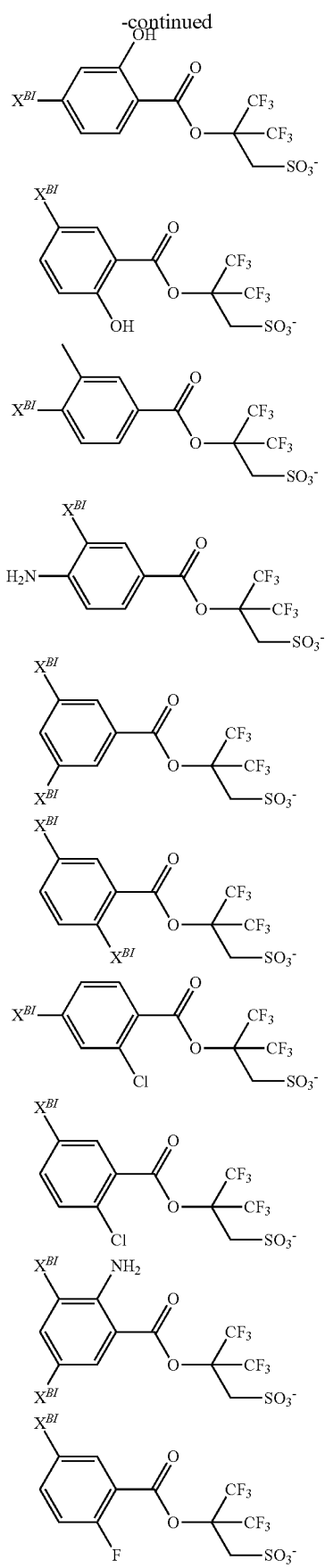

131
-continued
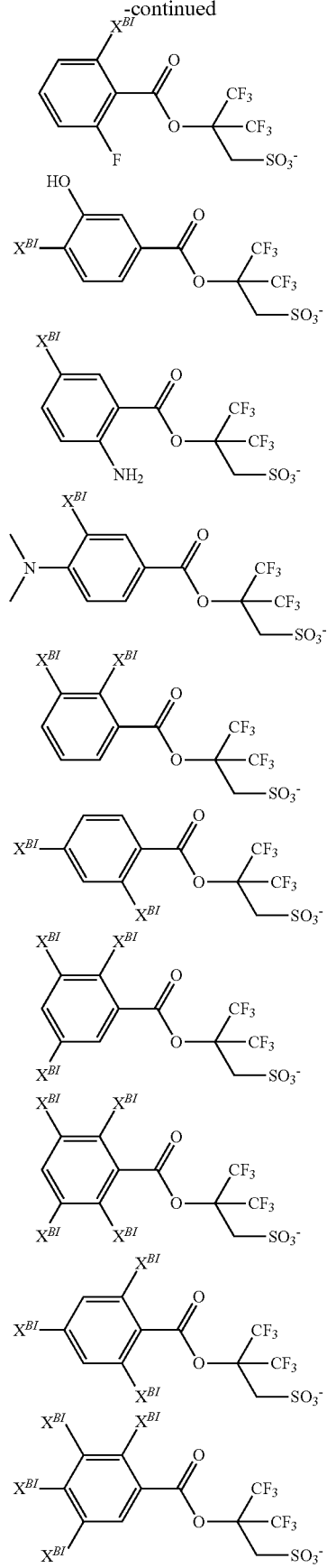
132
-continued
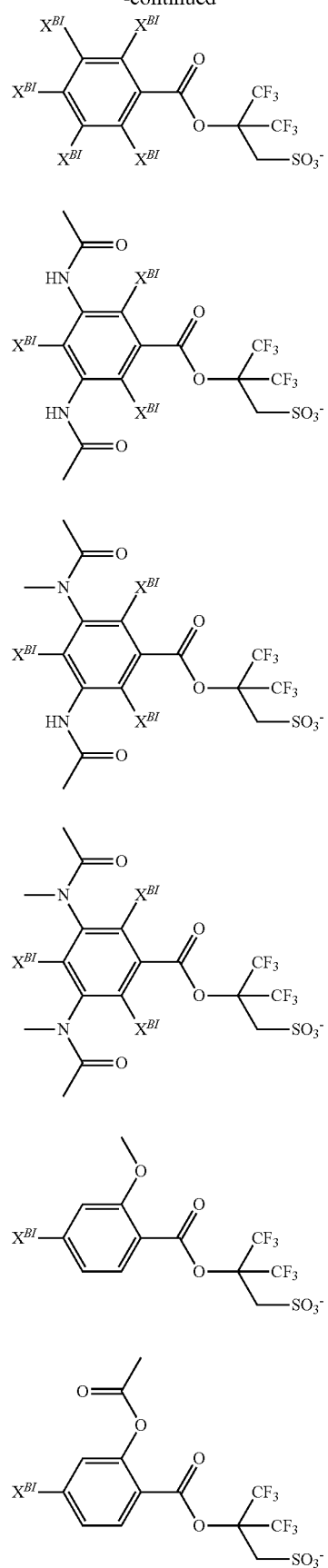

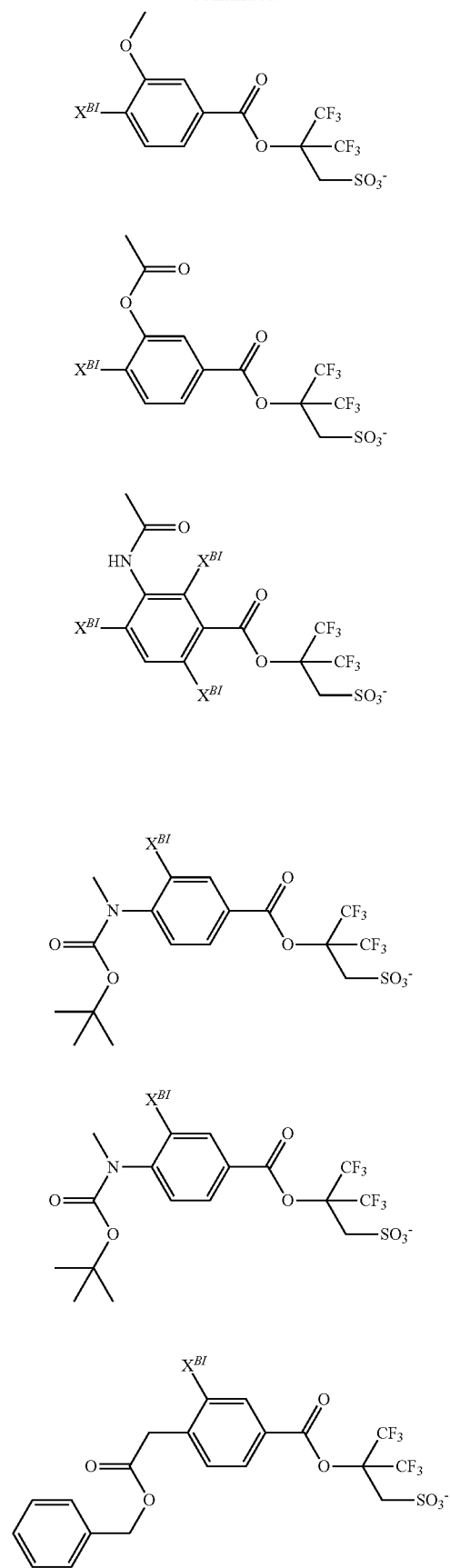
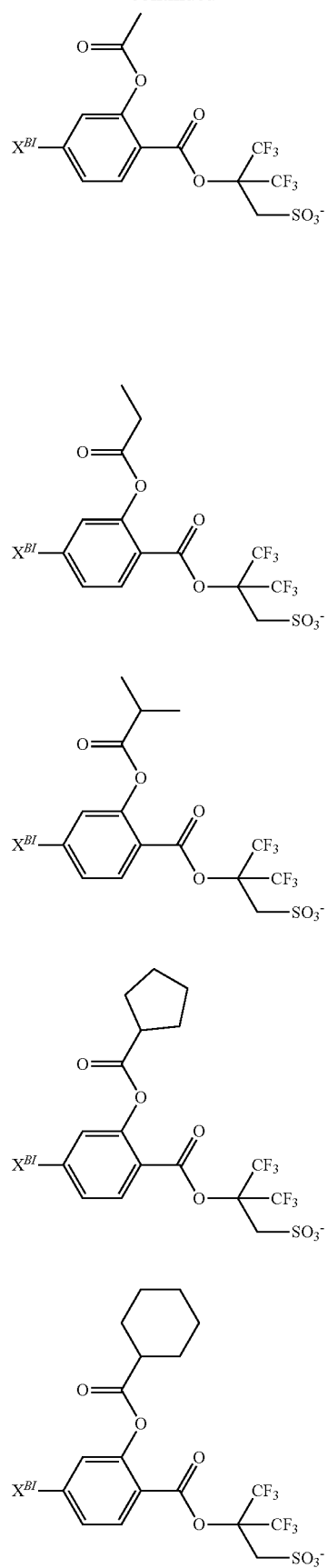

135
-continued
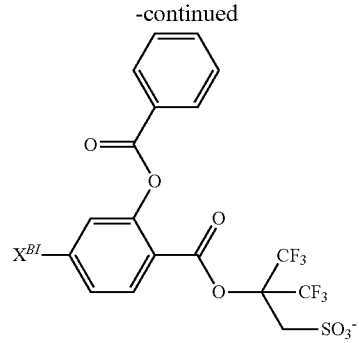
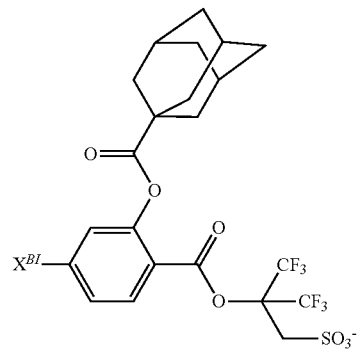
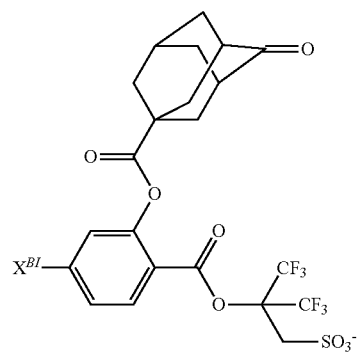
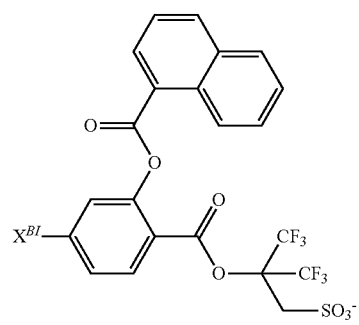
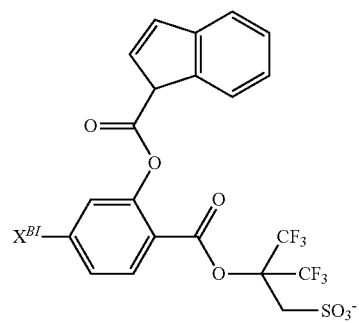
136
-continued
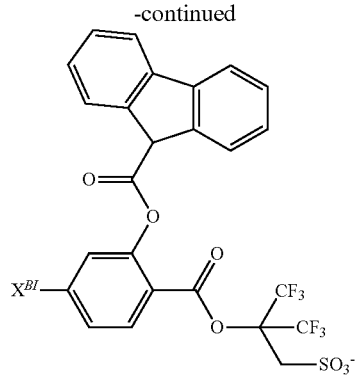
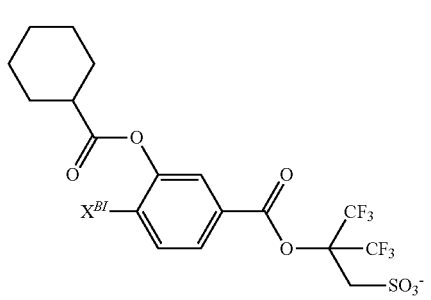
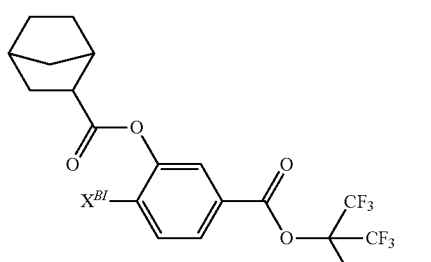
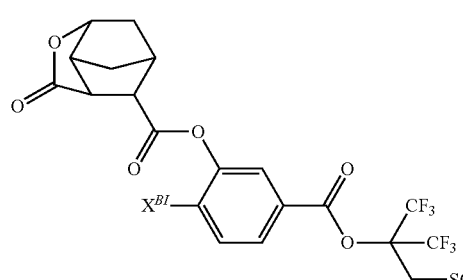
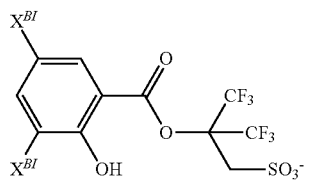
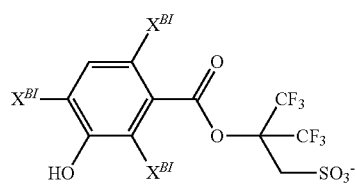

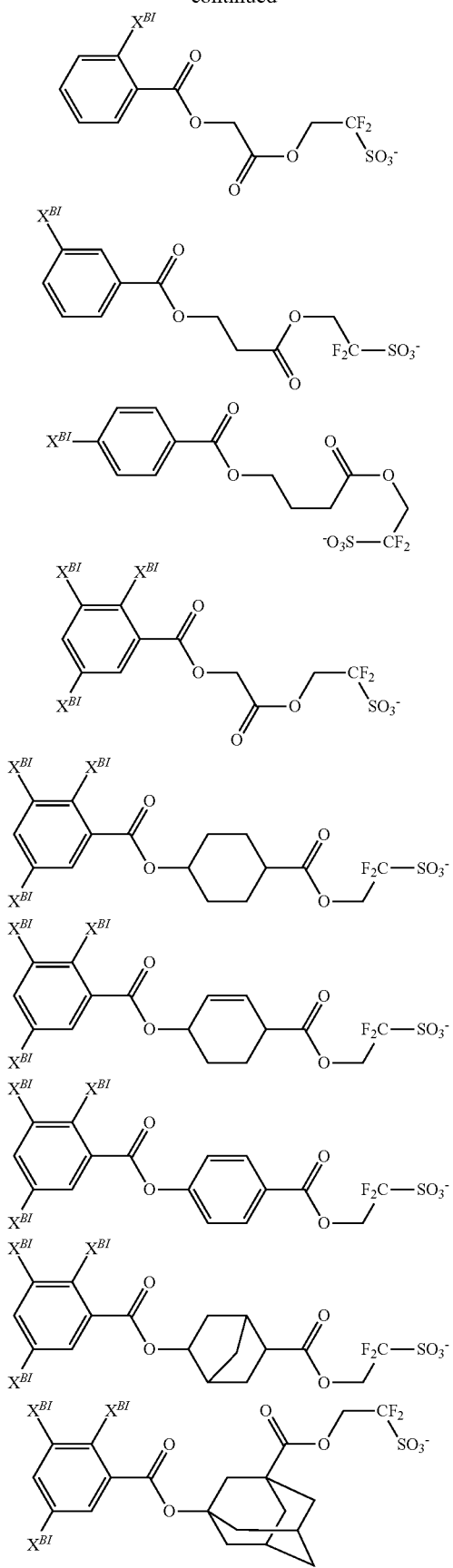
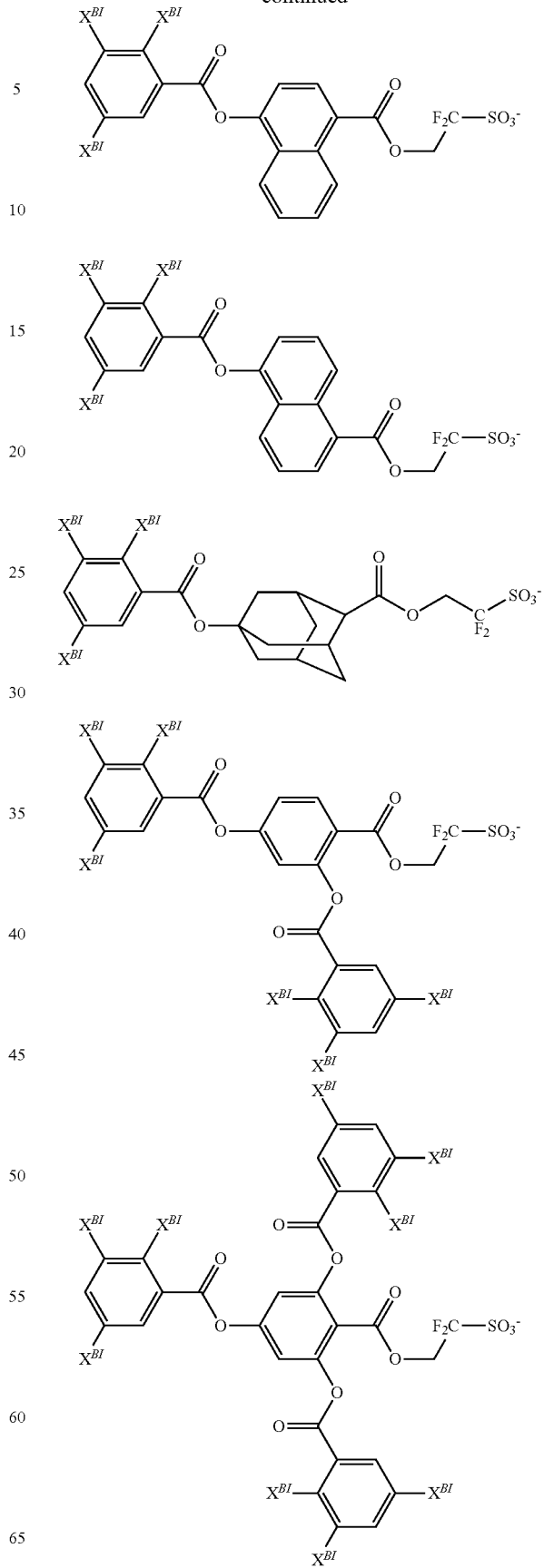

-continued
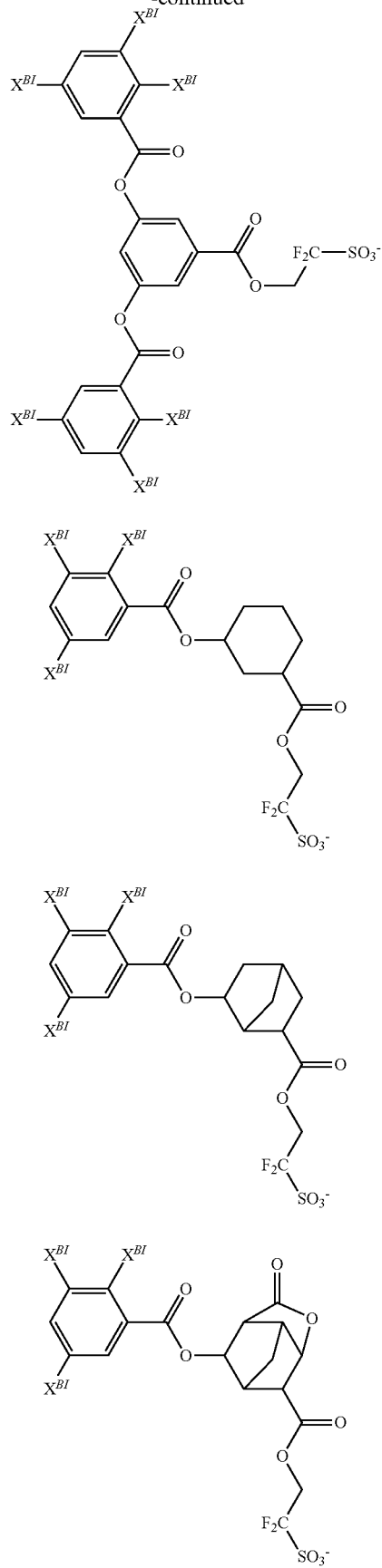
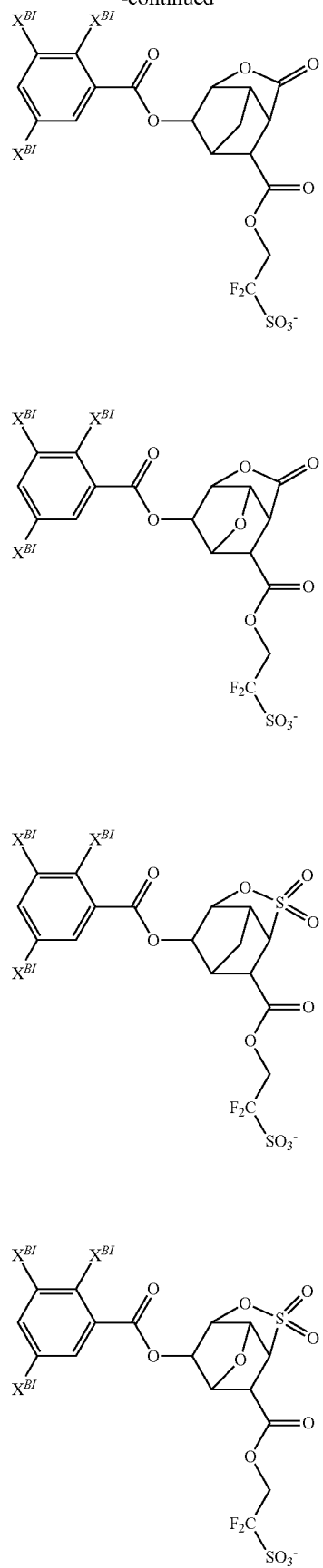

141
-continued
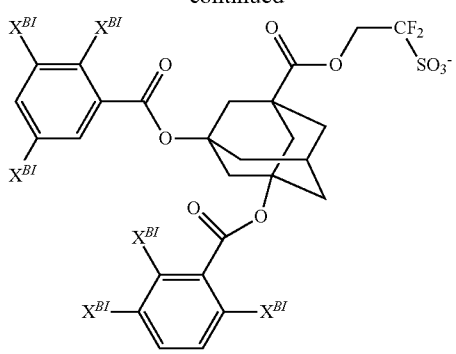
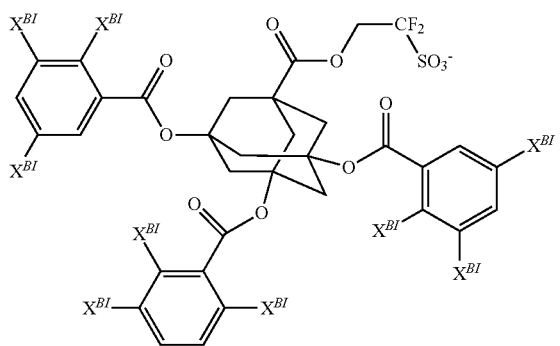
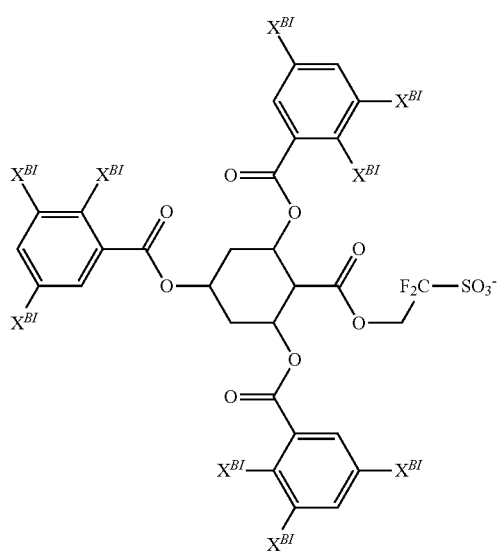
142
-continued
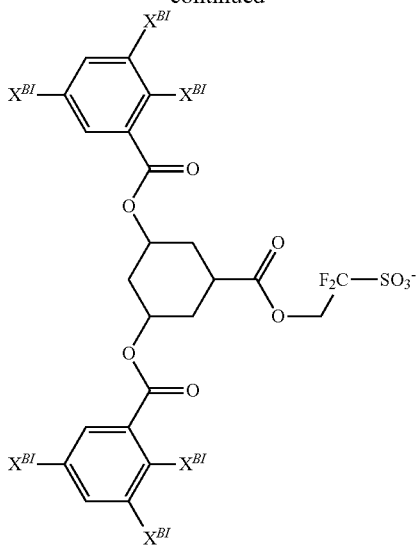
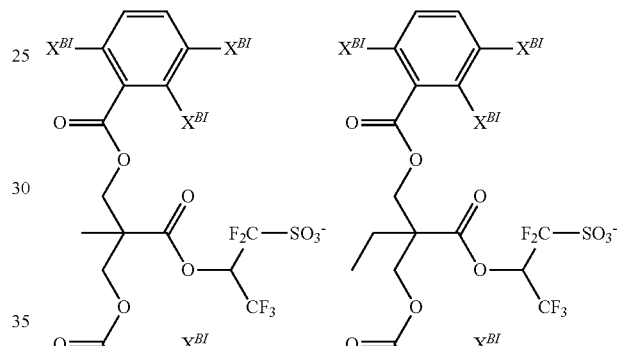
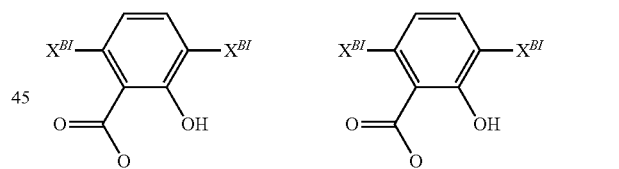
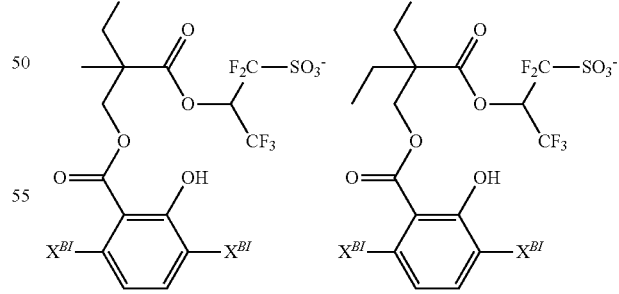
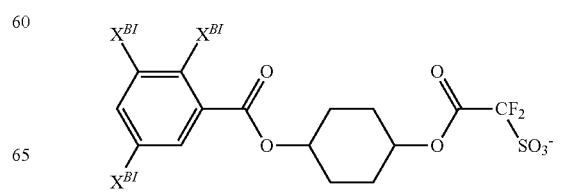

-continued
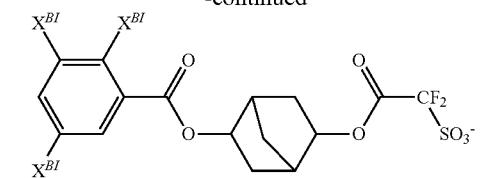
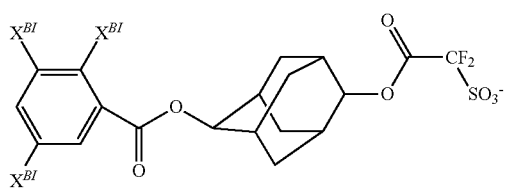
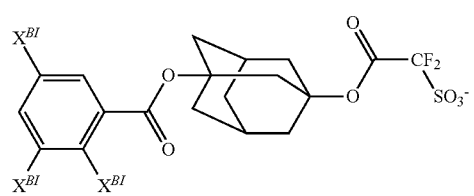
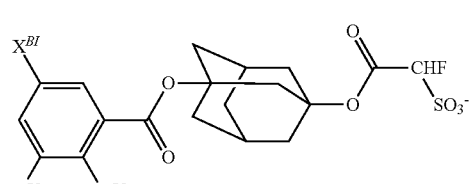
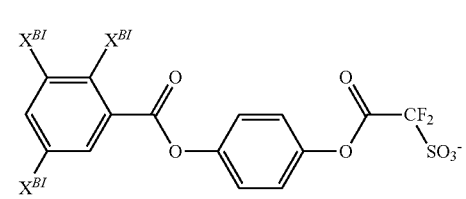
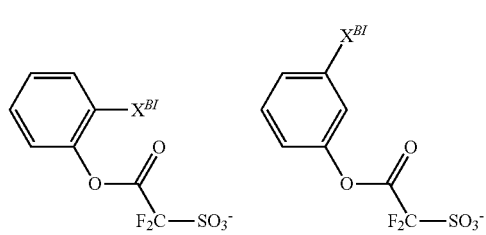
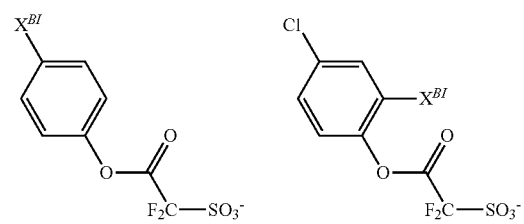
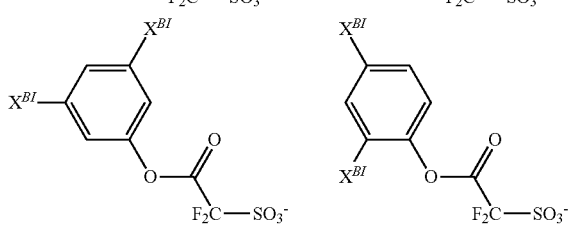
-continued
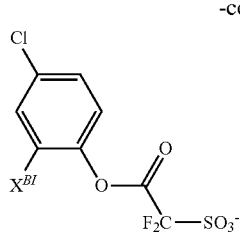
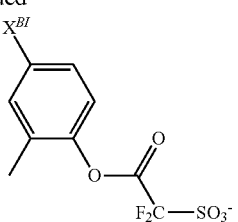
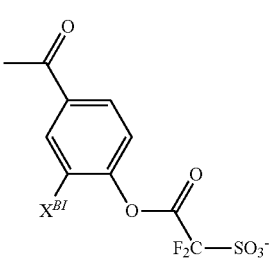
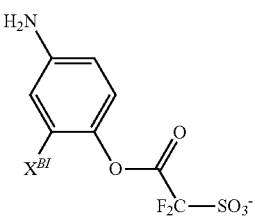
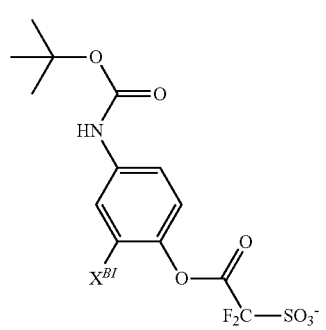
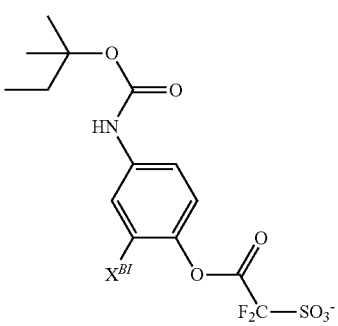
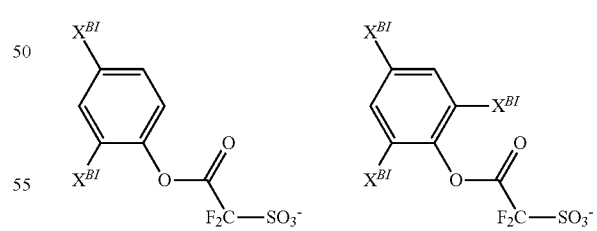
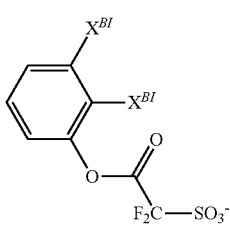

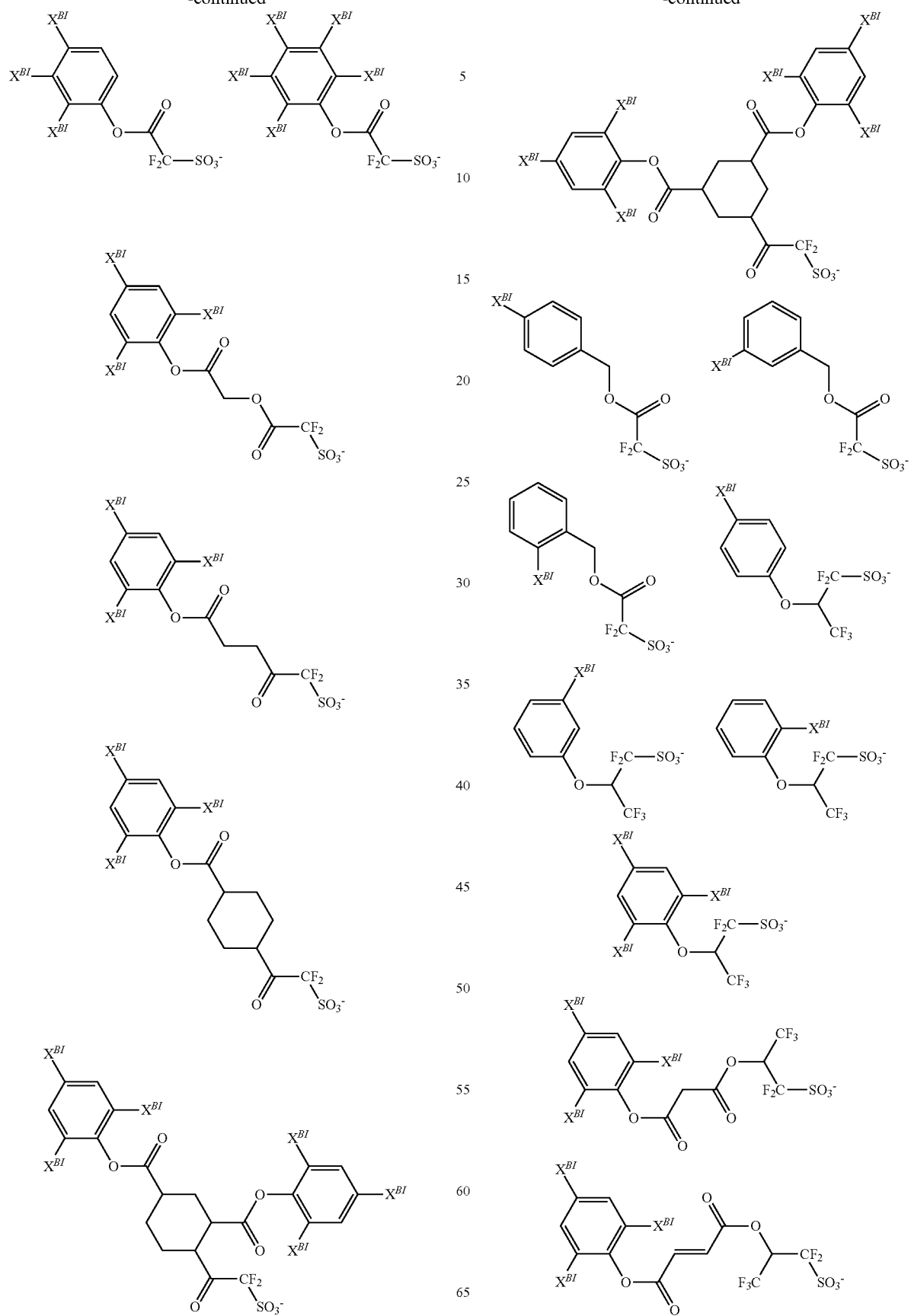

-continued
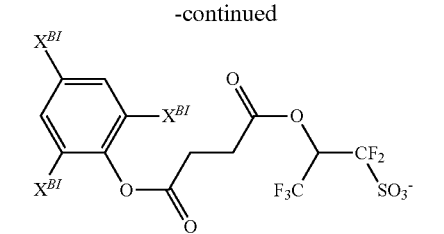
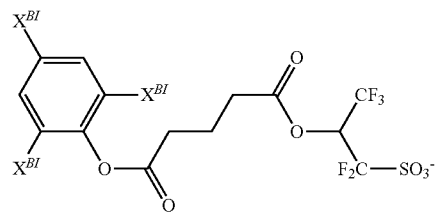
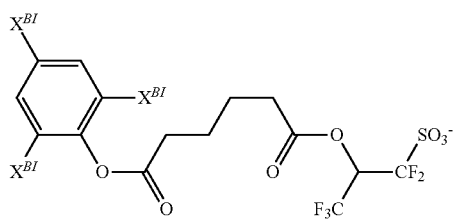
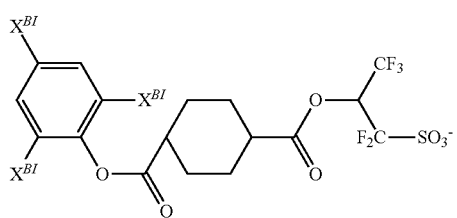
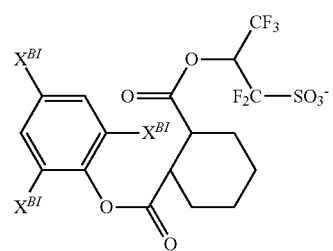
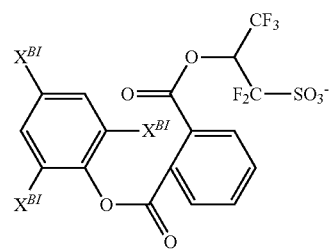
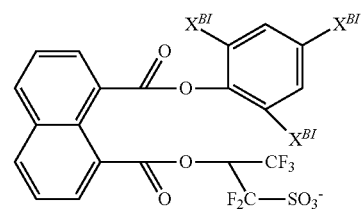
-continued
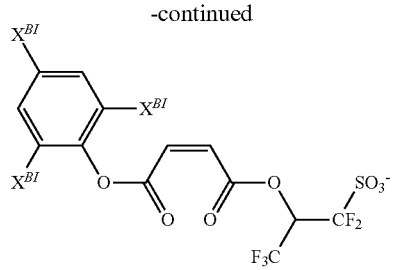
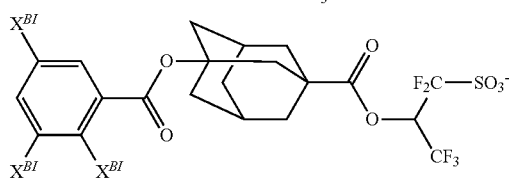
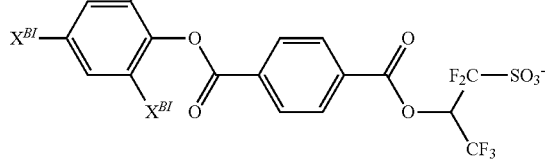
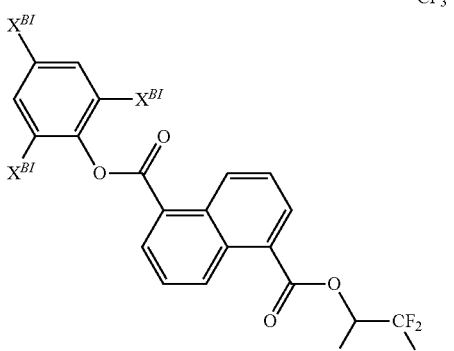
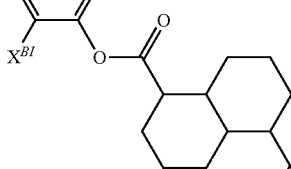
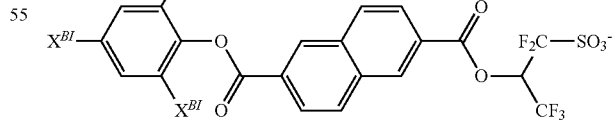
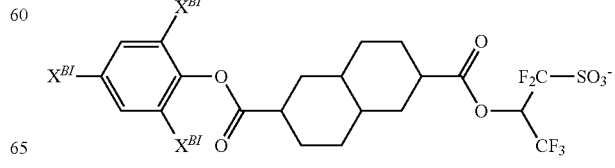

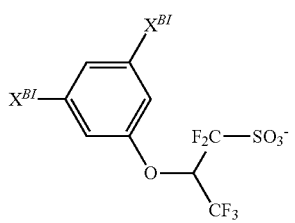
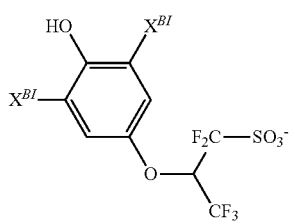
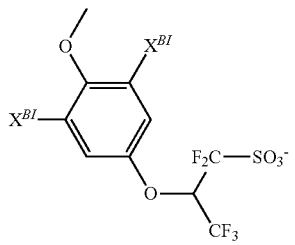
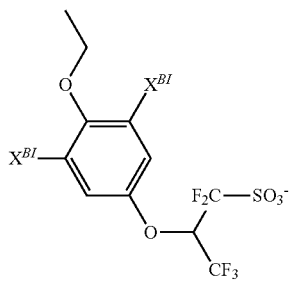
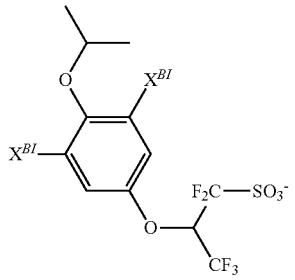
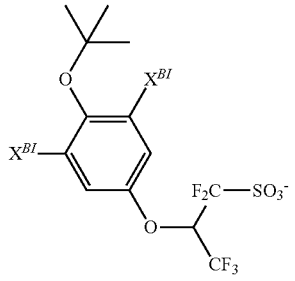
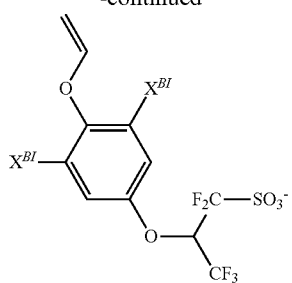
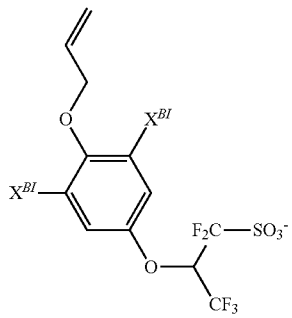
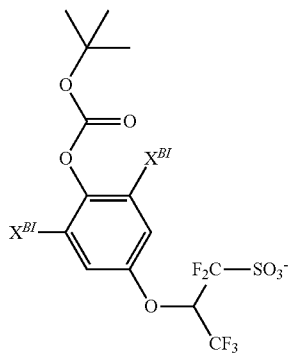
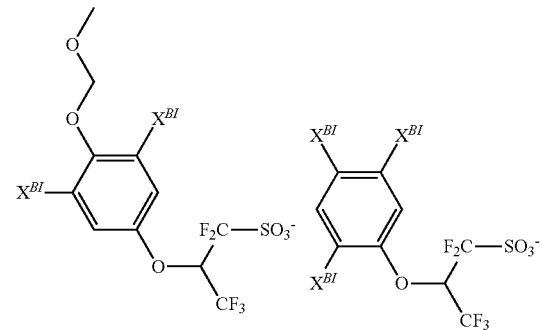
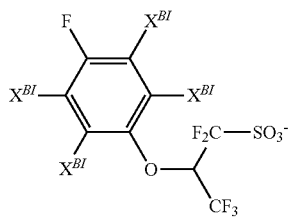
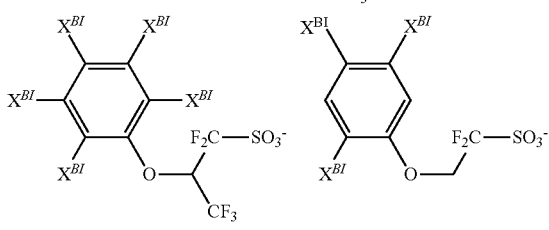

-continued
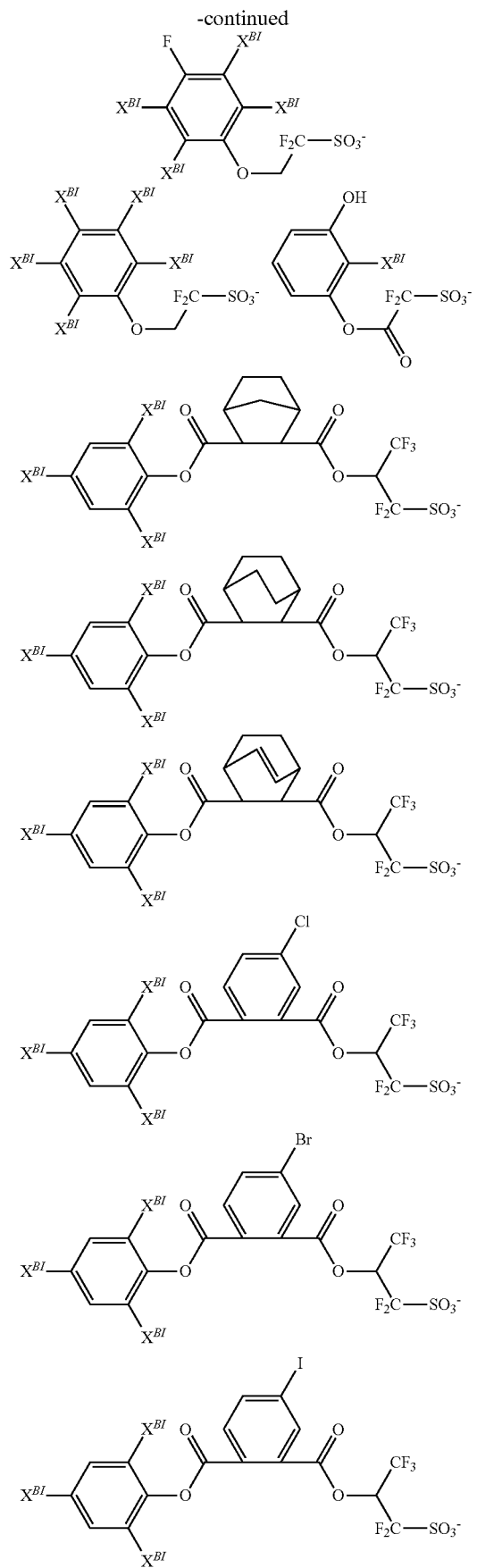
-continued
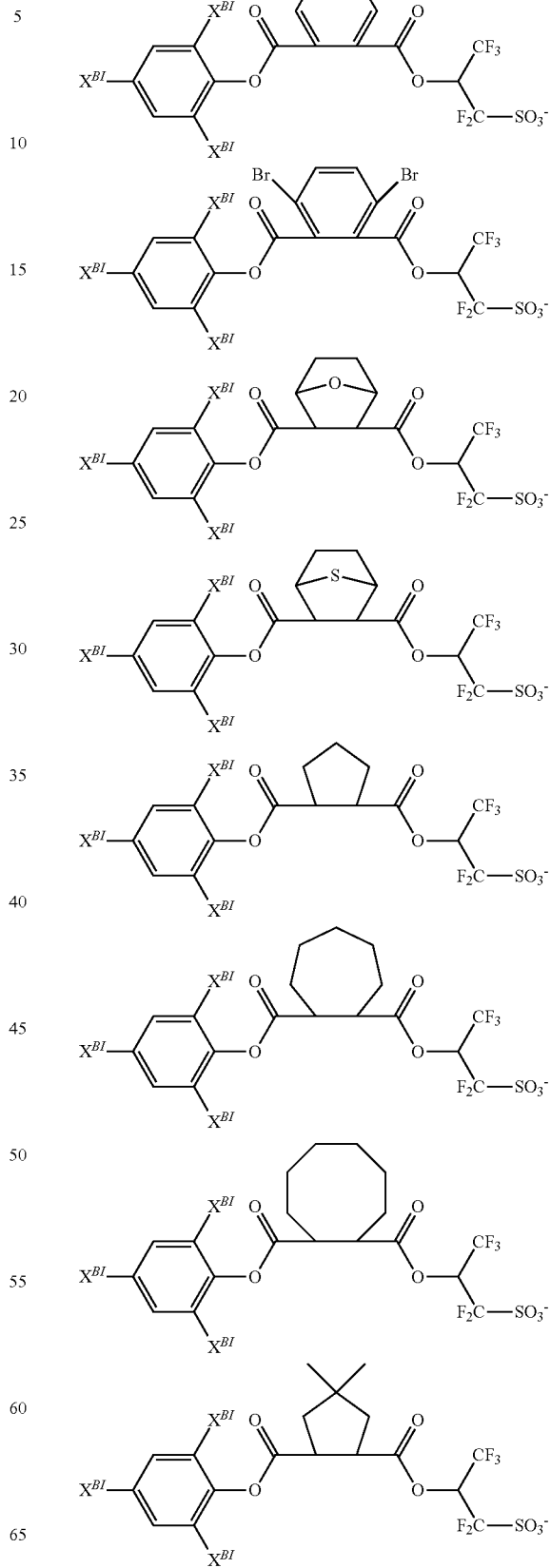

-continued
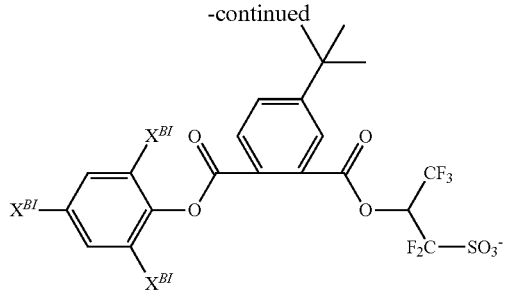
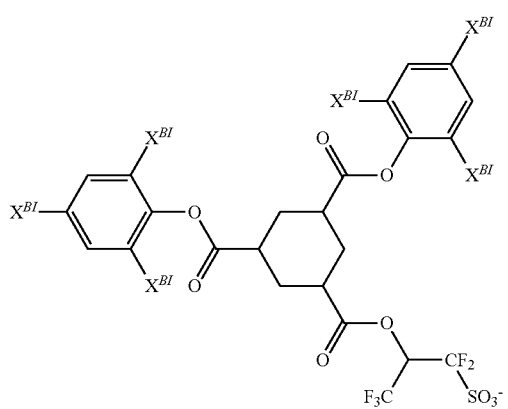
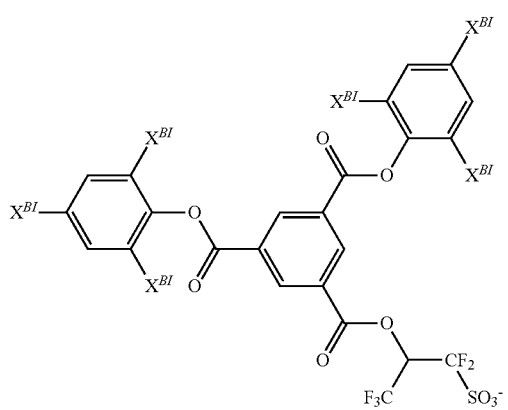
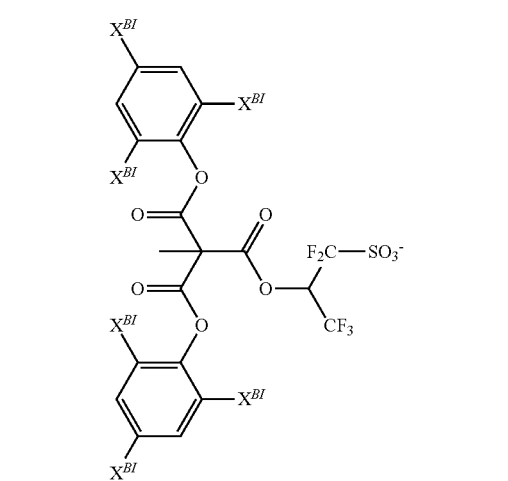
-continued
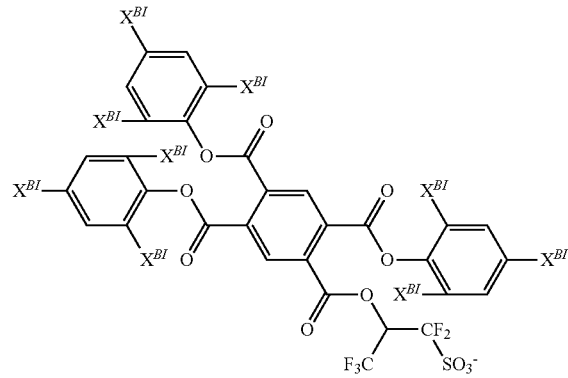
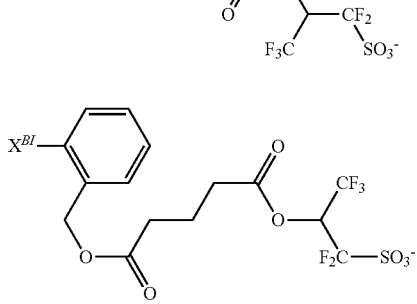
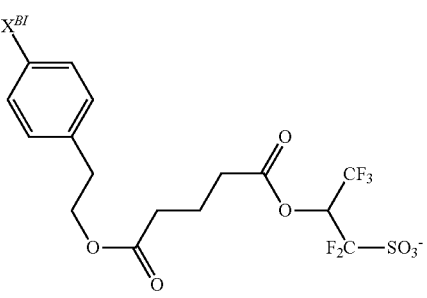
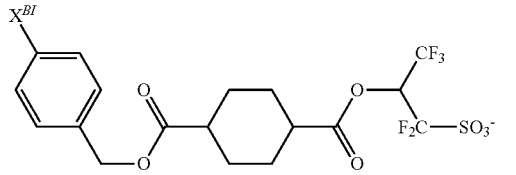
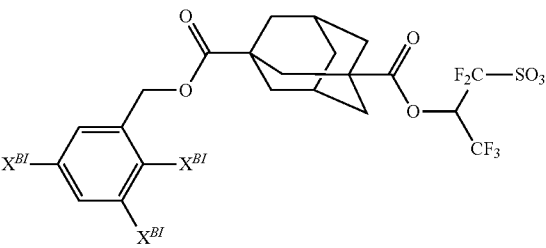
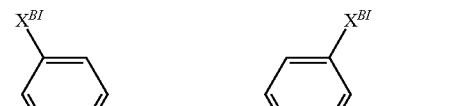
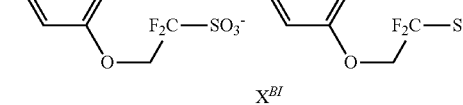
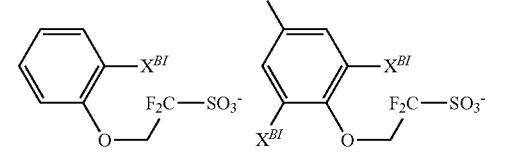

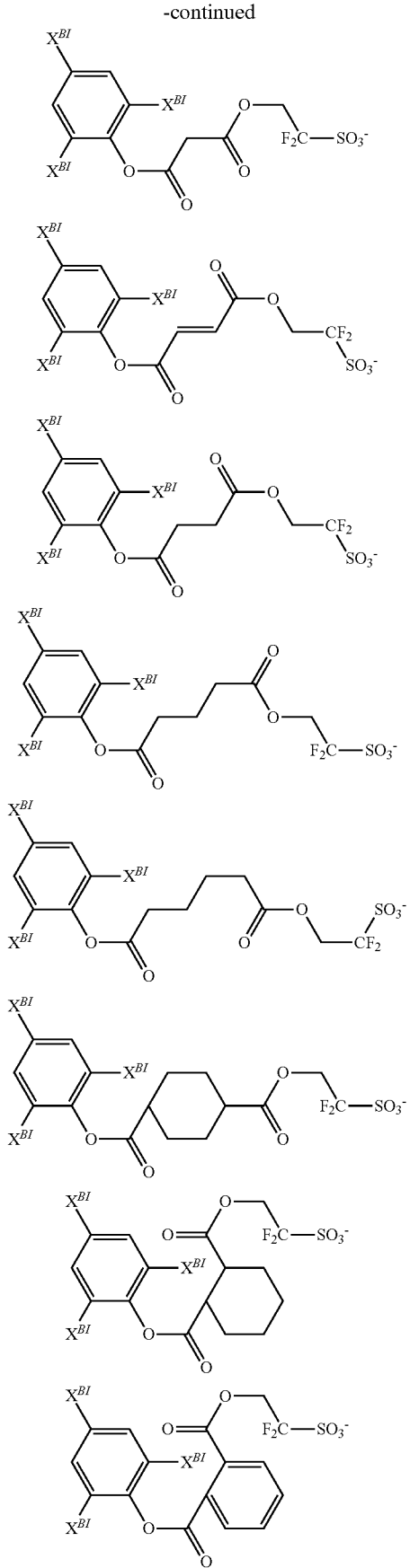
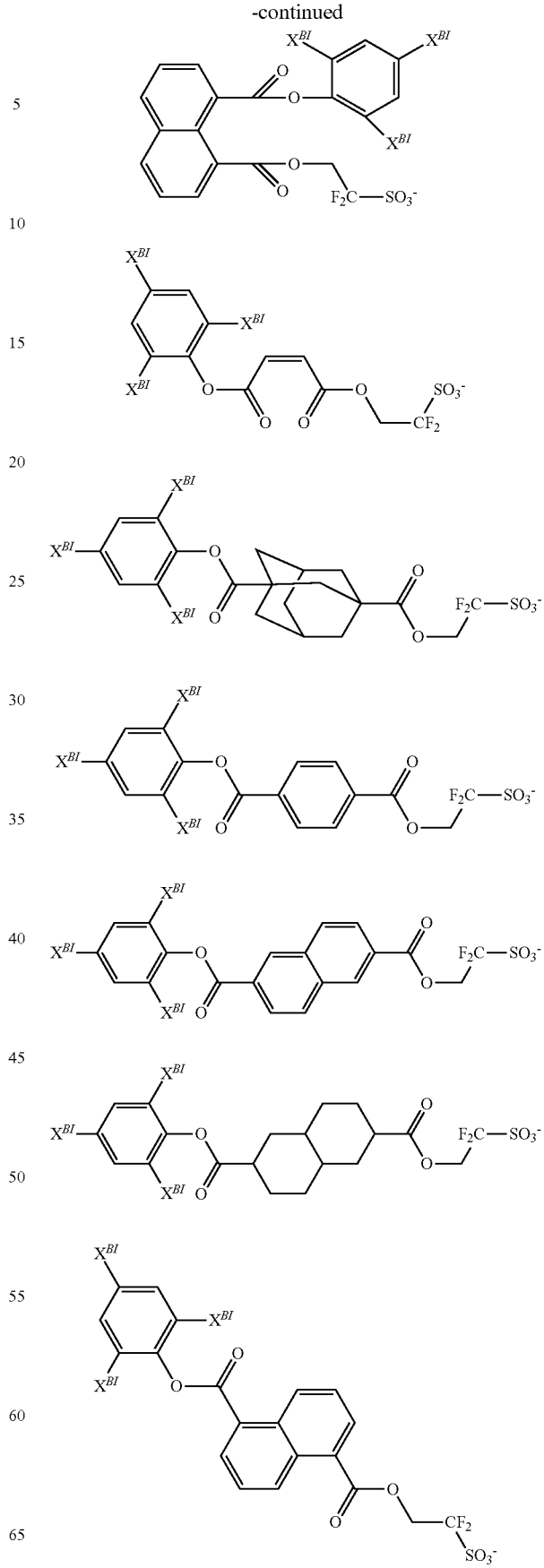

157
-continued
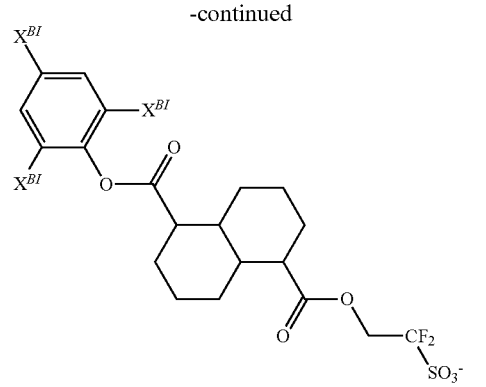
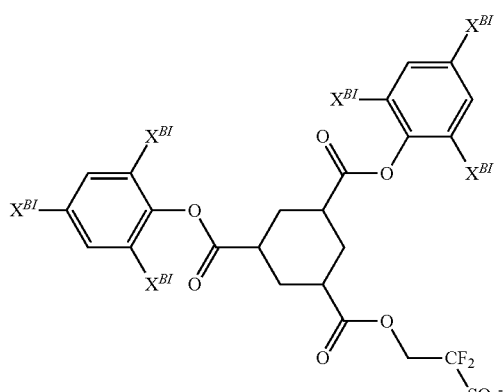
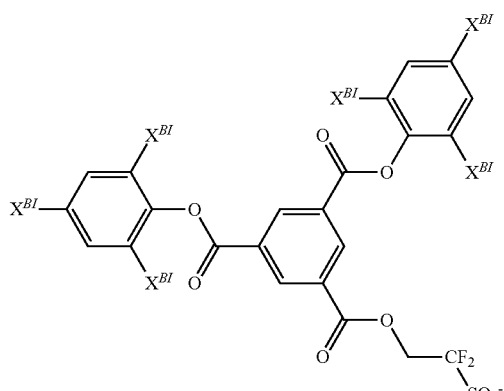
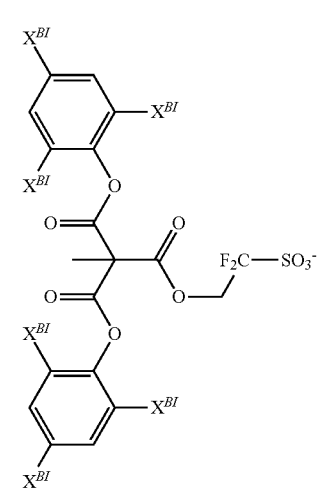
158
-continued
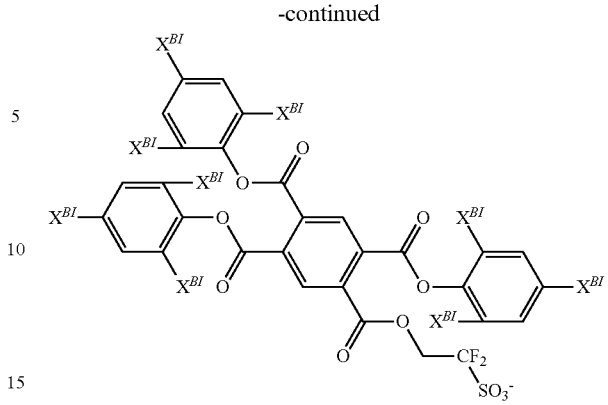
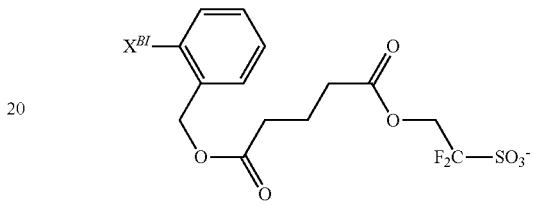
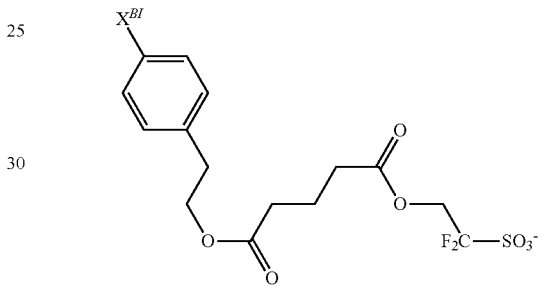
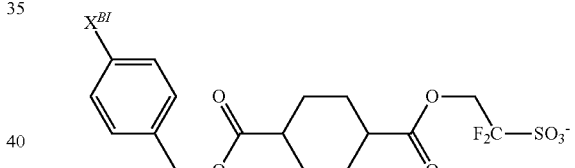
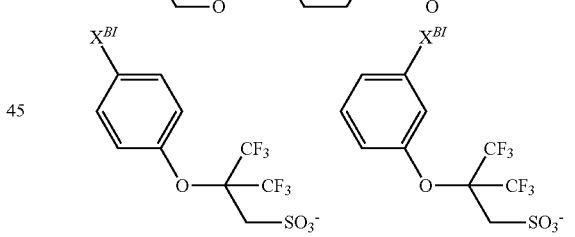
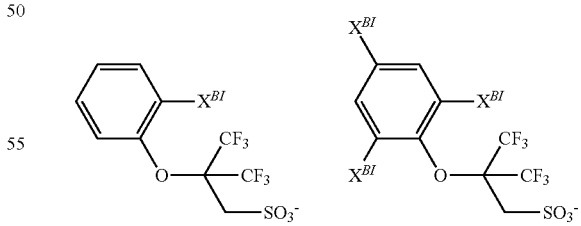
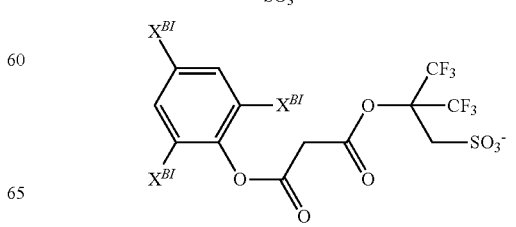

159
-continued
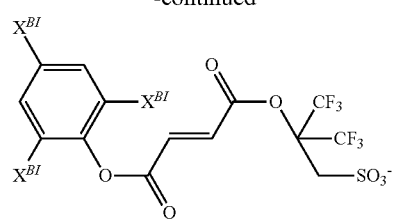
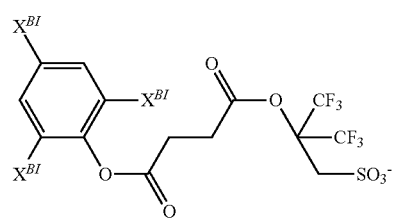
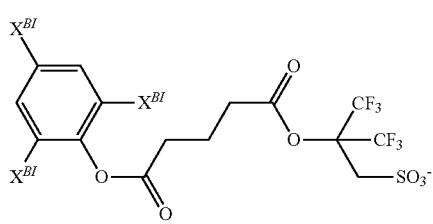
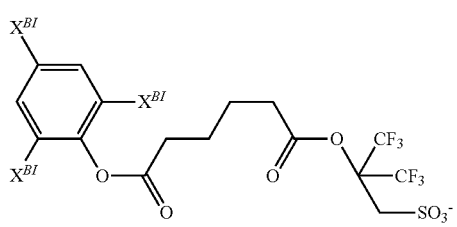
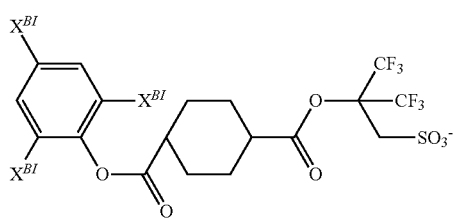
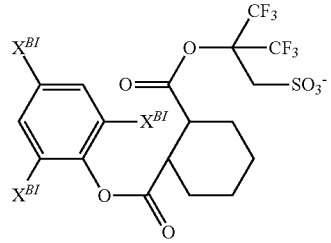
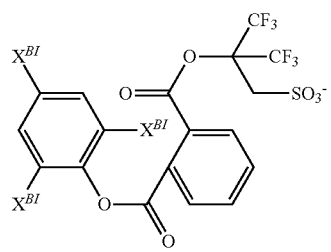
160
-continued
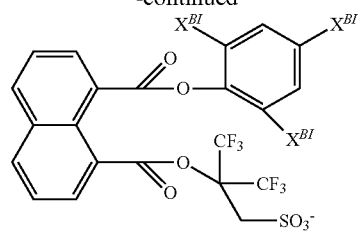
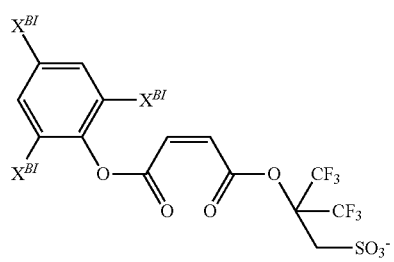
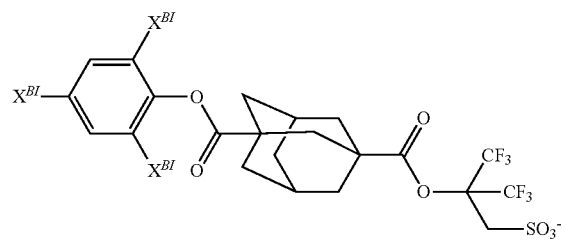
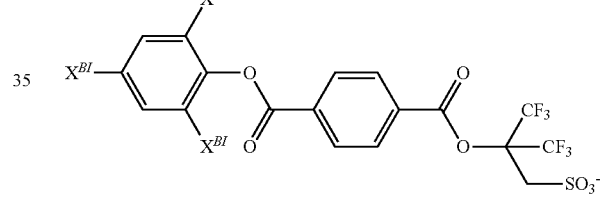
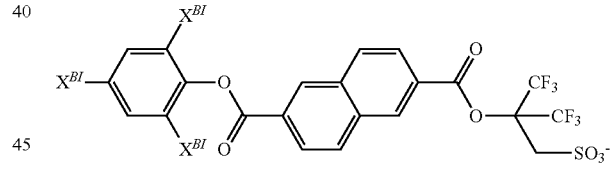
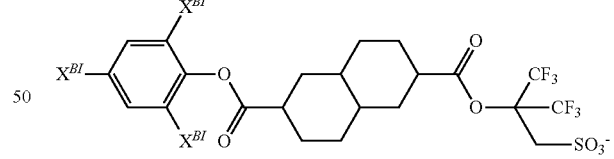
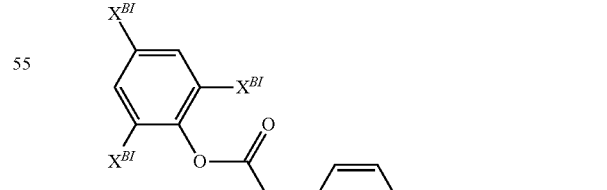
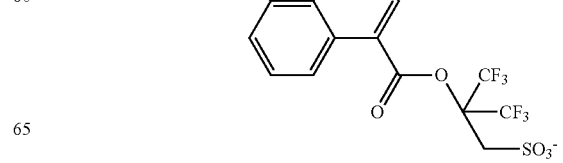

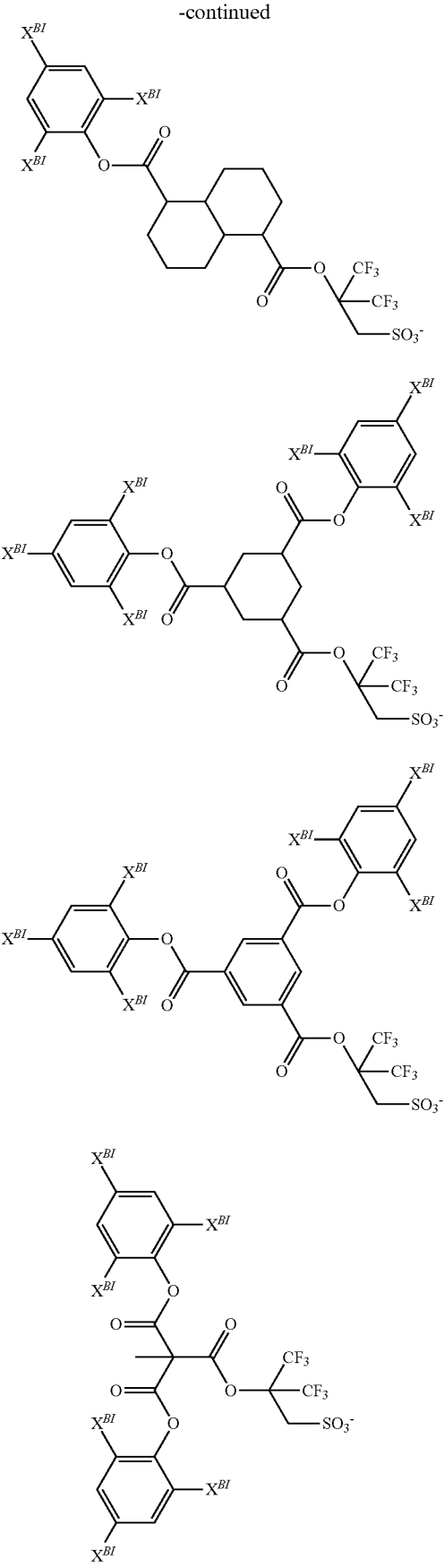
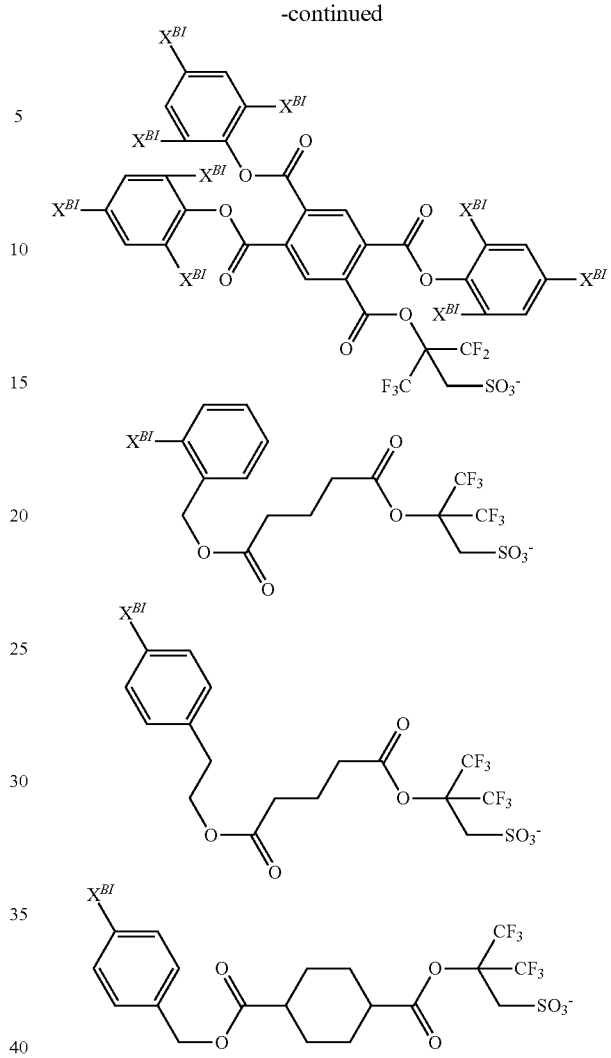

When used, the acid generator of addition type is preferably added in an amount of 0.1 to 50 parts, and more preferably 1 to 40 parts by weight per 100 parts by weight of the base polymer. The resist composition functions as a chemically amplified resist composition when the base polymer includes recurring units (f) and/or the acid generator of addition type is contained.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-inethoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a quencher, surfactant, dissolution inhibitor, and crosslinker may be blended in any desired combination to formulate a positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Amine compounds having an iodized aromatic group as described in JP-A 2020-027297 are also useful quenchers. These compounds exert a sensitizing effect due to remarkable absorption of EUV and an acid diffusion controlling effect due to a high molecular weight.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Examples of the quencher include a compound (onium salt of α-non-fluorinated sulfonic acid) having the formula (4) and a compound (onium salt of carboxylic acid) having the formula (5).

In formula (4), $R^{501}$ is hydrogen or a $C_1$-$C_{40}$ hydrocarbyl group which may contain a heteroatom, exclusive of the hydrocarbyl group in which the hydrogen bonded to the carbon atom at α-position of the sulfone group is substituted by fluorine or fluoroalkyl moiety.

The hydrocarbyl group may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; alkenyl groups such as vinyl, allyl, propenyl, butenyl and hexenyl; cyclic unsaturated aliphatic hydrocarbyl groups such as cyclohexenyl; aryl groups such as phenyl, naphthyl, alkylphenyl groups (e.g., 2-methylphenyl, 3-methylphenyl, 4-methylphenyl, 4-ethylphenyl, 4-tert-butylphenyl, 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); heteroaryl groups such as thienyl; and aralkyl groups such as benzyl, 1-phenylethyl and 2-phenylethyl.

In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride, or haloalkyl moiety. Suitable heteroatom-containing hydrocarbyl groups include alkoxyphenyl groups such as 4-hydroxyphenyl, 4-methoxyphenyl, 3-methoxyphenyl, 2-methoxyphenyl, 4-ethoxyphenyl, 4-tert-butoxyphenyl, 3-tert-butoxyphenyl; alkoxynaphthyl groups such as methoxynaphthyl, ethoxynaphthyl, n-propoxynaphthyl and n-butoxynaphthyl; dialkoxynaphthyl groups such as dimethoxynaphthyl and diethoxynaphthyl; and aryloxoalkyl groups, typically 2-aryl-2-oxoethyl groups such as 2-phenyl-2-oxoethyl, 2-(l-naphthyl)-2-oxoethyl and 2-(2-naphthyl)-2-oxoethyl.

In formula (5), $R^{502}$ is a $C_1$-$C_{40}$ hydrocarbyl group which may contain a heteroatom. Examples of the hydrocarbyl group $R^{502}$ are as exemplified above for the hydrocarbyl group $R^{501}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

In formulae (4) and (5), $Mq^+$ is an onium cation. The onium cation is preferably selected from sulfonium, iodonium and ammonium cations, more preferably sulfonium and iodonium cations. Exemplary sulfonium cations are as exemplified above for the cation in the sulfonium salt having formula (1-1). Exemplary iodonium cations are as exemplified above for the cation in the iodonium salt having formula (1-2).

A sulfonium salt of iodized benzene ring-containing carboxylic acid having the formula (6) is also useful as the quencher.

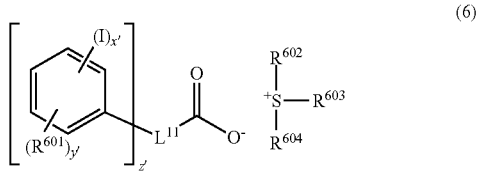

(6)

In formula (6), $R^{601}$ is hydroxyl, fluorine, chlorine, bromine, amino, nitro, cyano, or a $C_1$-$C_6$ saturated hydrocarbyl, $C_1$-$C_6$ saturated hydrocarbyloxy, $C_2$-$C_6$ saturated hydrocarbylcarbonyloxy or $C_1$-$C_4$ saturated hydrocarbylsulfonyloxy group, in which some or all hydrogen may be substituted by halogen, or —N($R^{601A}$)—C(=O)—$R^{601B}$, or —N($R^{601A}$)—C(=O)—O—$R^{601B}$. $R^{601A}$ is hydrogen or a $C_1$-$C_6$ saturated hydrocarbyl group. $R^{601B}$ is a $C_1$-$C_6$ saturated hydrocarbyl or $C_2$-$C_8$ unsaturated aliphatic hydrocarbyl group.

In formula (6), x' is an integer of 1 to 5, y' is an integer of 0 to 3, and z' is an integer of 1 to 3. $L^{11}$ is a single bond, or a $C_1$-$C_{20}$ (z'+1)-valent linking group which may contain at least one moiety selected from ether bond, carbonyl moiety, ester bond, amide bond, sultone ling, lactam ring, carbonate moiety, halogen, hydroxyl moiety, and carboxyl moiety. The saturated hydrocarbyl, saturated hydrocarbyloxy, saturated hydrocarbylcarbonyloxy, and saturated hydrocarbylsulfonyloxy groups may be straight, branched or cyclic. Groups $R^{601}$ may be the same or different when y' and/or z' is 2 or 3.

In formula (6), $R^{602}$, $R^{603}$ and $R^{604}$ are each independently halogen, or a $C_1$-$C_{20}$ hydrocarbyl group which may contain a heteroatom. The hydrocarbyl group may be saturated or unsaturated and straight, branched or cyclic. Examples thereof include $C_1$-$C_{20}$ alkyl, $C_2$-$C_{20}$ alkenyl, $C_6$-$C_{20}$ aryl, and $C_7$-$C_{20}$ aralkyl groups. In these groups, some or all hydrogen may be substituted by hydroxyl, carboxyl, halogen, oxo, cyano, nitro, sultone, sulfone, or sulfonium salt-containing moiety, or some carbon may be replaced by an ether bond, ester bond, carbonyl moiety, amide bond, carbonate moiety or sulfonic acid ester bond. Also $R^{602}$ and $R^{603}$ may bond together to form a ring with the sulfur atom to which they are attached.

Examples of the compound having formula (6) include those described in U.S. Pat. No. 10,295,904 (JP-A 2017-219836). These compounds exert a sensitizing effect due to remarkable absorption and an acid diffusion controlling effect.

Also useful are quenchers of polymer type as described in U.S. Pat. No. 7,598,016 (JP-A 2008-239918). The polymeric quencher segregates at the resist surface and thus enhances the rectangularity of resist pattern. When a protective film is applied as is often the case in the immersion lithography, the polymeric quencher is also effective for preventing a film thickness loss of resist pattern or rounding of pattern top.

When used, the quencher is preferably added in an amount of 0 to 5 parts, more preferably 0 to 4 parts by weight per 100 parts by weight of the base polymer. The quencher may be used alone or in admixture.

Exemplary surfactants are described in JP-A 2008-111103, paragraphs [0165]-[0166], Inclusion of a surfactant may improve or control the coating characteristics of the resist composition. When used, the surfactant is preferably added in an amount of 0.0001 to parts by weight per 100 parts by weight of the base polymer. The surfactant may be used alone or in admixture.

When the resist composition is of positive tone, the inclusion of a dissolution inhibitor may lead to an increased difference in dissolution rate between exposed and unexposed areas and a further improvement in resolution. The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

When the resist composition is of positive tone and contains a dissolution inhibitor, the dissolution inhibitor is preferably added in an amount of 0 to 50 parts, more preferably to 40 parts by weight per 100 parts by weight of the base polymer. The dissolution inhibitor may be used alone or in admixture.

When the resist composition is of negative tone, a negative pattern may be formed by adding a crosslinker to reduce the dissolution rate of a resist film in exposed area. Suitable crosslinkers include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy group. These compounds may be used as an additive or introduced into a polymer side chain as a pendant. Hydroxy-containing compounds may also be used as the crosslinker.

Examples of the epoxy compound include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaeiythritol trivinyl ether, pentaerythritol tetravinyl ether, sorbitol tetravinyl ether, sorbitol pentavinyl ether, and trimethylol propane trivinyl ether.

When the resist composition is of negative tone and contains a crosslinker, the crosslinker is preferably added in an amount of 0.1 to 50 parts, more preferably 1 to 40 parts by weight per 100 parts by weight of the base polymer. The crosslinker may be used alone or in admixture.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer. The acetylene alcohols may be used alone or in admixture.

Pattern Forming Process

The resist composition is used in the fabrication of various integrated circuits. Pattern formation using the resist composition may be performed by well-known lithography processes. The process generally involves the steps of applying the resist composition onto a substrate to form a resist film thereon, exposing the resist film to high-energy radiation, and developing the exposed resist film in a developer. If necessary, any additional steps may be added.

The resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV of wavelength 3-15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 $mJ/cm^2$, more preferably about 10 to 100 $mJ/cm^2$. When EB is used as the high-energy radiation, the resist film is exposed thereto directly or through a mask having a desired pattern in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hotplate or in an oven at 60 to 150° C. for 10 seconds to 30 minutes, preferably at 80 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). In the case of positive resist, the resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or bench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

[1] Synthesis of Monomers

Example 1-1

Synthesis of Monomer M-1

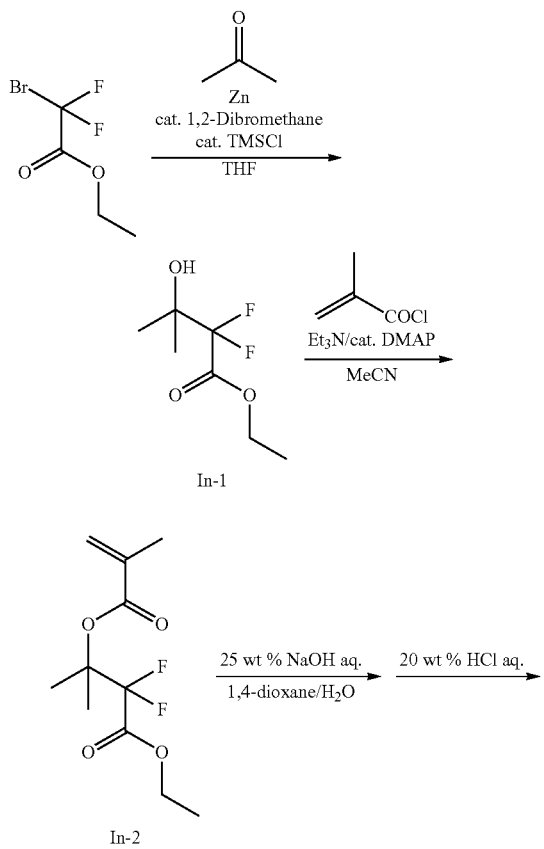

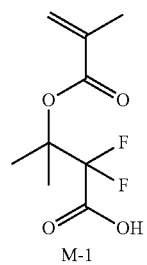

(1) Synthesis of Intermediate In-1

In a reactor under nitrogen atmosphere, 82.4 g of metallic zinc was suspended in 400 mL of tetrahydrofuran (THF). The reactor was heated until the temperature within the reactor (referred to as internal temperature, hereinafter) reached 50° C. Then, 4.7 g of 1,2-dibromoethane was added to the suspension, which was heated under reflux for 1 hour. The reactor was cooled until the internal temperature reached 40° C. 1.6 g of chlorotrimethylsilane was added to the solution, which was stirred for 30 minutes at the internal temperature of 40° C. and diluted with 100 mL of THF. Thereafter, a solution of 243.9 g of ethyl bromodifluoroacetate in 83.6 g of acetone and 100 mL of THF was added drop wise at an internal temperature in the range of 40 to 55° C. At the end of dropwise addition, the reaction solution was aged at an internal temperature of 55° C. for 30 minutes. After the reaction solution was cooled, 367.5 g of 20 wt % hydrochloric acid was added dropwise to quench the reaction. This was followed by extraction with 1,000 mL of diisopropyl ether, standard aqueous work-up, and solvent distillation. The product was purified by distillation (boiling point 77° C./1,500 Pa), obtaining Intermediate In-1 as colorless transparent oily matter (amount 163.3 g, yield 72%).

(2) Synthesis of Intermediate In-2

In nitrogen atmosphere, a reactor was charged with a solution of 155.0 g of In-1, 149.4 g of triethylamine, 10.0 g of dimethylaminopyridine, and 450 g of acetonitrile, to which 128.6 g of methacrylic chloride was added dropwise at an internal temperature below 20° C. The solution was aged at an internal temperature of 50° C. for 12 hours, after which it was ice cooled. 200 mL of saturated sodium hydrogencarbonate water was added dropwise to quench the reaction. This was followed by extraction with 200 mL of hexane and 100 mL of toluene, standard aqueous work-up, and solvent distillation. The product was purified by distillation (boiling point 62° C./100 Pa), obtaining Intermediate In-2 as colorless transparent oily matter (amount 202.2 g, yield 89%).

(3) Synthesis of Monomer M-1

In a reactor under nitrogen atmosphere, 200.3 g of In-2 was dissolved in 600 g of 1,4-dioxane. At room temperature, 133.4 g of 25 wt % sodium hydroxide aqueous solution was added dropwise to the solution. The solution was aged at room temperature for 3 hours, combined with 300 mL of toluene and 300 mL of water, and allowed for separation. The water layer was taken out and washed twice with 150 mL of toluene. After washing, 158.9 g of 20 wt % hydrochloric acid was added dropwise to the water layer. This was followed by extraction with 600 mL of ethyl acetate, standard aqueous work-up, and solvent distillation. The product was recrystallized from hexane, obtaining Monomer M-1 as white crystals (amount 143.2 g, yield 85%).

Monomer M-1 was analyzed by IR and NMR spectroscopy, with the results shown below.

IR (D-ATR): ν=3356, 3190, 3006, 2955, 2655, 2537, 1765, 1699, 1636, 1464, 1412, 1392, 1381, 1375, 1348, 1317, 1275, 1253, 1218, 1202, 1167, 1136, 1065, 1021, 953, 884, 815, 756, 710, 667, 652, 580, 522 cm$^{-1}$ $^1$H-NMR (600 MHz in DMSO-d6):
δ=5.99 (1H, s), 5.68 (1H, s), 1.80 (3H, s), 1.63 (6H, d) ppm Example 1-2

Synthesis of Monomer M-2

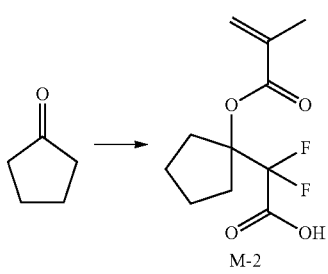

By following the same procedure as in Example 1-1 aside from using cyclopentanone instead of acetone, Monomer M-2 was obtained as white crystals (three-step yield 42%).

[2] Synthesis of Fluorocarboxylic Acid-Containing Polymers

Monomers M-3 to M-10 and cM-1 and cM-2 used in the synthesis of fluorocarboxylic acid-containing polymers have the structure shown below.

M-3

M-4

M-5

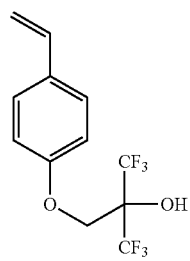

M-6

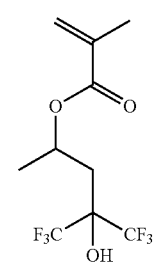

M-7

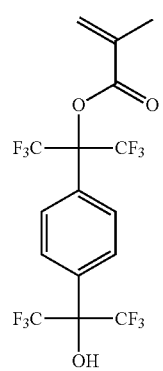

M-8

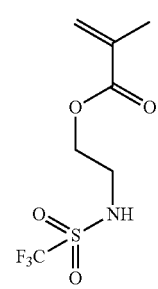

M-9

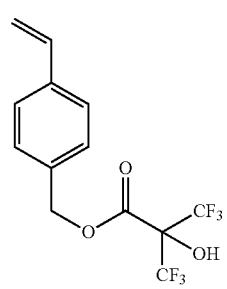

M-10 cM-1

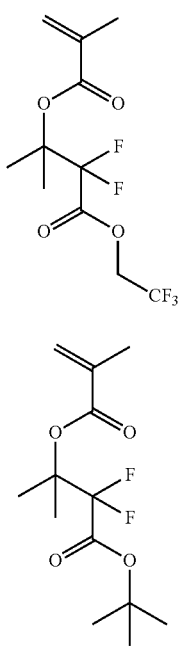

cM-2

Example 2-1

Synthesis of Polymer FP-1

A 2-L flask was charged with 4.4 g of Monomer M-1, 10.0 g of 3,3,4,4,5,5,6,6,6-nonafluorohexyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of azobisisobutyronitrile (AIBN) as polymerization initiator was added. The reactor was heated at 60° C. and held at the temperature for 15 hours for reaction. The reaction solution was poured into 1 L of isopropyl alcohol (IPA) for precipitation. The resulting white solid was collected by filtration and dried in vacuum at 60° C., obtaining Polymer FP-1. The polymer was analyzed for composition by $^{13}$C- and $^1$H-NMR spectroscopy and for Mw and Mw/Mn by GPC.

FP-1

Mw = 10,300
Mw/Mn = 1.60

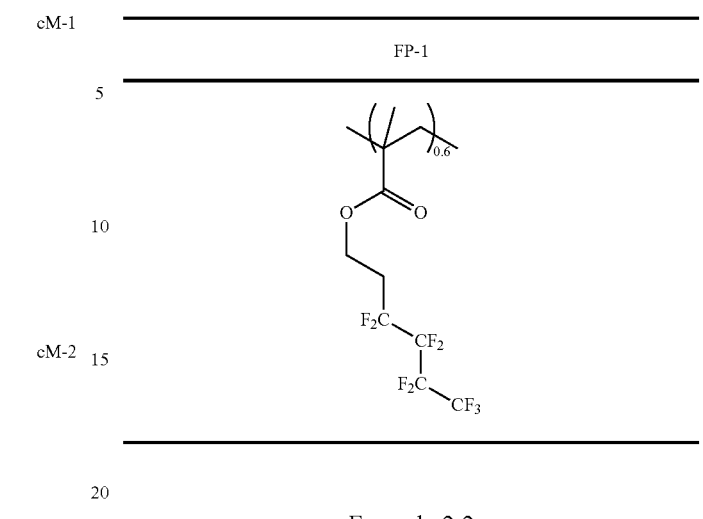

Example 2-2

Synthesis of Polymer FP-2

A 2-L flask was charged with 5.0 g of Monomer M-2, 9.0 g of 1H, 1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for hours for reaction. The reaction solution was poured into 1 L of IPA for precipitation. The resulting white solid was collected by filtration and dried in vacuum at 60° C., obtaining Polymer FP-2. The polymer was analyzed for composition by $^{13}$C- and $^1$H-NMR spectroscopy and for Mw and Mw/Mn by GPC.

FP-2

Mw = 10,100
Mw/Mn = 1.70

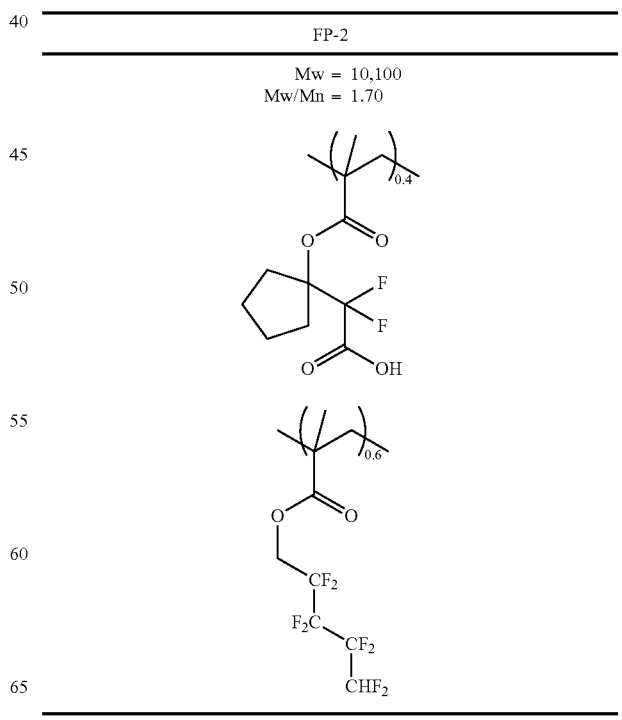

Example 2-3

Synthesis of Polymer FP-3

A 2-L flask was charged with 4.4 g of Monomer M-1, 5.9 g of Monomer M-3, 3.0 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for hours for reaction. The reaction solution was poured into 1 L of IPA for precipitation. The resulting white solid was collected by filtration and dried in vacuum at 60° C., obtaining Polymer FP-3. The polymer was analyzed for composition by $^{13}$C- and $^{1}$H-NMR spectroscopy and for Mw and Mw/Mn by GPC.

FP-3
Mw = 9,800
Mw/Mn = 1.73

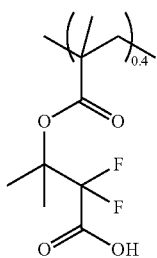

-continued

FP-3

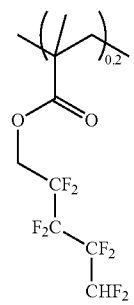

Example 2-4

Synthesis of Polymer FP-4

A 2-L flask was charged with 3.3 g of Monomer M-1, 10.0 g of Monomer M-4, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-4. The polymer was analyzed for composition by $^{13}$C- and $^{1}$H-NMR spectroscopy and for Mw and Mw/Mn by GPC.

FP-4
Mw = 9,100
Mw/Mn = 1.88

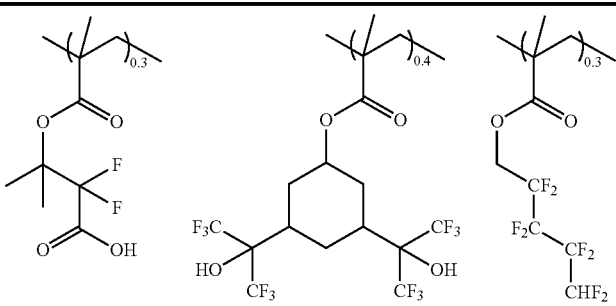

-continued

FP-3

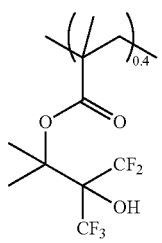

Example 2-5

Synthesis of Polymer FP-5

A 2-L flask was charged with 3.3 g of Monomer M-1, 8.7 g of Monomer M-5, 3.5 g of 1,1,1,3,3,3-hexafluoroisopropyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for hours for reaction. The reaction solution was poured into 1 L of IPA for precipitation. The resulting white solid was collected by filtration and dried in vacuum at 60° C., obtaining Polymer FP-5. The polymer was analyzed for composition by $^{13}$C- and $^{1}$H-NMR spectroscopy and for Mw and Mw/Mn by GPC.

FP-5
Mw = 9,800
Mw/Mn = 1.89

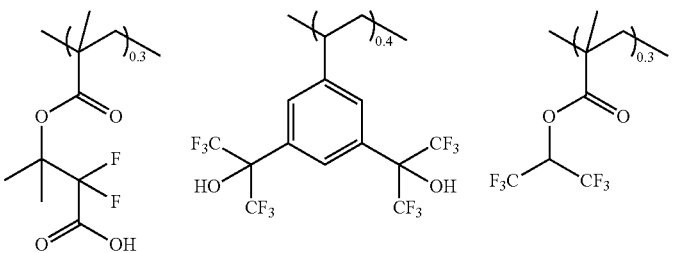

Example 2-6

Synthesis of Polymer FP-6

A 2-L flask was charged with 3.3 g of Monomer M-1, 6.0 g of Monomer M-6, 3.5 g of 1,1,1,3,3,3-hexafluoroisopropyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-6. The polymer was analyzed for composition by $^{13}$C- and 1H-NMR spectroscopy and for Mw and Mw/Mn by GPC.

FP-6
Mw = 9,200
Mw/Mn = 1.73

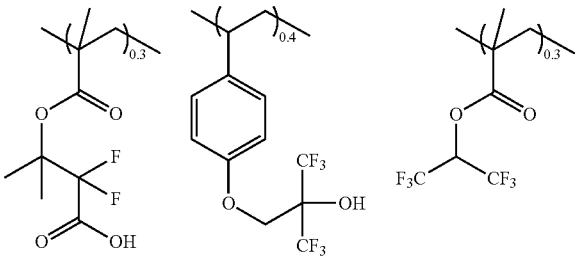

Example 2-7

Synthesis of Polymer FP-7

A 2-L flask was charged with 3.3 g of Monomer M-1, 10.3 g of Monomer M-7, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of EPA for precipitation. The resulting white solid was collected by filtration and dried in vacuum at 60° C., obtaining Polymer FP-7. The polymer was analyzed for composition by $^{13}$C- and $^1$H-NMR spectroscopy and for Mw and Mw/Mn by GPC.

FP-7
Mw = 8,800
Mw/Mn = 1.69

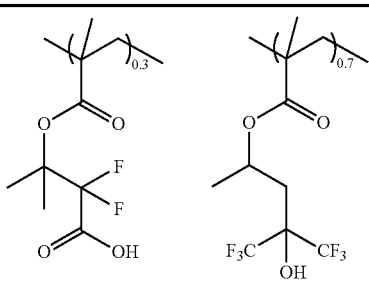

Example 2-8

Synthesis of Polymer FP-8

A 2-L flask was charged with 3.3 g of Monomer M-1, 16.7 g of Monomer M-8, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-8. The polymer was analyzed for composition by $^{13}$C- and $^1$H-NMR spectroscopy and for Mw and Mw/Mn by GPC.

FP-8
Mw = 8,600
Mw/Mn = 1.73

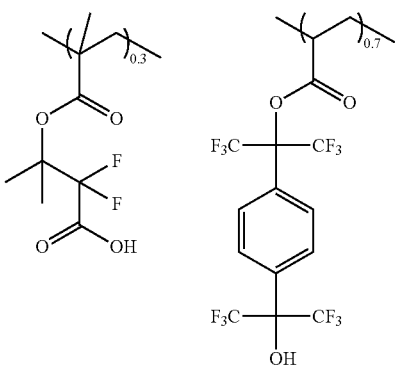

Example 2-9

Synthesis of Polymer FP-9

A 2-L flask was charged with 4.4 g of Monomer M-1, 3.9 g of Monomer M-9, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for hours for reaction. The reaction solution was poured into 1 L of IPA for precipitation. The resulting white solid was collected by filtration and dried in vacuum at 60° C., obtaining Polymer FP-9. The polymer was analyzed for composition by $^{13}$C- and $^1$H-NMR spectroscopy and for Mw and Mw/Mn by GPC.

FP-9
Mw = 10,800
Mw/Mn = 1.93

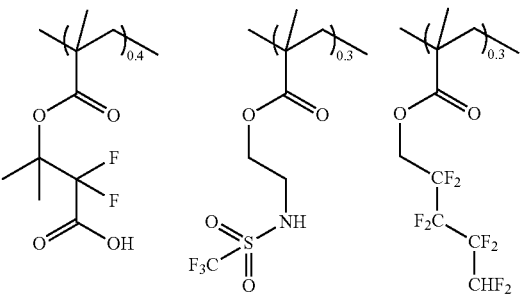

Example 2-10

Synthesis of Polymer FP-10

A 2-L flask was charged with 4.4 g of Monomer M-1, 4.9 g of Monomer M-10, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-10. The polymer was analyzed for composition by $^{13}$C- and $^1$H-NMR spectroscopy and for Mw and Mw/Mn by GPC.

FP-10
Mw = 10,100
Mw/Mn = 1.96

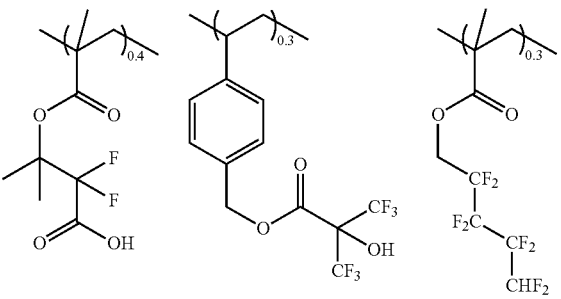

Example 2-11

Synthesis of Polymer FP-11

A 2-L flask was charged with 6.7 g of Monomer M-1, 8.6 g of 1H,1H,2H,2H-tridecafluoro-n-octyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-11. The polymer was analyzed for composition by $^{13}$C- and $^1$H-NMR spectroscopy and for Mw and Mw/Mn by GPC.

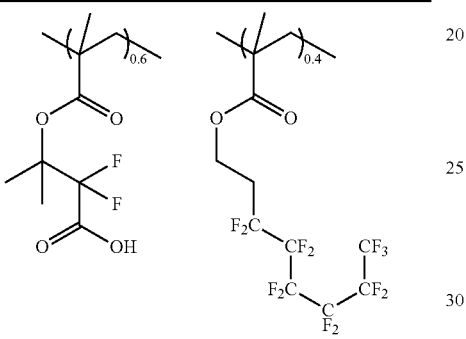

FP-11
Mw = 10,900
Mw/Mn = 1.83

Example 2-12

Synthesis of Polymer FP-12

A 2-L flask was charged with 4.4 g of Monomer M-1, 5.8 g of pentafluorostyrene, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of ATRN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-12. The polymer was analyzed for composition by $^{13}$C- and $^1$H-NMR spectroscopy and for Mw and Mw/Mn by GPC.

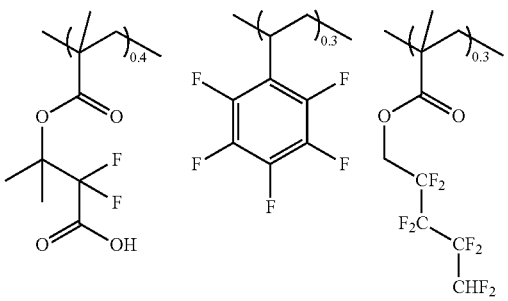

FP-12
Mw = 9,300
Mw/Mn = 1.86

Example 2-13

Synthesis of Polymer FP-13

A 2-L flask was charged with 4.4 g of Monomer M-1, 7.6 g of pentafluorophenyl methacrylate, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Polymer FP-13. The polymer was analyzed for composition by $^{13}$C- and $^{1}$H-NMR spectroscopy and for Mw and Mw/Mn by GPC.

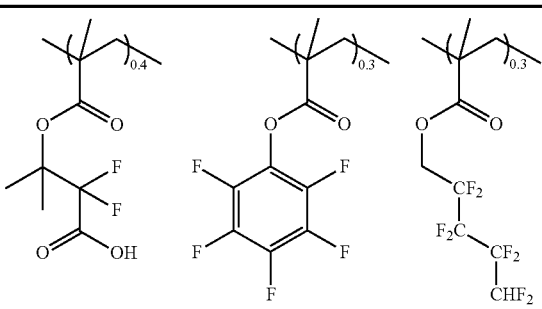

FP-13
Mw = 9,800
Mw/Mn = 1.81

Comparative Example 1-1

Synthesis of Comparative Polymer cFP-1

A 2-L flask was charged with 17.5 g of Monomer M-4, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for hours for reaction. The reaction solution was poured into 1 L of IPA for precipitation. The resulting white solid was collected by filtration and dried in vacuum at 60° C., obtaining Comparative Polymer cFP-1. The polymer was analyzed for composition by $^{13}$C- and $^{1}$H-NMR spectroscopy and for Mw and Mw/Mn by GPC.

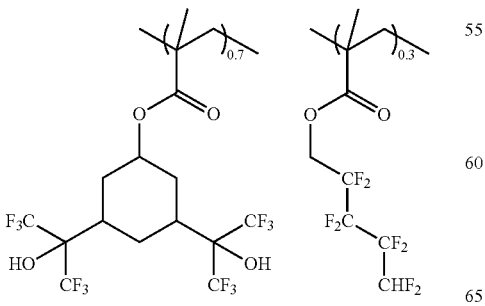

cFP-1
Mw = 9,300
Mw/Mn = 1.85

Comparative Example 1-2

Synthesis of Comparative Polymer cFP-2

A 2-L flask was charged with 1.3 g of methacrylic acid, 10.0 g of Monomer M-4, 4.5 g of 1H,1H,5H-octafluoropentyl methacrylate, and 40 g of THF solvent. The reactor was cooled at −70° C. in a nitrogen atmosphere, after which vacuum pumping and nitrogen blow were repeated three times. The reactor was warmed up to room temperature, whereupon 1.2 g of AIBN was added. The reactor was heated at 60° C. and held at the temperature for 15 hours for reaction. The reaction solution was poured into 1 L of IPA for precipitation. The resulting white solid was collected by filtration and dried in vacuum at 60° C., obtaining Comparative Polymer cFP-2. The polymer was analyzed for composition by $^{13}$C- and $^1$H-NMR spectroscopy and for Mw and Mw/Mn by GPC.

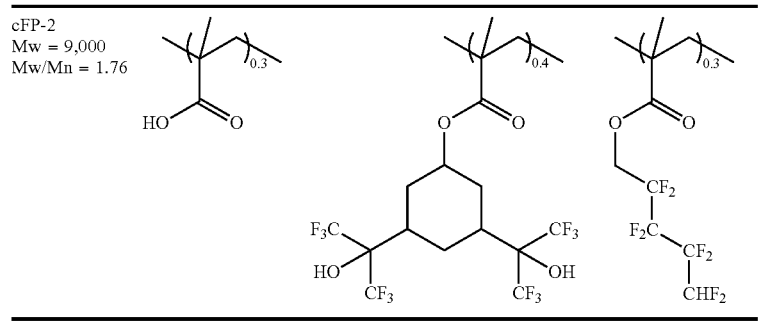

cFP-2
Mw = 9,000
Mw/Mn = 1.76

Comparative Example 1-3

Synthesis of Comparative Polymer cFP-3

Comparative Polymer cFP-3 was synthesized by the same procedure as in Comparative Example 1-2 aside from using Monomer cM-1 instead of methacrylic acid. The polymer was analyzed for composition by $^{13}$C- and $^1$H-NMR spectroscopy and for Mw and Mw/Mn by GPC.

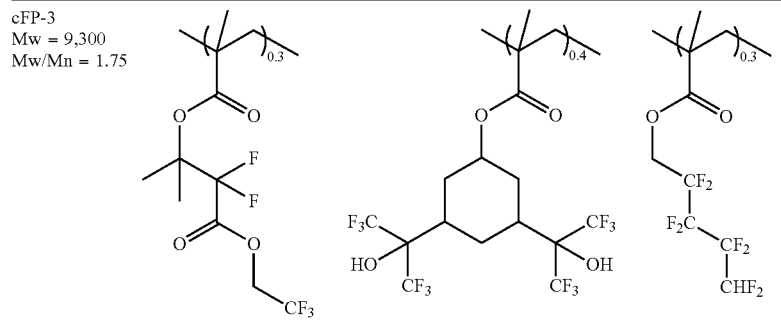

cFP-3
Mw = 9,300
Mw/Mn = 1.75

Comparative Example 1-4

Synthesis of Comparative Polymer cFP-4

Comparative Polymer cFP-4 was synthesized by the same procedure as in Comparative Example 1-2 aside from using Monomer cM-2 instead of methacrylic acid. The polymer was analyzed for composition by $^{13}$C- and $^1$H-NMR spectroscopy and for Mw and Mw/Mn by GPC.

cFP-4
Mw = 9,400
Mw/Mn = 1.77

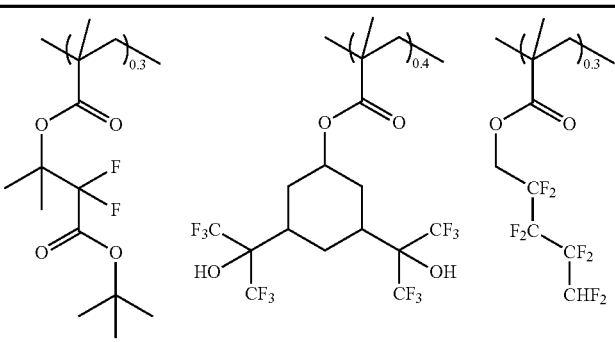

[3] Synthesis of Base Polymers

Synthesis Examples 1 and 2

Synthesis of Base Polymers BP-1 and BP-2

Base polymers BP-1 and BP-2 were prepared by combining suitable monomers, effecting copolymerization reaction thereof in THF solvent, pouring the reaction solution into methanol for precipitation, repeatedly washing with hexane, isolation, and drying. The resulting polymers were analyzed for composition by $^1$H-NMR spectroscopy, and for Mw and Mw/Mn by GPC versus polystyrene standards using THF solvent.

[4] Preparation and Evaluation of Resist Compositions

Examples 3-1 to 3-17 and Comparative Examples 2-1 to 2-6

(1) Preparation of Resist Compositions

Resist compositions were prepared by dissolving the selected components in a solvent in accordance with the recipe shown in Table 1, and filtering through a filter having a pore size of 0.2 μm. The solvent contained 100 ppm of surfactant PolyFox PF-636 (Omnova Solutions Inc.). The resist compositions of Examples 3-1 to 3-14, 3-16, 3-17 and BP-1
Mw = 8,300
Mw/Mn = 1.75

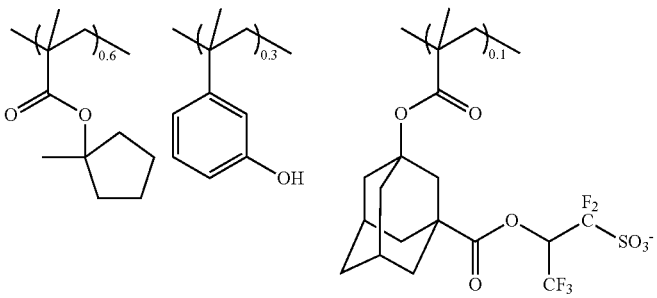

BP-2
Mw = 6,900
Mw/Mn = 1.62

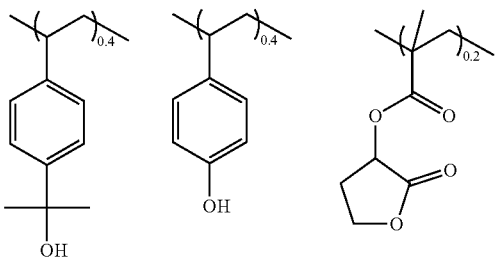

Comparative Examples 2-1 to 2-5 were of positive tone while the resist compositions of Example 3-15 and Comparative Example 2-6 were of negative tone. The components in Table 1 are as identified below.

Organic Solvents:
  PGMEA (propylene glycol monomethyl ether acetate)
  DAA (diacetone alcohol)

Acid Generators: PAG-1 to PAG-4 of the Following Structural Formulae

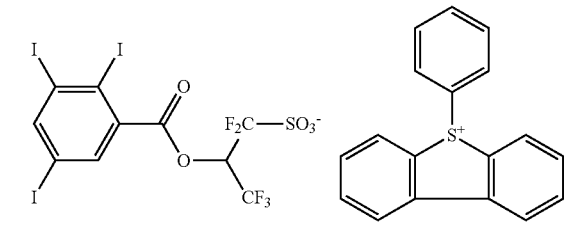

PAG-1

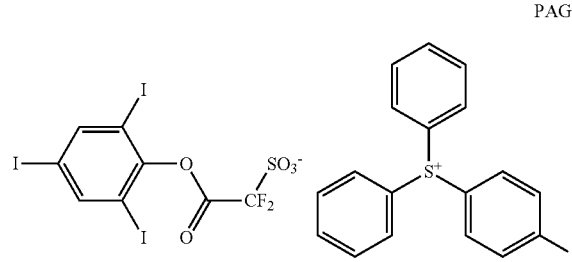

PAG-2

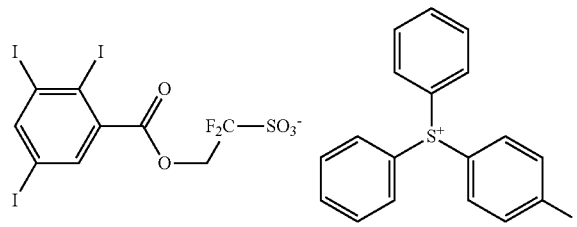

PAG-3

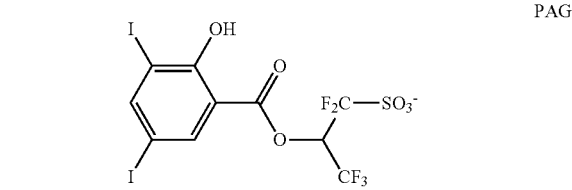

PAG-4

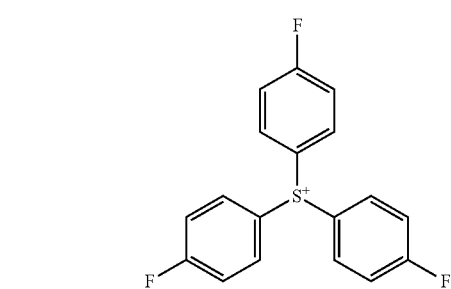

Quenchers: Q-1 to Q-4 of the Following Structural Formulae

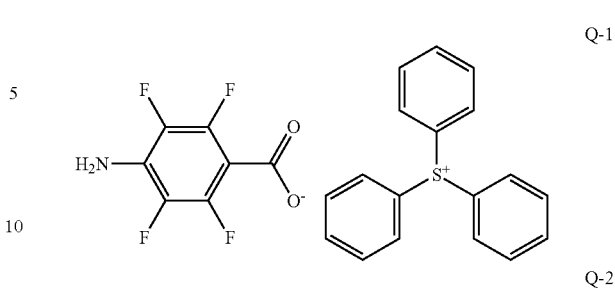

Q-1

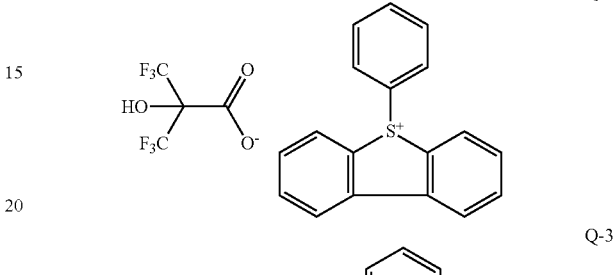

Q-2

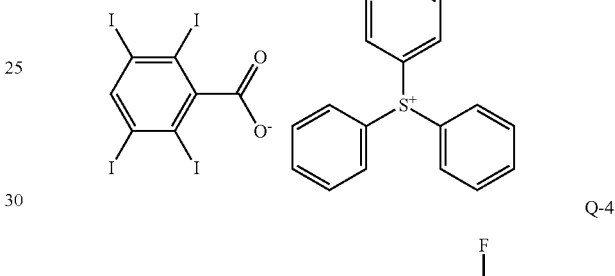

Q-3

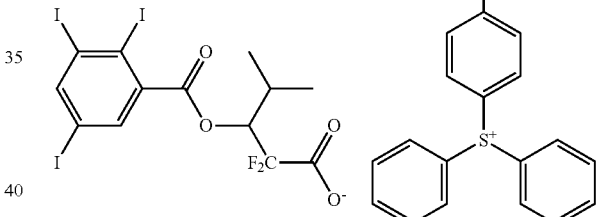

Q-4

(2) EUV Lithography Test

Each of the resist compositions in Table 1 was spin coated on a silicon substrate having a 20-nm coating of silicon-containing spin-on hard mask SHB-A940 (Shin-Etsu Chemical Co., Ltd., silicon content 43 wt %) and prebaked on a hotplate at 100° C. for 60 seconds to form a resist film of 40 nm thick. Using an EUV scanner NXE3300 (ASML, NA 0.33, σ 0.9, 90° dipole illumination), the resist film was exposed to EUV through a mask bearing a 18-nm 1:1 line-and-space (LS) pattern in the case of positive resist film or a mask bearing a 22-nm 1:1 LS pattern in the case of negative resist film. The resist film was baked (PEB) on a hotplate at the temperature shown in Table 1 for 60 seconds and developed in a 2.38 wt % TMAH aqueous solution for 30 seconds to form a LS pattern having a size of 18 nm in Examples 3-1 to 3-14, 3-16, 3-17 and Comparative Examples 2-1 to 2-5 or a LS pattern having a size of 22 nm in Example 3-15 and Comparative Example 2-6.

The resist pattern was observed under CD-SEM (CG-5000, Hitachi High-Technologies Corp.). The exposure dose that provides a LS pattern at 1:1 is reported as sensitivity. The LWR of the pattern at that dose was measured. Reported as a window is the size of the thickest line in the under-exposed region where no stringy bridges are formed between lines minus the size of the thinnest line in the over-exposed region where no lines collapse.

The resist composition is shown in Table 1 together with the sensitivity, window and LWR of EUV lithography.

TABLE 1

| | | Fluorocarboxylic acid-containing polymer (pbw) | Base polymer (pbw) | Acid generator (pbw) | Quencher (pbw) | Organic solvent (pbw) | PEB temp. (°C.) | Sensitivity (mJ/cm$^2$) | Window (nm) | LWR (nm) |
|---|---|---|---|---|---|---|---|---|---|---|
| Example | 3-1 | FP-1 (2) | BP-1 (100) | — | Q-1 (4.71) | PGMEA (3,500) DAA (500) | 85 | 33 | 10 | 2.4 |
| | 3-2 | FP-2 (4) | BP-1 (100) | — | Q-2 (4.79) | PGMEA (3,500) DAA (500) | 85 | 35 | 12 | 2.5 |
| | 3-3 | FP-3 (2.5) | BP-1 (100) | — | Q-3 (7.61) | PGMEA (3,500) DAA (500) | 85 | 32 | 14 | 2.6 |
| | 3-4 | FP-4 (3) | BP-1 (100) | — | Q-4 (9.66) | PGMEA (3,500) DAA (500) | 85 | 31 | 11 | 2.5 |
| | 3-5 | FP-5 (3.5) | BP-1 (100) | — | Q-2 (4.79) | PGMEA (3,500) DAA (500) | 85 | 33 | 13 | 2.9 |
| | 3-6 | FP-6 (3) | BP-1 (100) | — | Q-2 (4.79) | PGMEA (3,500) DAA (500) | 85 | 35 | 14 | 2.5 |
| | 3-7 | FP-7 (2.5) | BP-1 (100) | — | Q-2 (4.79) | PGMEA (3,500) DAA (500) | 85 | 36 | 12 | 2.4 |
| | 3-8 | FP-8 (2.5) | BP-1 (100) | — | Q-2 (4.79) | PGMEA (3,500) DAA (500) | 85 | 37 | 11 | 2.6 |
| | 3-9 | FP-9 (3) | BP-1 (100) | — | Q-2 (4.79) | PGMEA (3,500) DAA (500) | 85 | 35 | 15 | 2.5 |
| | 3-10 | FP-10 (3) | BP-1 (100) | — | Q-2 (4.79) | PGMEA (3,500) DAA (500) | 85 | 34 | 14 | 2.7 |
| | 3-11 | FP-11 (2) | BP-1 (100) | — | Q-2 (4.79) | PGMEA (3,500) DAA (500) | 80 | 33 | 16 | 2.5 |
| | 3-12 | FP-11 (2) | BP-1 (100) | PAG-1 (3.23) | Q-2 (4.79) | PGMEA (3,500) DAA (500) | 80 | 28 | 12 | 2.6 |
| | 3-13 | FP-11 (2) | BP-1 (100) | PAG-2 (3.03) | Q-2 (4.79) | PGMEA (3,500) DAA (500) | 80 | 28 | 12 | 2.6 |
| | 3-14 | FP-11 (2) | BP-1 (100) | PAG-3 (3.44) | Q-2 (4.79) | PGMEA (3,500) DAA (500) | 80 | 28 | 12 | 2.6 |
| | 3-15 | FP-11 (2) | BP-2 (100) | PAG-4 (19) | Q-2 (4.79) | PGMEA (3,500) DAA (500) | 120 | 48 | 16 | 3.8 |
| | 3-16 | FP-12 (2) | BP-1 (100) | — | Q-2 (4.79) | PGMEA (3,500) DAA (500) | 80 | 35 | 13 | 2.6 |
| | 3-17 | FP-13 (2) | BP-1 (100) | — | Q-2 (4.79) | PGMEA (3,500) DAA (500) | 80 | 34 | 14 | 2.6 |
| Comparative Example | 2-1 | cFP-1 (2) | BP-1 (100) | — | Q-1 (4.71) | PGMEA (3,500) DAA (500) | 85 | 34 | 6 | 2.8 |
| | 2-2 | cFP-2 (2) | BP-1 (100) | — | Q-1 (4.71) | PGMEA (3,500) DAA (500) | 85 | 34 | 2 | 2.9 |
| | 2-3 | cFP-3 2) | BP-1 (100) | — | Q-1 (4.71) | PGMEA (3,500) DAA (500) | 85 | 38 | 0 | 3.2 |
| | 2-4 | cFP-4 (2) | BP-1 (100) | — | Q-1 (4.71) | PGMEA (3,500) DAA (500) | 85 | 39 | 0 | 3.3 |
| | 2-5 | — | BP-1 (100) | — | Q-1 (4.71) | PGMEA (3,500) DAA (500) | 85 | 36 | 0 | 2.8 |
| | 2-6 | — | BP-2 (100) | PAG-4 (19) | Q-2 (4.79) | PGMEA (3,500) DAA (500) | 120 | 52 | 8 | 4.7 |

It is demonstrated in Table 1 that resist compositions comprising a specific fluorocarboxylic acid-containing polymer offer a high sensitivity, reduced LWR and broad window.

Japanese Patent Application No. 2020-079676 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a fluorocarboxylic acid-containing polymer comprising recurring units having the formula (A1):

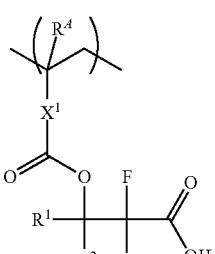

(A1)

wherein $R^A$ is hydrogen or methyl, $R^1$ and $R^2$ are each independently hydrogen, or a $C_1$-$C_{10}$ saturated hydrocarbyl group, $C_2$-$C_8$ unsaturated aliphatic hydrocarbyl group, optionally substituted $C_6$-$C_{10}$ aryl group, or $C_4$-$C_{10}$ monovalent group obtained by combining the foregoing, with the proviso that $R^2$ is other than hydrogen when $R^1$ is a $C_1$-$C_4$ alkyl group, $R^1$ and $R^2$ may bond together to form a ring with the carbon atom to which they are attached, $X^1$ is a single bond, phenylene, naphthalenediyl or —C(=O)—O—$X^{11}$—, $X^{11}$ is a $C_1$-$C_{10}$ saturated hydrocarbylene group or phenylene group, the polymer being free of recurring units containing an acid labile group, and a base polymer.

2. The resist composition of claim 1 wherein 0.001 to 20 parts by weight of the fluorocarboxylic acid-containing polymer is present per 100 parts by weight of the base polymer.

3. The resist composition of claim 1, further comprising an acid generator capable of generating a sulfonic acid, imide acid or methide acid.

4. The resist composition of claim 1, further comprising an organic solvent.

5. The resist composition of claim 1 wherein the base polymer comprises recurring units having the formula (a1) or recurring units having the formula (a2):

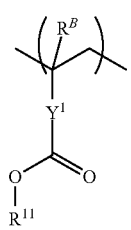
(a1)

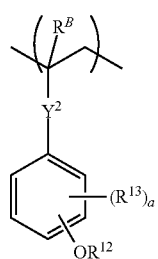
(a2)

wherein $R^B$ is each independently hydrogen or methyl, $R^{11}$ and $R^{12}$ each are an acid labile group, $R^{13}$ is fluorine, trifluoromethyl, a $C_1$-$C_5$ saturated hydrocarbyl group or $C_1$-$C_5$ saturated hydrocarbyloxy group, $Y^1$ is a single bond, phenylene group, naphthylene group, or $C_1$-$C_{12}$ linking group containing at least one moiety selected from ester bond and lactone ring, $Y^2$ is a single bond or ester bond, and a is an integer of 0 to 4.

6. The resist composition of claim 5 which is a chemically amplified positive resist composition.

7. The resist composition of claim 1 wherein the base polymer is free of an acid labile group.

8. The resist composition of claim 7 which is a chemically amplified negative resist composition.

9. The resist composition of claim 1 wherein the base polymer comprises recurring units of at least one type selected from recurring units having the formulae (f1) to (f3):

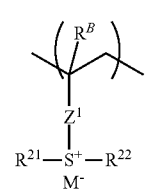
(f1)

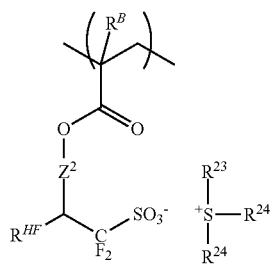
(f2)

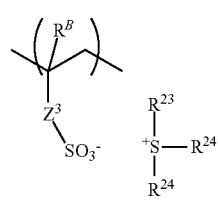
(f3)

wherein $R^B$ is each independently hydrogen or methyl, $Z^1$ is a single bond, a $C_1$-$C_6$ aliphatic hydrocarbylene group, phenylene group, is naphthylene group, or $C_7$-$C_{18}$ group obtained by combining the foregoing, or —O—$Z^{11}$—, —C(=O)—O—$Z^{11}$— or —C(O)—NH—$Z^{11}$—, $Z^{11}$ is a $C_1$-$C_6$ aliphatic hydrocarbylene group, phenylene group, naphthylene group, or $C_7$-$C_{18}$ group obtained by combining the foregoing, which may contain a carbonyl moiety, ester bond, ether bond or hydroxyl moiety, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ saturated hydrocarbylene group which may contain a carbonyl moiety, ester bond or ether bond, $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxyl moiety, $R^{21}$ to $R^2$ are each independently halogen or a $C_1$-$C_{20}$ hydrocarbyl group which may contain a heteroatom, a pair of $R^{23}$ and $R^{24}$ or $R^{26}$ and $R^{27}$ may bond together to form a ring with the sulfur atom to which they are attached, $R^{HF}$ is hydrogen or trifluoromethyl, and $M^-$ is a non-nucleophilic counter ion.

10. The resist composition of claim 1, further comprising a surfactant.

11. A process for forming a pattern comprising the steps of applying the resist composition of claim 1 onto a substrate to forma resist film thereon, exposing the resist film to high-energy radiation, and developing the exposed resist film in a developer.

12. The process of claim 11 wherein the high-energy radiation is ArF excimer laser radiation of wavelength 193 nm or KrF excimer laser radiation of wavelength 248 nm.

13. The process of claim 1 wherein the high-energy radiation is EB or EUV of wavelength 3 to 15 nm.

* * * * *